(12) United States Patent
Zabel et al.

(10) Patent No.: US 6,706,251 B1
(45) Date of Patent: Mar. 16, 2004

(54) COLLOID FOR SCINTIGRAPHY

(75) Inventors: Pamela Louise Zabel, St. Mary's (CA); Kent Dunn, Burlington (CA)

(73) Assignee: London Health Sciences Centre, London ( * ) Notice: Subject to any disclaimer, the term of this patent is extended or adjusted under 35 U.S.C. 154(b) by 0 days.

(21) Appl. No.: 09/926,219

(22) PCT Filed: Mar. 24, 2000

(86) PCT No.: PCT/CA00/00326

§ 371 (c)(1),
(2), (4) Date: Dec. 21, 2001

(87) PCT Pub. No.: WO00/57924

PCT Pub. Date: Oct. 5, 2000

Related U.S. Application Data

(60) Provisional application No. 60/126,379, filed on Mar. 26, 1999.

(51) Int. Cl.$^7$ .............................................. A61K 51/00
(52) U.S. Cl. ..................................................... 424/1.29
(58) Field of Search ............................... 424/1.11, 1.21, 424/1.25, 1.29, 1.33, 1.37; 534/14

(56) References Cited

U.S. PATENT DOCUMENTS

| | | | |
|---|---|---|---|
| 3,810,976 A | 5/1974 | Halpern et al. | |
| 3,845,202 A | 10/1974 | Cohen et al. | |
| 6,153,388 A | * 11/2000 | Reintgen | ....................... 436/6 |

FOREIGN PATENT DOCUMENTS

| | | |
|---|---|---|
| BE | 883 114 A | 11/1980 |
| FR | 2 088 139 A | 1/1972 |
| FR | 2 107 902 A | 5/1972 |

OTHER PUBLICATIONS

Persson R.B.R. et al., "Technetium–99m Sulfide Colloid Preparation for Scintigraphy of the Reticuloendothelial System", Acta Radiol. Ther. Phys. Biol., 1970, vol. 9, 567–576.
Boulahdour, H., et al., "The Hot Spot Hepatobiliary Scan in Focal Nodular Hyperplasia", J. Nucl. Med. 1993 Dec;34(12) pp 2105–2110.
Boyd, R.E., "The Gel Generator: a Viable Alternative Source of Tc for Nuclear Medicine", Applied Radiation and Isotopes, vol. 48, No. 8, pp 1027–1033, 1997.
Cohen, Marvin B., et al. "Rhenium and Technetium Heptasulfide", J. Nucl. Med., 1972, vol. 123, No. 4, p 287.
Frier, M., et al. "The Biological Fate of Sulphur Colloid", Eur.J.Nucl.Med., 1981, vol. 6, pp 371–374.
Frier, M., et al., "The Physical and Chemical Characteristics of Sulphur Colloids", Eur. J.Nucl.Med. 1981, vol. 6, pp 255–260.
Gommans, G.M.M., et al., "Further optimisation of $^{99m}$Tc–Nanocoll sentinel node localization in carcinoma of the breast by improved labeling", J.Nucl.Med. Oct. 10, 2001 vol. 28, No. 10pp. 1450–1455.

Hosal, N., et al. "Lymphoscintigraphy in pectoralis major myocutaneous flaps", Arch Otolaryngol. Head Neck Surg. 1994, vol. 6, pp 659–661.
Larson, S.M., et al. "Radiopharmacology of a Simplified Technetium–99m–Colloid Preparation for Photoscanning", J.Nucl. Med., 1966; vol. 7, pp. 817–826.
Lock–Andersen, J. et al., "Preoperative Cutaneous Lymphoscintigraphy in Malignant Melanoma", Cancer 1989, Jan 1;63(1) pp 77–82.
Nakajima, Kenichi, et al. "Biodistribution of technetium—99m– rhenium colloid in rats: a comparison with technetium – 99m– sulfur colloid", Kaku Igaku, 1981, vol. 18, No. 7, pp 967–71.
Paradelo C., et al., "Lymphoscintigraphy in the study of lymphatic drainage patterns in . . . ", Med.Clin.(Barc.) 1999, vol. 8, pp 281–284.
Peltier, P., et al., "$^{99m}$Tc–DTPA and $^{99m}$Tc–rhenium sulfur compared as adj patients with suspected pulmonary embolism", Eur.J.Nucl.Med. 1986, vol. 12, pp. 254–257.
Samochocka, Krystyna, et al. "Some Comments Concerning the preparation of colloidal sulfides labeled with technetium – 99m and indium—113m and used in clinical scanning", Nuclear–Medizin, 1971, vol. 10, No. 3, pp 252–255.
Santos, A.C., et al. "Cardiac lymphatic dynamics after ischemia and reperfusion–experimental model—Basic concepts for optimal uptake of radiocolloids in the parasternal lymph nodes of rabbits", Nucl. Med. & Biology, vol. 25, No. 7, Oct. 1998, pp 685–688.
Szymendera, J., et al., "Chemical and Electron Microscope Observations of a Safe PVP–Stabilized Colloid for Liver and Spleen Scanning", J.Nucl.Med. 1971, vol. 12(5) pp 212–215.
Steigman, J., et al. "Technetium–Sulfur Colloid", Appl.Radiat.Isot., 1986, vol. 37, No. 3, pp 223–229.
Szymendera, J., et al. "Rhenium and Technetium Heptasulfide—the Author's Reply", J. Nucl. Med., 1972, vol. 13, No. 4, pp 287–288.
Takahashi, Kunibumi, "Short half–lived radiocolloids for delineation of the reticuloendothelial system in the bone marrow", Sci. Rep. Res. Inst. Tohoku Univ., Ser. C, 1974, vol. 21, No. 3–4, pp 35–46.
Thibaut, G., et al., "Measurement of Lymphatic Flow Variation by Noninvasive Method . . . ", Angiology 1992 Jul;43(7) pp 567–571.

* cited by examiner

*Primary Examiner*—Michael G. Hartley
(74) *Attorney, Agent, or Firm*—Bereskin & Parr

(57) ABSTRACT

A new formulation of Tc-99m colloid is described. The new colloid contains a high ratio of perrhenate to thiosulphate, cysteine, and a prepared higher final pH than found previously. In preparing the colloid preferred rhenium sulfide is not used as an ingredient. The pH of the final formulation and can be between about 5.5 an about 8.0, and the ratio of rhenium to sulfur is from about 0.05 to about 1.2. In addition, the new colloid has excellent radiochemical purity, and a much smaller particle size distribution than has generally been previously available for sulfur colloid preparations.

70 Claims, 24 Drawing Sheets

FIGURE 2: Sulfur Colloid with & without Cysteine

FIGURE 4: Kinetics of Boiling Time for Rhenium Colloid

FIGURE 6: Percent Injected Dose in the Sternum

FIGURE 7: Biokinetics of Tin Colloid

%Colloid smaller than 0.22u for Three Preparations
With and without cysteine

FIGURE 13: Mouse Biodistribution: Tc Sulfur vs Rhenium colloid

Kinetics of Tc-99m Rhenium Colloid: Boiling Time vs Radiochemical Purity and Particles less than 0.22 u filtration size

FIGURE 19
A  Percentage of Radioactivity Retained at Injection Site
Tc-99m Rhenium Colloid
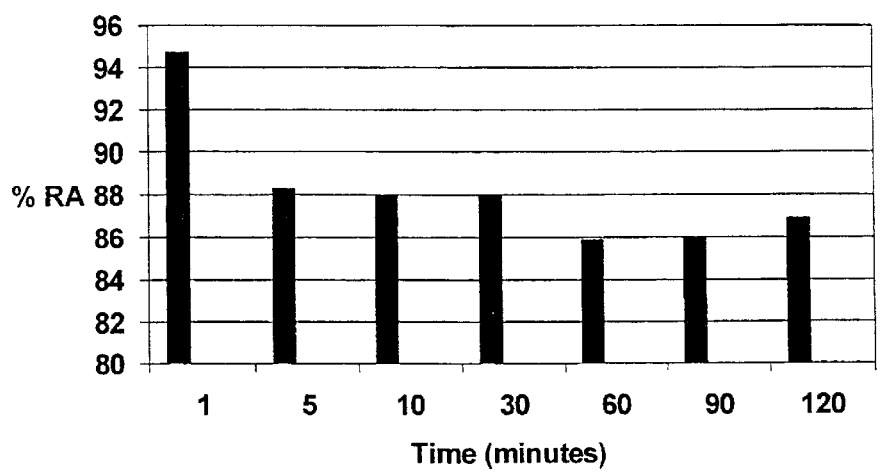
B Percentage Migration of Tc-99m Rhenium Colloid in Lymphatic Nodes/Vessels
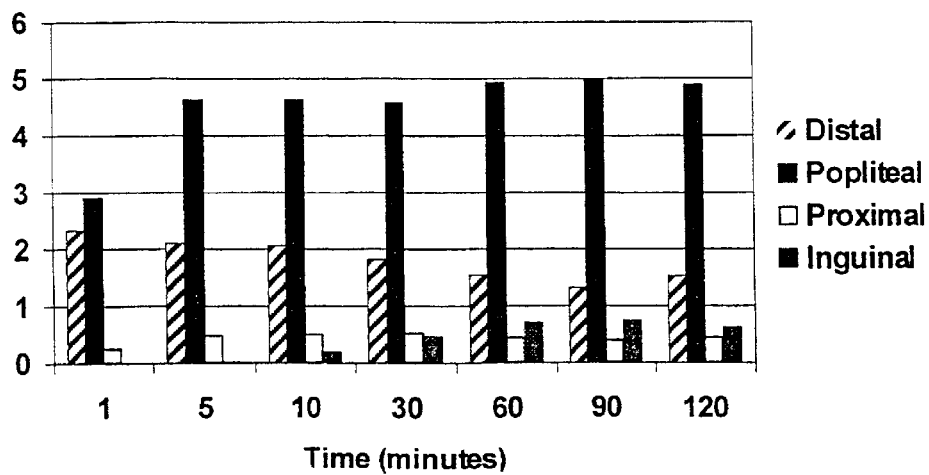

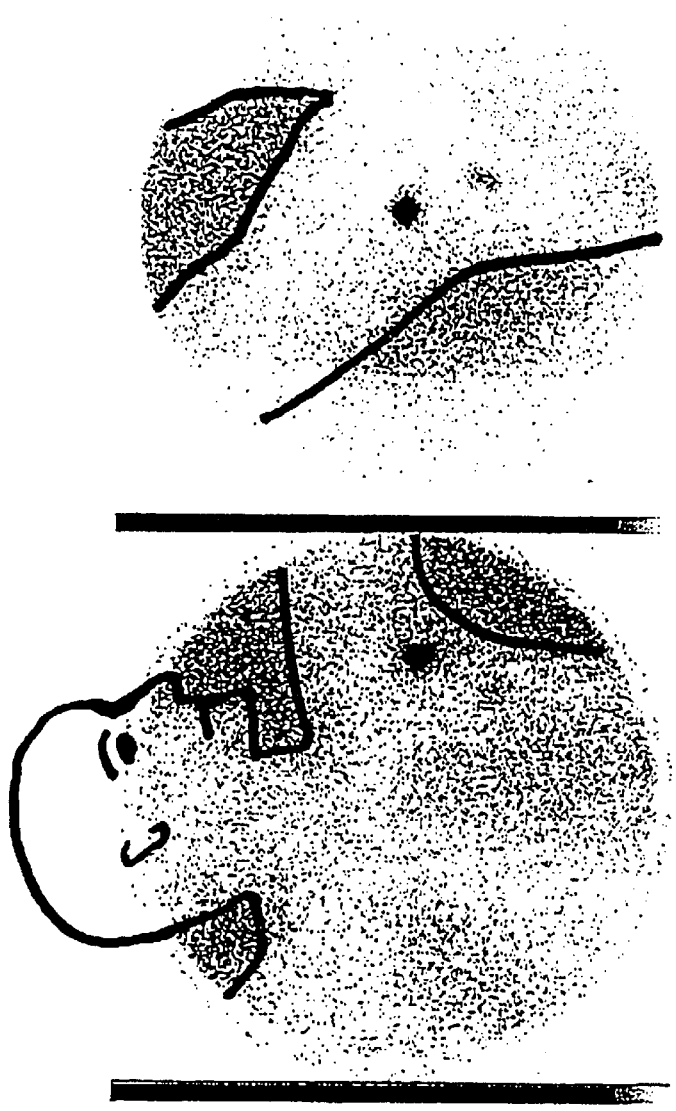

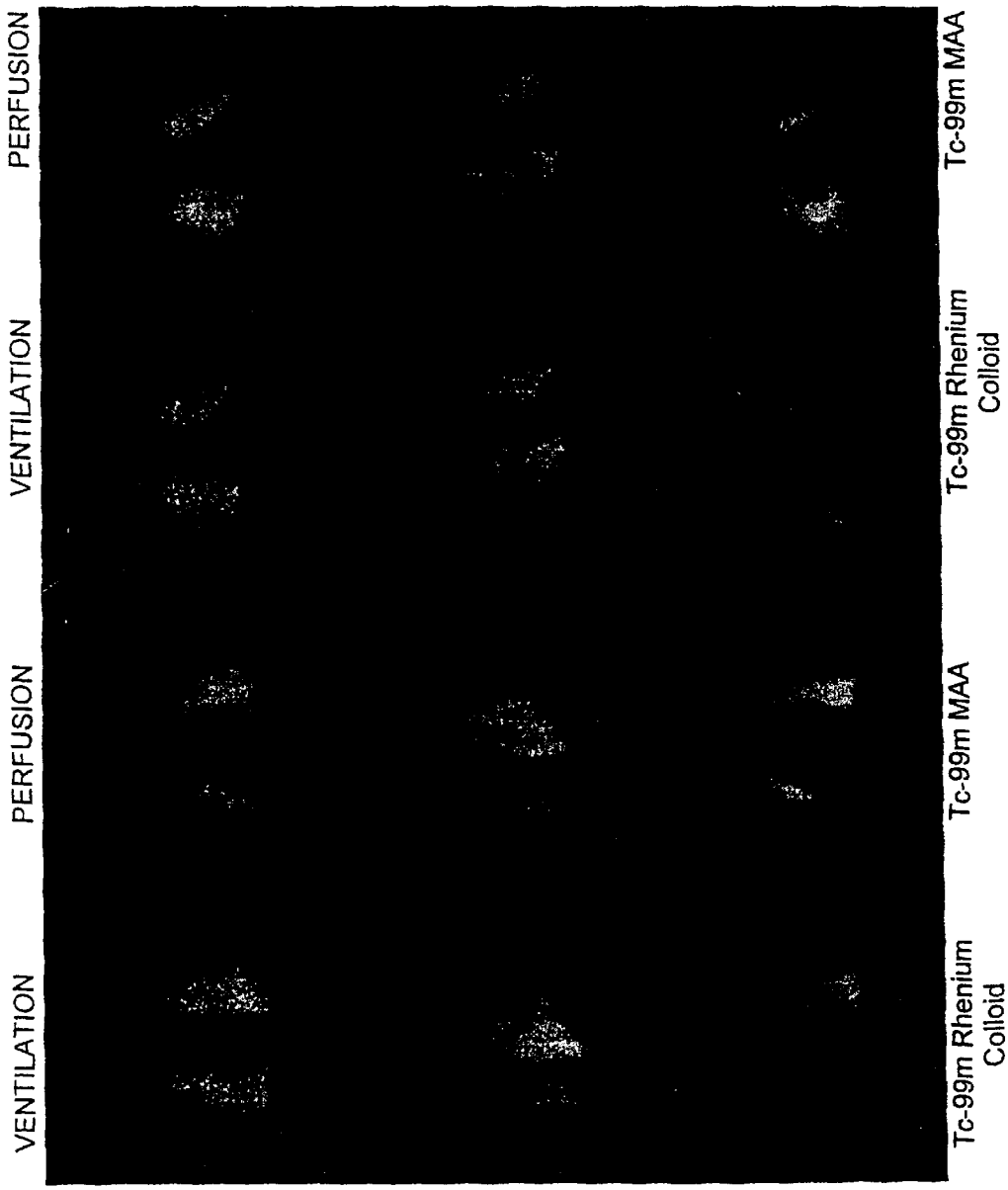

COLLOID FOR SCINTIGRAPHY

RELATED APPLICATIONS

The present application is the national phase entry of PCT patent application number PCT/CA00/00326, filed on Mar. 24, 2000 which claims the benefit of priority under 35 U.S.C. §119(e) from U.S. provisional patent application No. 60/126,379, filed on Mar. 26, 1999.

FIELD OF THE INVENTION

This invention is in the field of diagnostics in radiography and radioimaging and is more particularly concerned with a composition and method of preparing the composition for use in scintigraphy.

BACKGROUND OF THE INVENTION

For most patients with solid tumors, the most powerful and predictive prognostic factor of survival is the status of regional lymph nodes (Albertini et al. (1996); Cox C. (1998); De Cicco et al. (1997); Reintgen and Conrad (1997)). Hence it remains important to identify those patients with nodal involvement in order to differentiate those patients who will clearly benefit from systemic treatment. The sentinel node is that lymph node in a given lymphatic basin that first receives lymphatic flow from a primary tumor (Gulec et al. (1997)). As a result the histology of the sentinel node usually reflects the histology of the basin. Therefore, if there is cancer in the sentinel node, there may be metastatic disease in other nodes, but, if the sentinel node is cancer-free, there is greater than 98% likelihood that the remaining nodes in the basin are negative. Thus, the sentinel node is the best tissue to sample for histopathologic examination (Alazraki et al. (1997)).

Sentinel node lymphoscintigraphy (SNL) has made it possible to perform complete lymph node dissection only in those patients with confirmed nodal metastasis. SNL therefore reduces the surgical morbidity associated with such a procedure including: parasthesia, wound infection, seroma, drain discomfort, acute and chorin lymphodema, as well as potential delays in adjuvant therapy (Cox (1998); Hinkle (1998)). Furthermore, lymphatic mapping and sentinel node biopsies direct dissection to all lymph node beds that could have tumors. Not infrequently, a sentinel lymph node that shows micrometastasis is in a lymph node bed that would not have been predicted to receive lymphatic drainage from the primary tumor based on conventional estimates (Alazraki et al. (1997)). The classic concept of a lymphatic watershed described by Sappey's line (an anatomic coordinate governing the direction of lymphatic flow from any point on the trunk) has been shown by lymphoscintigraphy to be erroneous (Ege G: Lymphoscintigraphy in Oncolgy. Chapter 94 Nuclear Medicine Volume II. Mosby Year Book, St. Louis, Mo. 1504–1523).

The procedure involves injecting radiopharmaceuticals (specifically radiolabeled colloid of suitable size and properties) at the primary tumor site, which allows the path of lymphatics, for example from a cutaneous melanoma or breast lesion, to the regional node basin to be traced. Using the nuclear images as a road map, gamma probe guided surgery (with a hand-held, wand-like instrument that detects gamma rays emitted by the radiocolloid) successfully locates the sentinel node, allowing a directed dissection and minimizing tissue disruption (Alazraki (1998); Pijpers et al. (1995)). The fact that only one or two nodes need examination makes it possible for the pathological investigation to apply techniques such as immunohistochemical staining and PCR-based assays which are more sensitive than routine H&E staining for detecting micrometastasis (Guiliano et al. (1997); Reintgen and Conrad (1997)).

Small Colloids

Technetium-labeled sulfur (Tc—S) colloids have been used for years to image the reticuloendothelial system. There are three reported methods of making such preparations:

(1) $^{99m}TcO^-_4 + H_2S$ in acid solution;

(2) $^{99m}TcO^-_4 + Sb_2S_3$ colloid in acid, and (3) $^{99m}TcO^-_4 + Na_2S_2O_3 +$ acid.

The major commercial source of Tc—S colloid preparations is the reaction mixture formed from pertechnetate-99m in an acidified solution of sodium thiosulphate (Atkins, H. L., et al. (1966); Stern H. S., et al. (1966)). Such standard preparations result in a final pH on average of between 5.0 and 6.5. Such pH values cause significant irritation in patients often requiring a local anesthetic to accompany the injection.

There are several desirable characteristics of the ideal radiocolloid for use in SNL including ease of labeling; sutiable half life and energy characteristics; permitting quantitative or dynamic measurement and high quality imaging; ease of preparation and good shelf life; physiologically and chemically inert and homogeneous; sterility and pyrogenicity readily established via Quality Control procedures; in vitro and in vivo stability; and optimal mobilization of colloid from injection site. However the rate of colloid transport and movement through lymphatic pathways is most strongly related to the size of the colloid. Those larger than 0.004 μm to 0.005 μm are preferred, as smaller particles have been reported to penetrate the capillary membranes and are therefore unavailable to migrate through the lymphatic channels resulting in obscured images. Particles smaller than 0.1 μm show the most rapid disappearance from the interstitial space into the lymphatic vessels and have significant retention in the lymph node. Large colloid particles (~0.5 μm) show a much slower rate of clearance from the interstitial space with significantly less accumulation in the lymph nodes (Alazraki et al. (1997); Bergqvist et al. (1983); Ege G: Lymphoscintigraphy in Oncolgy. Chapter 94 Nuclear Medicine Volume II. Mosby Year Book, St. Louis, Mo. 1504–1523; Eshima et al. (1996); Hung et al. (1995); Nagai et al. (1982)).

Several reports indicate that the physico-chemical properties of these colloids influence the efficiency of their phagocytosis (Dobson (1957; Neukomm et al. (1957); Scott et al. (1967); Atkins et al. (1970)), and some investigators have described anomalies in the behaviour of sulfur colloid (Chaudhuri and Evans (1973); Haiback et al. (1975); Bradfield and Wagner (1977)).

SUMMARY OF THE INVENTION

The present inventors have developed a new formulation of Tc-99m colloid. The new colloid contains a high ratio of perrhenate to thiosulphate, cysteine, and a prepared higher final pH than found previously. As used herein, a "final pH" means the pH of the final formulation and can be between about 5.5 and about 8.0, but is preferably between about 7.0 and about 7.5. Also, as used herein, "high ratio" means from about 0.05 to about 1.2 rhenium:sulfur and in any event, less than rhenium and no sulfur. In addition, the new colloid has excellent radiochemical purity, and a much smaller particle size distribution than has generally been previously available for sulfur colloid preparations.

Accordingly, the present invention provides a colloid particle, containing a high ratio of rhenium to sulfur, and containing a source of sulfhydryl groups (—SH), and technetium, preferably wherein the particle is less than about 0.1 micron in diameter and the technetium is Tc-99m.

The invention also provides a colloid containing a high ratio of rhenium to sulfur, and containing a source of —SH, and technetium wherein a majority of the particles, preferably greater than about 80% of the particles, of the colloid, are less than about 0.1 micron in diameter and the technetium of these particles is Tc-99m.

According to another aspect, the invention provides a method of preparing a colloid containing a high ratio of rhenium to sulfur, and containing a source of —SH, and technetium comprising the steps of: in a container adding a source of sulfur and a source of rhenium; adding a source of technetium; before boiling adding a source of —SH; acidifying the contents of the container; boiling the contents of the container; cooling the contents of the container; raising the pH of the contents of the container to a higher final pH between about 5.5 to about 8.0, preferably between about 7.0 and about 7.5.

Also provided is a method of detecting sentinel lymph node(s) associated with a tumor comprising administering a sufficient amount of a radiopharmaceutical colloid according to the present invention to an animal, detecting radiation emitted from the animal, and correlating the emissions to locate the associated sentinel lymph node(s).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 19A and B are a graphs illustrating the migration of radioactive colloid in various lymphatic regions in rabbits for 2 hours after intradermal injection sites by showing amounts left at the injection site.

FIG. 23 provides 3 panels illustrating nuclear medicine images showing migration from injection site from melanoma to opposite axilla with Tc-99m-ReC.

FIG. 24 is a composite of nuclear medicine lung scans after inhalation of aerosolized (nebulized) using the ReC of the present invention.

DETAILED DESCRIPTION OF THE INVENTION

Colloid

Figure 1:
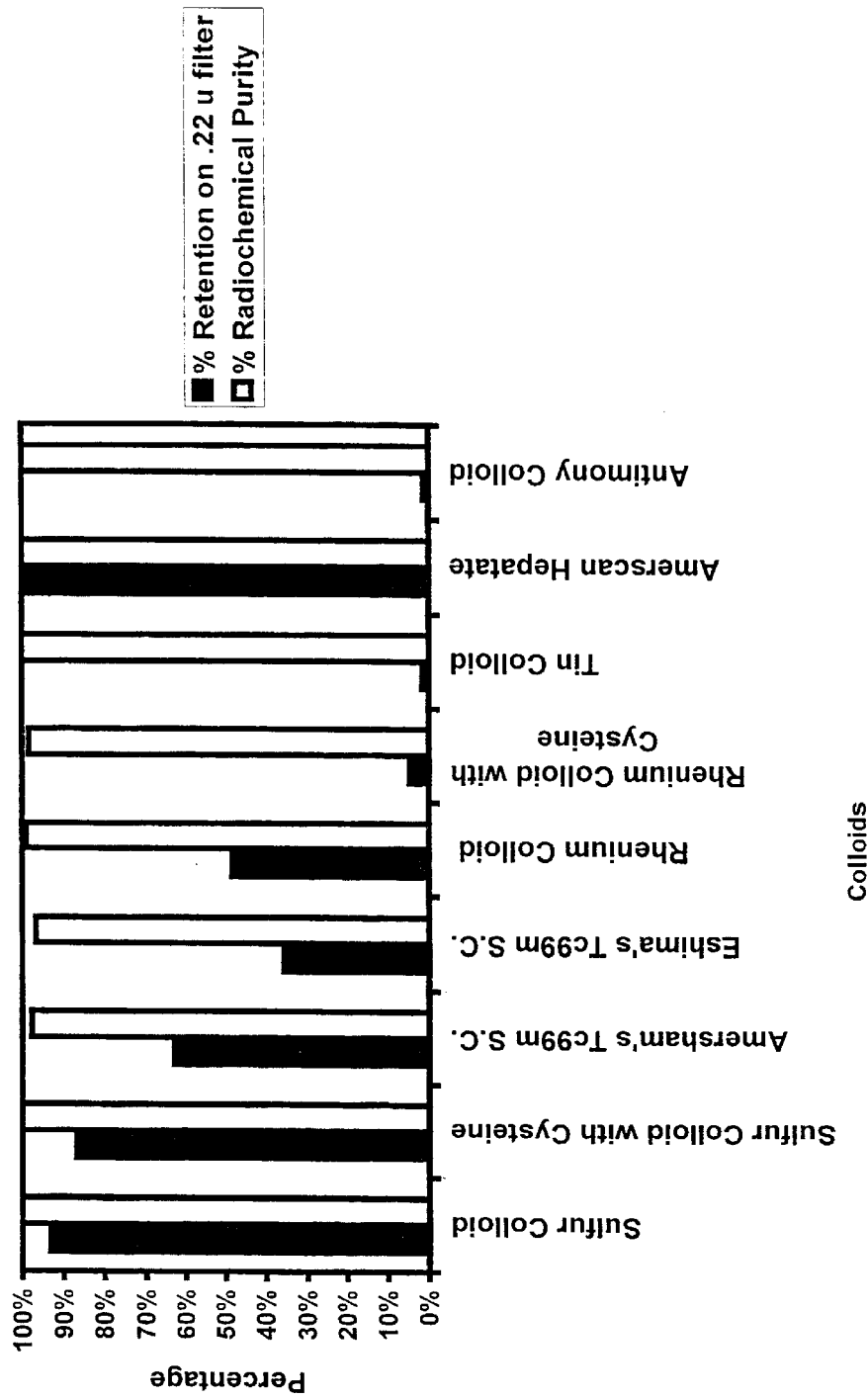
FIG. 1 is a histogram illustrating percentage of retention on a 0.22 µm filter and the radiochemical purity of various colloids.

As mentioned above, the present inventors have developed a new technetium colloid which contains a high ratio of perrhenate to thiosulphate, cysteine, and a preferred higher final pH than found previously, and has excellent radiochemical purity, and a much smaller particle size distribution than has generally been previously available for sulfur colloids.

Accordingly, the present invention provides a colloid particle, containing a high ratio of rhenium to sulfur, preferably greater than about 0.05 and less than about 1.2, preferably about 0.3, and containing a source of —SH, and technetium. It will be understood by those skilled in the art that a variety of sources for rhenium are available including sodium or potassium perrhenate, perrhenic acid, rhenium chloride, rhenium fluoride, rhenium oxide, preferably, the source of rhenium is perrhenate. It will also be understood that a variety of sources of sulfur are available, preferably, the source of sulfur is thiosulfate. The source of —SH is selected from the group consisting of inorganic sulphide, and organic thiols, more preferably the organic thiol is selected from the group consisting of cysteine, glutathione and peptides, and of these preferably cysteine.

For the purposes of this disclosure, a "high ratio of rhenium to sulfur" means the molar ratio of rhenium to sulfur. In preparations described herein the molar ratio of thiosulfate to perrhenate is as folows: sodium thiosulfate 1.5 mg/158 g/mole=9.49 umoles, and taking into account the fact that there are two sulfur atoms in every molecule of thiosulfate means there are 18.98 umoles of sulfur. As for sodium perrhenate, 1.17 mg/27319 g/mol=4.29 umoles, and there is only one Re in each molecule of perrhenate. Consequently, when comparing Re(perrhenate) to S atoms (thiosulfate . . . ignore cysteine) then the ratio that exists in the rhenium preparation is 4.29/18.98=0.23—if comparing the molar amounts of the initial compounds, the ratio is 0.4516. The molar ratio in the "in-house" sulfur colloid preparation is ⅓ this amount since it has three times as much thiosulfate. Accordingly, a "high ratio" means a molar ratio of rhenium to sulfur of about 0.05 to about 1.1, preferably about 0.25.

According to a preferred embodiment the colloid particle size is less than about 0.1 micron in diameter and for use in the radio imaging field the technetium is Tc-99m.

Accordingly, the present invention provides a colloid, containing a high ratio of rhenium to sulfur, preferably greater than about 0.05 and less than about 1.2, preferably about 0.3, and containing a source of —SH, and technetium. It will be understood by those skilled in the art that a variety of sources for rhenium are available including sodium or potassium perrhenate, perrhenic acid, rhenium chloride, rhenium fluoride, rhenium oxide, preferably, the source of rhenium is perrhenate. It will also be understood that a variety of sources of sulfur are available, preferably, the source of sulfur is thiosulfate. The source of —SH is selected from the group consisting of inorganic sulphide, and organic thiols, more preferably the organic thiol is selected from the group consisting of cysteine, glutathione and peptides, and of these preferably cysteine.

According to a preferred embodiment the colloid is one wherein a majority of the particles, and preferable greater than about 80% of the particles, are less than about 0.1 micron in diameter and in these particles of the colloid, the technetium is Tc-99m.

According to one embodiment the colloid has a final pH of about 5.5 to about 8.0, preferably about 7.0 to about 7.5, more preferably 7.4.

Preparation of Colloids

The inventors have found that adding cysteine before boiling provides a preferred colloid. In this respect, according to another aspect of the invention there is provided a method of preparing a colloid containing a high ratio of rhenium to sulfur, and containing a source of —SH, and technetium comprising the steps of: in a container adding a source of sulfur and a source of rhenium; adding a source of technetium; prior to boiling adding a source of —SH; acidifying the contents of the container; boiling the contents of the container; cooling the contents of the container; raising the pH of the content of the container. It will be understood by those skilled in the art that a variety of sources for rhenium are available including sodium or potassium perrhenate, perrhenic acid, rhenium chloride, rhenium fluoride, rhenium oxide, preferably, the source of rhenium is perrhenate. It will also be understood that a variety of sources of sulfur are available, preferably, the source of sulfur is thiosulfate. The source of —SH is selected from the group consisting of inorganic sulphide, and organic thiols, more preferably the organic thiol is selected from the group consisting of cysteine, glutathione and peptides, and of these preferably cysteine.

It will be understood by those skilled in the art that colloid preparations routinely include a gelatin and as such, a colloid and a method of making a colloid according to the present invention includes the incorporation of a gelatin.

According to a preferred embodiment the colloid particle size is less than about 0.1 micron in diameter and for use in the radio imaging field the technetium is Tc-99m.

According to the method, the amount of cysteine added is sufficient to bring about a reduction in the size of particles, most importantly the source of —SH, for example cysteine, is to be added before boiling.

According to an embodiment of the method the amount of cysteine added is between about 0.5 and about 50 mg, preferably about 6 mg, and preferably the the boiling time is from about six (6) to about ten (10) minutes, most preferably about eight minutes, and the cooling time is from about zero to about ten minutes, preferably about 8 to about 10 minutes. The pH is increased to a final pH of between about 5.5 to about 8.0, preferably about 7.0 to about 7.5 using any buffer, preferably a phosphate buffer. Preferably the method provides a colloid wherein a majority of the particles, preferably greater than about 80% of the particles of the colloid are less than about 0.1 micron in diameter.

According to a method of the invention where the colloid is to be used for radiography the technetium of the particles which are less than about 0.1 micron in diameter, is preferably Tc-99m and the final pH of the colloid is 7.4. Although the present description of the invention refers to Tc-99m, it will be understood by those skilled in the art that $^{196}$Tc or $^{198}$Tc may also be used. It will also be appreciated that other sources of radioactivity may be employed rather than technetium depending on circumstances in which the colloid is to be utilized.

Figure 14:
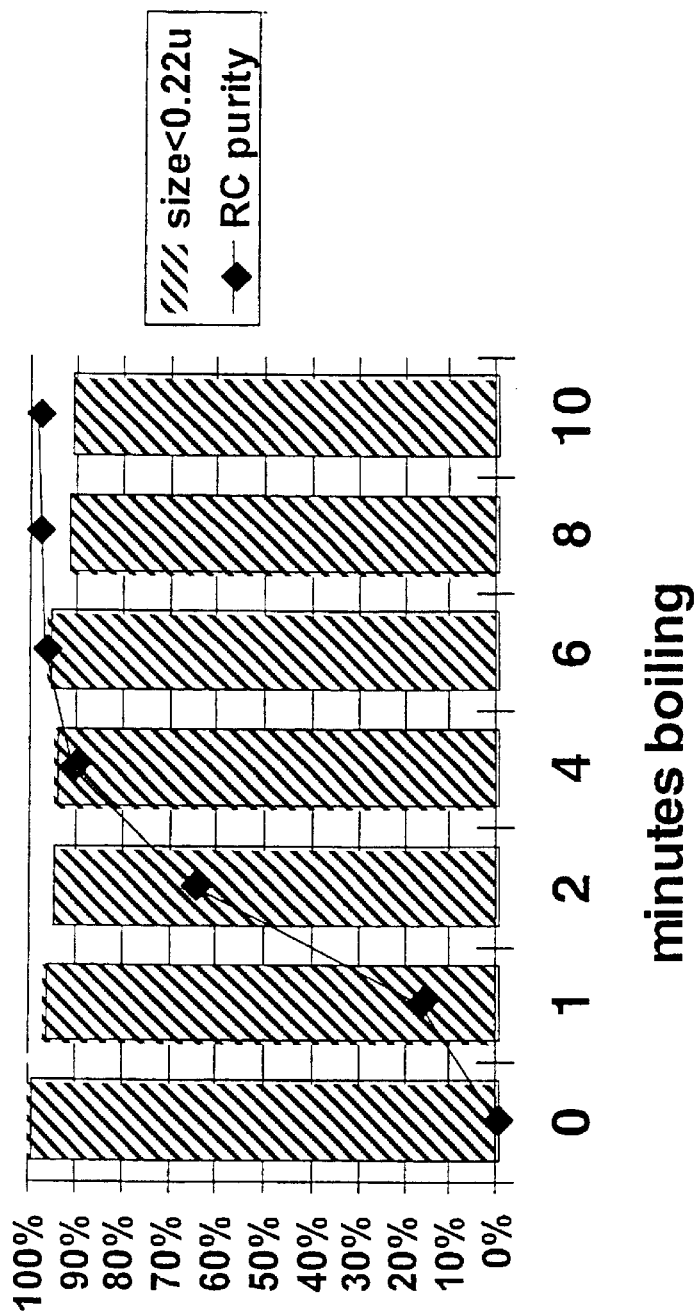
FIG. 14 is a histogram/graph presentation of results illustrating the changes in radiochemical purity in particles less than 0.22 microns with increasing boiling time.

According to another aspect of the invention there is provided a method of preparing a colloid containing a source of sulfur, a source of —SH and a radioactive source wherein the method comprises adding to a container the source of sulfur and the source of radioactivity, adding the source of —SH prior to boiling, acidifying the contents of the container, boiling the contents of the container, cooling the contents of the container and raising the pH of the contents of the container. Preferably the source of sulfur is thiosulphate, the source of radioactivity is Tc-99m and the source of —SH is cysteine. Acidification may be brought about with any acid, preferably NCl. The pH may be raised with any buffer, preferably phosphate, to a pH of between about 5.5 and about 8.0, preferably about 7.0 to about 7.5, most preferably 7.4. The boiling time can be from between about six (6) to about ten (10) minutes, most preferably about eight (8) minutes, and the cooling time is from about zero to about ten minutes, preferably about 8 to about 10 minutes, more preferably 2–4 minutes. With respect to boiling time it is understood that this time can be from 10 seconds to 2 minutes to as much as 1 hour, however, as illustrated in FIG. 14, the preferred time is about 8 minutes.

Preferably the method provides a colloid wherein a majority of the particles, preferably greater than about 80% of the particles of the colloid are less than about 0.1 micron in diameter.

In a preferred embodiment, the preparation of a colloid according to the present invention involves the addition of $^{99m}$Tc pertechnetate (radioactive label) to a container, such as a vial, containing a chemical or chemicals which forms the bulk of the radioactive colloidal particle (for example, perrhenate as the rhenium source or thiosulphate as a sulfur source). To this solution is then added a source of sulphydryl groups, such as cysteine, and the solution is then acidified with a suitable acid, such as hydrochloric acid (HCl). This is then boiled, and cooled and then neutralized with a suitable base such as for example phosphate buffer. The source of the $^{99}$Tc per technetate is eluted from a $^{99}$Mo/Tc99m generator, the process of elution/removal is referred to as "milking". The length of time between milkings will affect the degree of incorporation of $^{99}$Tc and $^{99m}$Tc (delayed elutions have greater quantities of chemical technetium— $^{99}$Tc and $^{99m}$Tc). Typically the pH of the resultant colloids may be assessed by any standard means including using pH paper or a pH meter.

Radiochemical Purity and Stability of Colloids

The radiochemical purity (RCP) of colloids may be determined by a number of methods well known to those skilled in the art. One such method is the use of instant thin layer chromagraphy silica gel (ITLC-SG) chromatography paper as the stationary phase and methyl ethyl ketone (MEK) and saline as mobile phases. A comparison of RCP obtained for MEK and saline sheds light on the chemical nature of any impurities present in the colloid prepared. Typically where radioactive labels are involved, radiolabeled products are shaken well before withdrawal of the colloid sample. The sample is applied at the origin of the chromatography strip and the paper strip is placed in a chromatography chamber with an approved solvent or mobile phase solvent. The solvent is allowed to run a sufficient distance after which the strips may be dried in a convenient manner, typically in air at room temperature. The resulting strips may be analyzed using a analyzers well known in the art, for example a Shimadzu Chromatopac™ thin layer chromatogram scanner. Comparing the RCP values obtained at different times, for example 0 and 6 and 24 hours post-production, provides and assessment of a sample's in vitro stability.

Size Evaluation of Radiolabeled Colloids

Radioactive particle size distribution of a colloid may be evaluated by, for examples, ultrafiltration, ultracentrafugation, transmission and electron microscopy. A rapid approach which provides meaningful results is membrane filtration with hydrophilic polyvinylidene fluoride micropore filters (eg. Millipore™). The percentage of radioactivity retained on a filter is expressed as a percentage of the total activity (i.e., filter+filtrate). Filtering may be performed at different times, e.g., 1, 6 and 24 hours after production, in order to determine any temporal changes in particle characteristics.

Methods of Detection

As discussed above, the sentinel node is that lymph node in a given lymphatic basin that first receives lymphatic flow from a primary tumor, and consequently the sentinel node usually reflects the histology of the basin: if there is cancer in the sentinel node, there may be metastatic disease in other nodes. If the sentinel node is cancer-free, there is greater than 98% likelihood that the remaining nodes in the basin are negative. Sentinel node lymphoscintigraphy (SNL) has made it possible to perform complete lymph node dissection only in those patients with confirmed nodal metastasis. SNL therefore reduces the surgical morbidity associated with such a procedure including: parasthesia, wound infection, seroma, drain discomfort, acute and chorin lymphodema, as well as potential delays in adjuvant therapy. Thus, according to another aspect of the invention there is provided a method of detecting the sentinel lymph node(s) associated with a primary tumor such as in breast cancer. The method comprises administering an effective amount of a radiopharmaceutical colloid according to the present invention to an animal, detecting radiation emitted from the animal, and correlating the emissions to locate the associated sentinel lymph node(s) for further pathology diagnosis and tumor staging. This method of detection may be used in connection with any form cancer which is known to metastasize via lymph nodes and includes breast cancer, melanoma, squamous cell carcinoma, and testicular cancer.

Other methods of use of the colloids of the present invention include bone marrow scintigraphy, lung ventilation scintigraphy and liver and spleen scintigraphy. A "radiopharmaceutical colloid" is a colloid according to the present invention which is radioactive, preferably using Tc-99m.

As used herein the term "animal" includes all members of the animal kingdom including mammals, preferably humans.

Administration of an "effective amount" of a colloid of the present invention is defined as an amount effective, at dosages and for periods of time necessary to achieve the desired result. The effective volume/quantity of radioactivity in the colloid and concentration of colloid amount of a colloid of the invention may vary according to factors such as the disease state, age, sex, and weight of the animal. Dosage regima may be adjusted to provide the optimum response. For example, several divided doses may be administered or the dose may be proportionally reduced as indicated by the exigencies of the situation.

As well, the present invention may have a very wide range of radioactivity while maintaining radiochemical purity (RCP), for example, the range may be from 100 $\mu$Ci to 300 mCi.

The following non-limiting examples are illustrative of the present invention:

EXAMPLES

Materials and Methods

Preparation of Colloids

The colloids listed in Table 1 were assessed. With respect to sulfur colloids a commercial colloid was tested as well as an "in-house" sulfur colloid. The commercial preparation was a TSC-mediphysics product marketed in Canada by Amershan. It is identified in the results as the "commercial sulfur colloid", or, in the figures as "TSC" or "Amer (Mon)". The "in-house" sulfur colloid is referred to as "sulfur colloid" or "SC", or "Tc-99m sulfur colloid", or "RNP SC" or "Clinical SC" or "Clin SC", or "Tc Sulfur". The present examples involved testing the effects of altering the standard preparation parameters typically used in the preparation of colloids, specifically: the length of time of boiling, cooling; when the solution is neutralized; the volume of HCl or $PO_4^-$ added; and the length of time since the generator was last milked. The pH of the resultant colloids was assessed using pH paper and in some cases a pH meter. The in-house SC was composed of the following:

Solution A
potassium perrhenate 1.17 mg
gelatin 3.38 mg
dipotassium phosphate 10.1 mg
sodium thiosulfate 4.5 mg
disodium Edetate 1.01 mg, all in 1.5 ml solution.
Solution B
0.5 N HCl 0.5 ml
Solution C
sodium phosphate dibasic.$7H_2O$ 66 mg/ml
sodium phosphate monobasic 1 mg/ml
Use 1 ml after boiling pH of final product typically 5.8–6.2.

The in-house ReC described below was composed of the following:

Solution A
potassium perrhenate 1.17 mg
gelatin 3.38 mg
dipotassium phosphate 10.1 mg
sodium thiosulfate 1.5 mg
disodium Edetate 1.01 mg, all in 1.5 ml solution.
Solution B
cysteine hydrochloride monohydrate 2 mg
0.5 N HCl 0.5 ml
Solution C
sodium phosphate dibasic.$7H_2O$ 66 mg/ml
sodium phosphate monobasic 1 mg/ml
pH adjusted to 8.3
Use 2.5 ml after boiling, final pH typically 6.8–7.8 ideally 7–7.4

A sample protocol for preparation of Tc-99m rhenium colloid is:

1. plug in boiling water bath;
2. do not add the various ingredients until it has come to complete rolling boil;
3. To Vial A containing 1.5 mL Re Colloid solution;
4. Draw up approximately 1.0–7.0 GBq of $^{99m}$Tc-pertechnetate (can use 0.02–15 GBq);
5. qs to 0.5–3 mLs with Sodium Chloride for injection;
6. add to vial A;
7. add 0.5 mL of Solution B (Cysteine in HCl) (see note below);
8. remove 5 ml of air to prevent pressure build up (this can be done with each syringe additon instead of at the end);
9. place in boiling water bath for 8–10 minutes;
10. Remove from water and add 2.5 mL of Solution C (phosphate buffer);
11. Agitate the vial and cool. Calibrate and perform q.c. on final product. Store final product at room temp and agitate again before use Radiochemical Purity and Stability of Colloids The radiochemical purity (RCP) of the colloids was performed with the use of ITLC-SG chromatography paper as the stationary phase and MEK and saline as the mobile phases. A comparison of the RCP obtained for MEK and saline sheds light on the chemical nature of any impurities present. The shielded radiolabeled products were shaken well before withdrawal of the colloid sample from the vial with a 1 cc syringe and a 22-guage needle. The sample was applied at the origin (3 cm from the bottom of the chromatography strip) and the paper strip was placed in a chromatography chamber. Samples were allowed to run 10 cm, after which they were dried in air at room temperature. The strips were analyzed using a Shimadzu Chromatopac™ thin layer chromatogram scanner to determine the % of radioactivity remaining at the origin and that migrating to the solvent front. The acceptable RCP limit for the colloidal products was arbitrarily set at 95% (for products that were not primarily retained on a 0.22 μm filter). Comparing the RCP values obtained at 0 and 6 hours post-production assessed the sample's in vitro stability.

Size Evaluation of Radiolabeled Colloids

The radioactive particle size distribution of the colloids was evaluated by membrane filtration with hydrophilic polyvinylidene fluoride micropore filters (Millipore™). 13 mm in diameter with pore sizes of 0.1, 0.22 and 0.45 μm. After a 0.2 ml aliquot of the colloid was withdrawn into a 1 cc syringe, the needle from the syringe was carefully removed and the syringe was attached to the female Luer-Lok™ inlet end of a filter. The percentage of radioactivity retained on the filter was expressed as a percentage of the total activity (i.e., filter+filtrate). Filtering was performed 1, 6 and 24 hours after production in order to determine any temporal changes in particle characteristics.

Biokinetics for Example 1

Biodistribution studies of the radiocolloids prepared were conducted in mature CD-1 Swiss white mice weighing approximately 25–30 g. An aliquot containing 2 μCi $^{99m}$Tc was injected into the tail vein of the animals which were euthanized (via $CO_2$/cervical dislocation) 20 minutes post injection. The organs (blood, lung, liver, spleen, sternum, femur and in some cases kidney) were quickly removed, made free from adhering tissues and blood then weighed. The radioactivity in each organ was measured and expressed as a percentage of the injected dose per whole organ and per gram.

Lymphoscintigraphy

For example below, typically, male New Zealand white rabbits with body weight of about 3 kg were used. Three of these were used to test the most promising radiopharmaceuticals as determined by the biodistribution data [ReC of the present invention, commercial TSC, sulfur colloid, filtered sulfur colloid prepared by Eshima's method (Eshima, D. et al. (1996) and antimony colloid]. IM injection of Atravet™ followed by 33 mg Ketamine™ and 3.3 mg Xylazin™ per kg body weight induced anesthesia, which was maintained by subsequent IM injections during the course of the experiment. Radiopharmaceuticals were injected intradermally using tuberculin syringes and a 27-guage needle into the web space between the second and third toes in both hind legs, each injectate containing 18–20 MBq activity in a volume of 0.1 ml. The injection sites were massaged for three minutes immediately after injection. Sequential gamma imaging (using 256×256 matrices) from the posterior of the rabbit lying prone on the collimator surface was performed at 0, 5 and 10 minutes post-injection and subsequently at 10 min intervals up to 2 hours by the use of a GE gamma camera connected to a processor. In some cases a 24 hour image was also obtained. The images were archived on optical disc. The in vivo migration of colloid was assessed by drawing regions of interest over the injection site, distal lymphatic channel, popliteal node (the sentinel node in this case), the proximal lymphatic channel, inguinal nodes, right and left kidneys and the remainder of the body (including the liver) at each time point and corrected for decay.

Example 1

Figure 8:
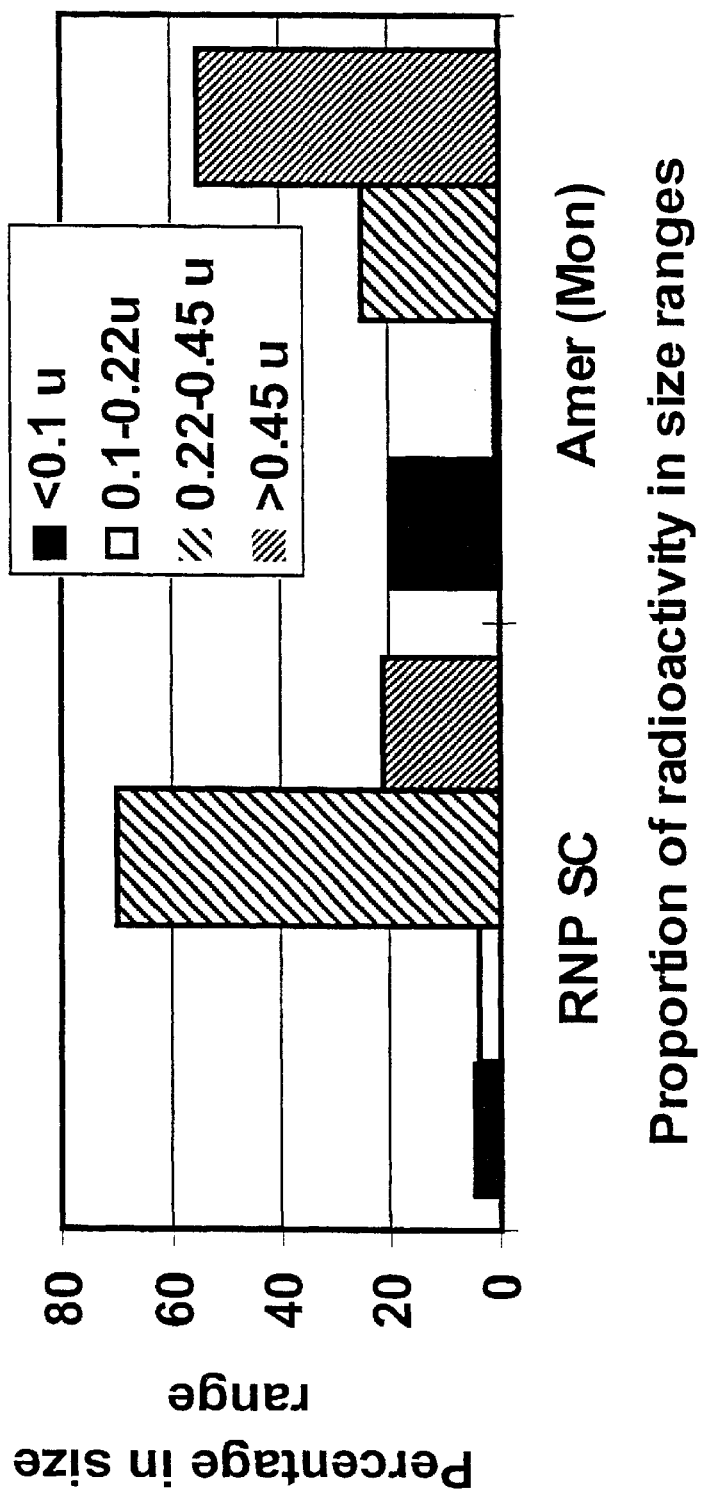
FIG. 8 is a histogram illustrating percentage of sulfur colloid in various size ranges for "in-house" sulfur colloid and Amershan TSC colloid (Monday Te99m elution).

FIG. 1 shows the percentage of retention on a 0.22 $\mu$m filter and the percent RCP for the products tested. Note that larger retention equates to larger particle size for the radioactive colloidal particle. (Consistent with practice in the art, results for the 0.22 $\mu$m filters are discussed here). All of the results including 0.1 and 0.45 $\mu$m filters are compiled in tabular form in Tables 3, 4 and 5. Shown in FIG. 8 is the percentage of sulfur colloid in various size ranges. In particular, FIG. 8 compares results between an in-house sulfur colloid and a commercial product from Amershan.

Figure 15:
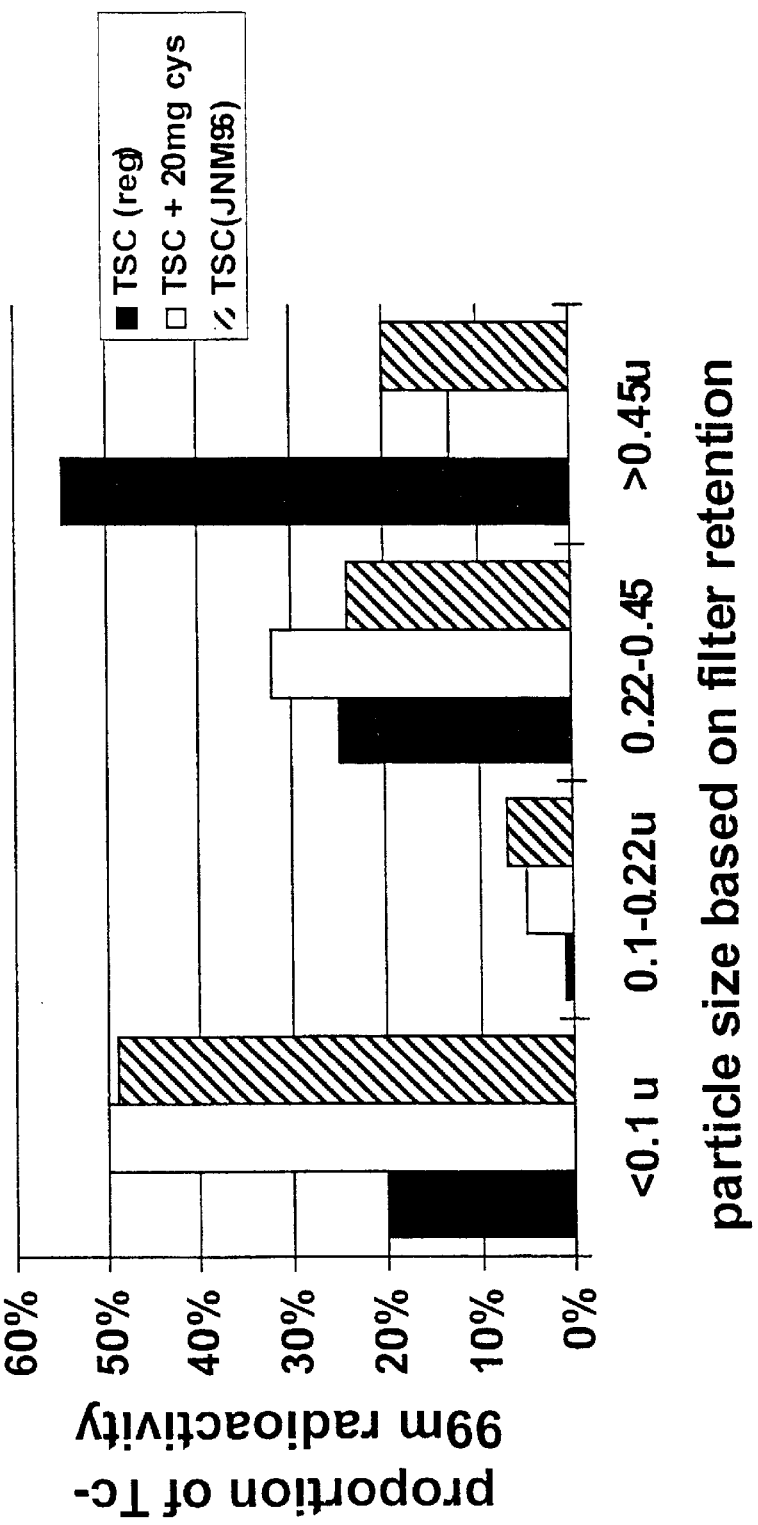
FIG. 15 illustrates particle size distribution of a commercial sulfur colloid under various conditions.

Currently sulfur colloid is the most widely used agent for SNL. Several $^{99m}$Tc—SC preparation variations for lymphoscintigraphic studies have been reported (Alazraki et al. (1997); Alazraki (1998); Albertini et al. (1996); Albertini (1996); Bertil et al. (1969); Eshima et al. (1996); Frier et al. (1981); Frier et al. (1981); Hall et al. (1972); Hauser et al. (1969); Hinkle (1998); Hung et al. (1995); Warbick-Cerone (1986)). In North America many centers used filtered $^{99m}$Tc—sulfur colloid which is performed with a 0.22 $\mu$m filtration, and can be followed by a 0.1 $\mu$m filtration if even smaller particles are desired. FIG. 15 illustrates the variability of particle size (TSC (reg)). As FIG. 1 illustrates on an in-house SC, 91.5% of the radioactivity was retained on a 0.22 $\mu$m filter at 1 hour (and 86.9% at 6 hours post-production, not shown). Thus, despite it's 100% RCP, the wastage of radioactivity means that filtered sulfur colloid is not the ideal agent for SNL. Rather, altering the labeling procedure itself to provide an agent that contains a larger percentage of particles small enough to optimally visualize the lymphatic drainage and yet maintain prolonged retention within the lymph nodes would be a significant improvement (Alazraki et al. (1997)). Adjustments were made as follows: the length of time of boiling and cooling; when the $PO_4^-$ was added (Alazraki et al. (1997); Bertil et al. (1969); Eshima et al. (1996); Frier et al. (1981); Warbick-Cerone (1986)); the volumes of acid added to the thiosulfate solution (Bertil et al. (1969)); the $PO_4^-$ concentration and the length of time since the generator was milked (Alazraki et al. (1997); Eshima et al. (1996)).

Increasing the boiling time increases the RCP and tends to increase the size of the colloid. Raising the pH with addition $[PO^{4-}]$ decreases the particle size and the nature of the elution does not appear to affect final ReC particle size to the extent which could be tested.

Example 2

Figure 2:
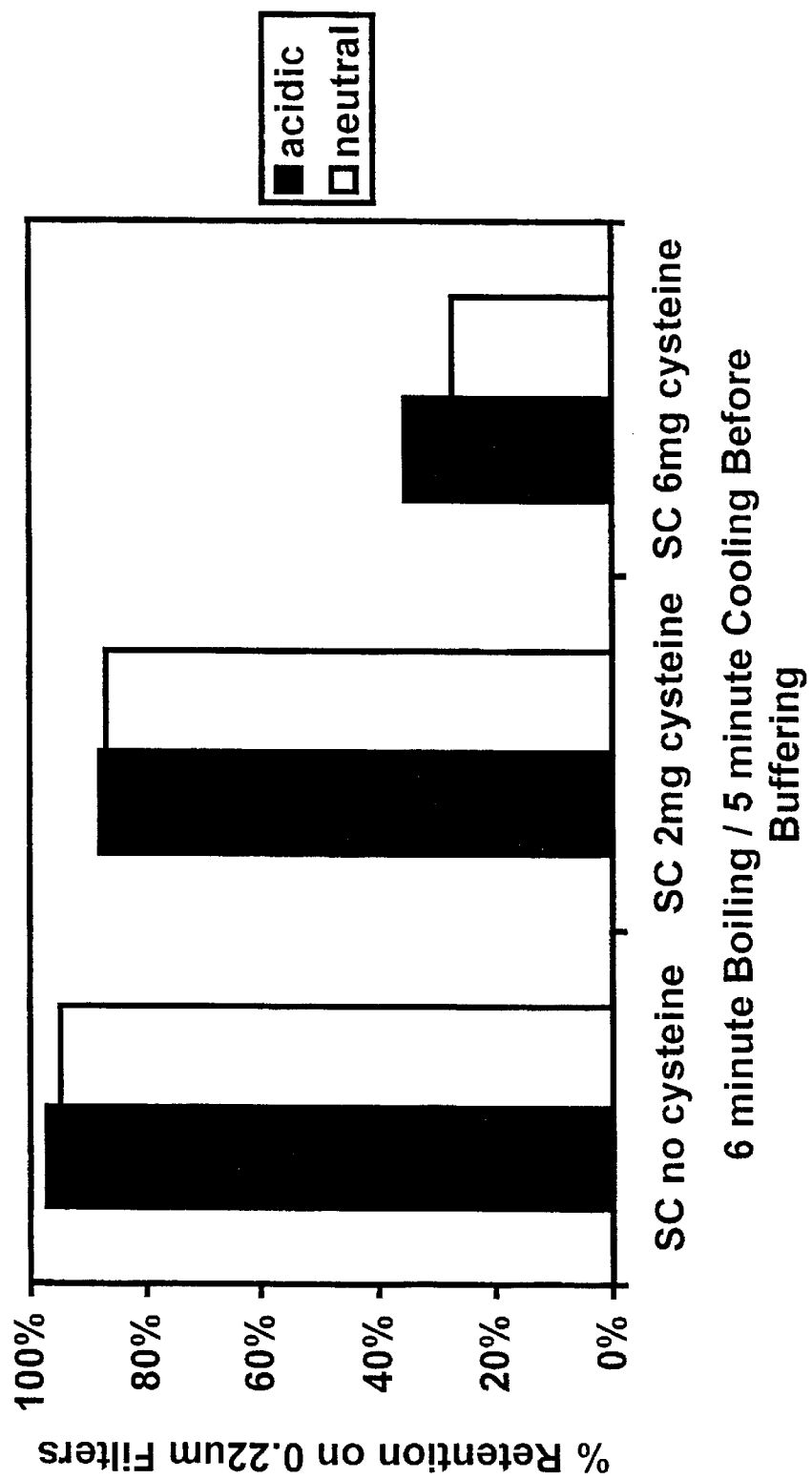
FIG. 2 is a histogram illustrating the effect of increasing amounts of cysteine on retention of sulfur colloid on a 0.22 µm filter.

Elemental sulfur and preformed sulfur colloid are susceptible to attack by —SH groups where the colloid has already been boiled. Inorganic sulfide as well as organic thiols (including cysteine, glutathione, and peptides) will open the S8 ring to form water-soluble polysulfides (Frier et al. (1981)) thus effectively shrinking the sulfur containing particles formed. However, there is minimal effect on the size of the preformed technetium particles. Further, where the preponderance of the colloid generating solution is a rhenium source, such as perrhenate, it is not clear if the shrinking effect will still be observed. Neither is there any indication of the effect of adding the —SH source before boiling. Accordingly, the addition of cysteine to the reaction mixture at the acidification step before boiling was tested. FIG. 2 illustrates the effect of cysteine on regular SC. In addition, the effect of increased phosphate buffer ("neutral") was compared with regular quantities("acidic") based on Steigman et al.'s (Steigman et al. (1986)) finding of smaller particles at higher pH. 2 mg cysteine did not result in a significant decrease in size from the original SC preparation. However 6 mg cysteine dramatically reduced the particle size obtained. The increased $PO_4^-$ slightly reduced the resultant particle size, but in all cases the RCP remained at 100%.

Example 3

Figure 11:
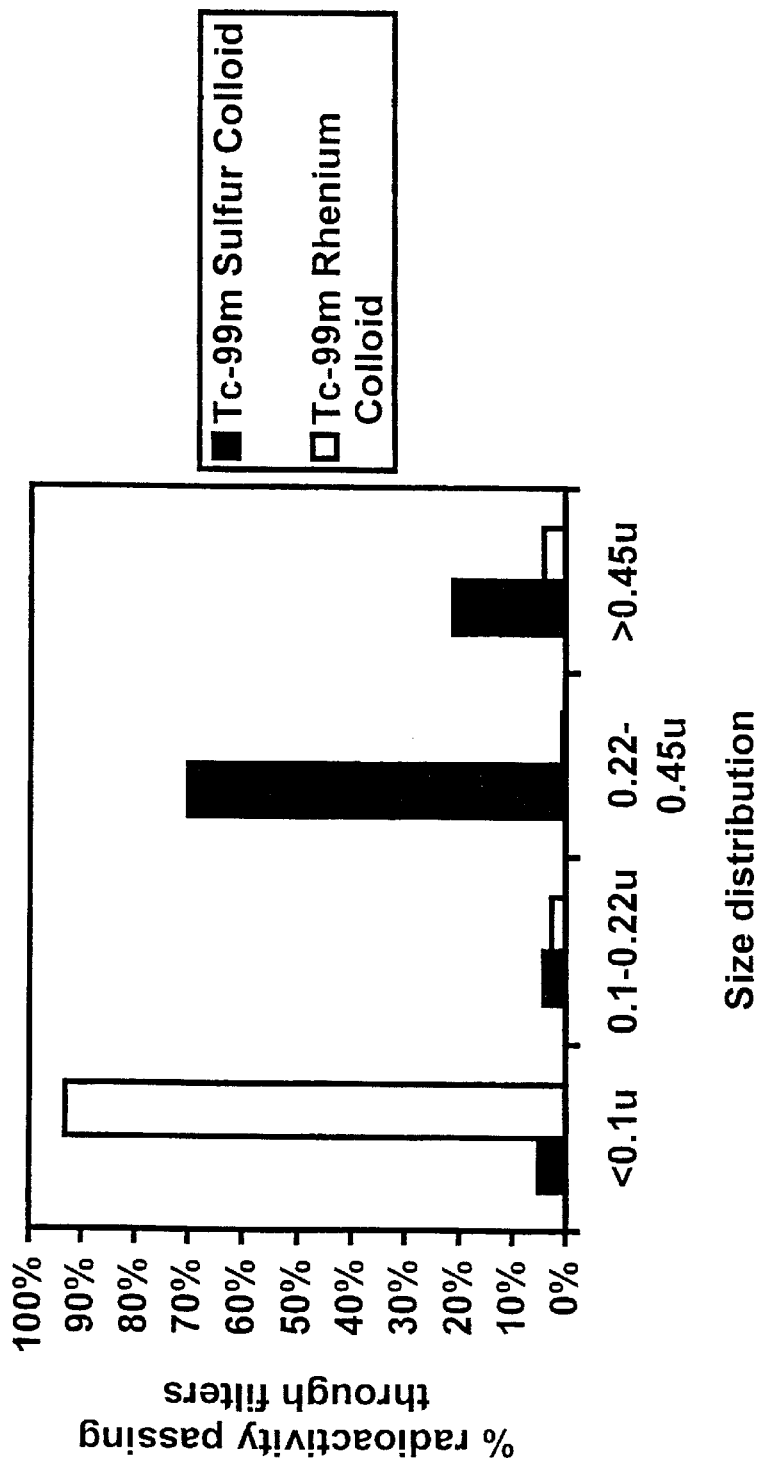
FIG. 11 is a histogram depicting the size distribution of radioactivity comparing "in-house" sulfur colloid with rhenium colloid.

From an initial in-house sulfur colloid next were tried two different ratios of thiosulfate (sulfur source for larger particles) and perrhenate (rhenium source, chemically similar to pertechnetate-$^{99m}$Tc) based on Hung et al.'s (Hung et al. (1995)) finding on smaller particles with higher concentrations of technetium chemical pertechnetate. An initial investigation revealed that rhenium (without any thiosulfate in the organic solution) had 0% RCP—essentially no labeled colloid was formed. Thus a solution was prepared and labelled that contained $\frac{1}{3}^{rd}$ 4.5 mg the amount of the original thiosulfate but the same amount of perrhenate. For simplicity it will be referred to as rhenium colloid (ReC). It is also referred to in the figures as Tc-99m Rhenium Colloid. Without additional cysteine, the 0.22 $\mu$ filter retention at 1 hour of the rhenium colloid at acidic pH, 48.3% (FIG. 3), was about half of that observed for SC (FIG. 2). The much smaller particle size of Re colloid, 26% (FIG. 3), was even more evident at neutral pH (SC 94% retention FIG. 2). A comparison of the size distribution for SC and ReC is provided in FIG. 11.

Example 4

Figure 3:
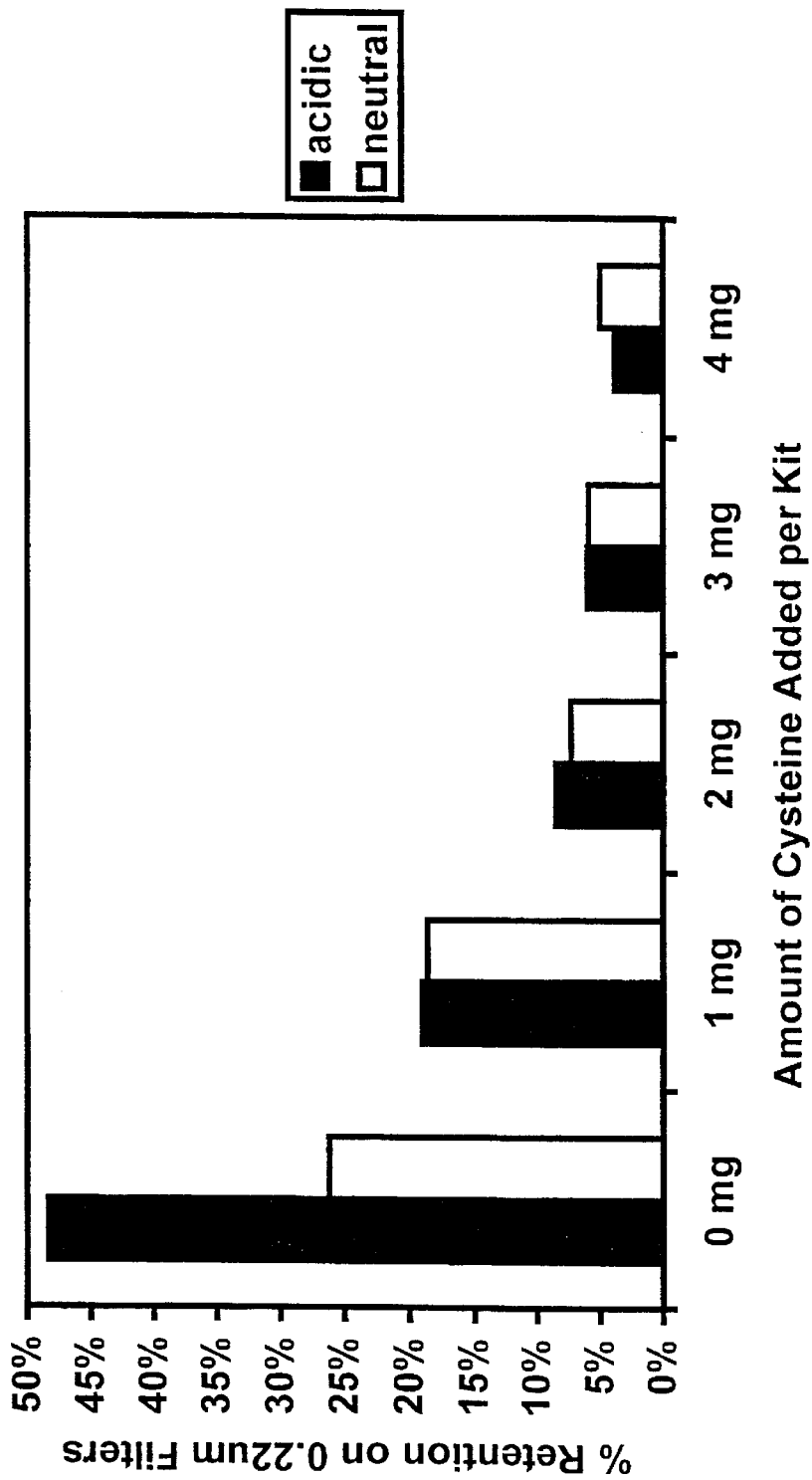
FIG. 3 is a histogram illustrating the effect of the added cysteine on particle size of rhenium colloid.
Figure 9:
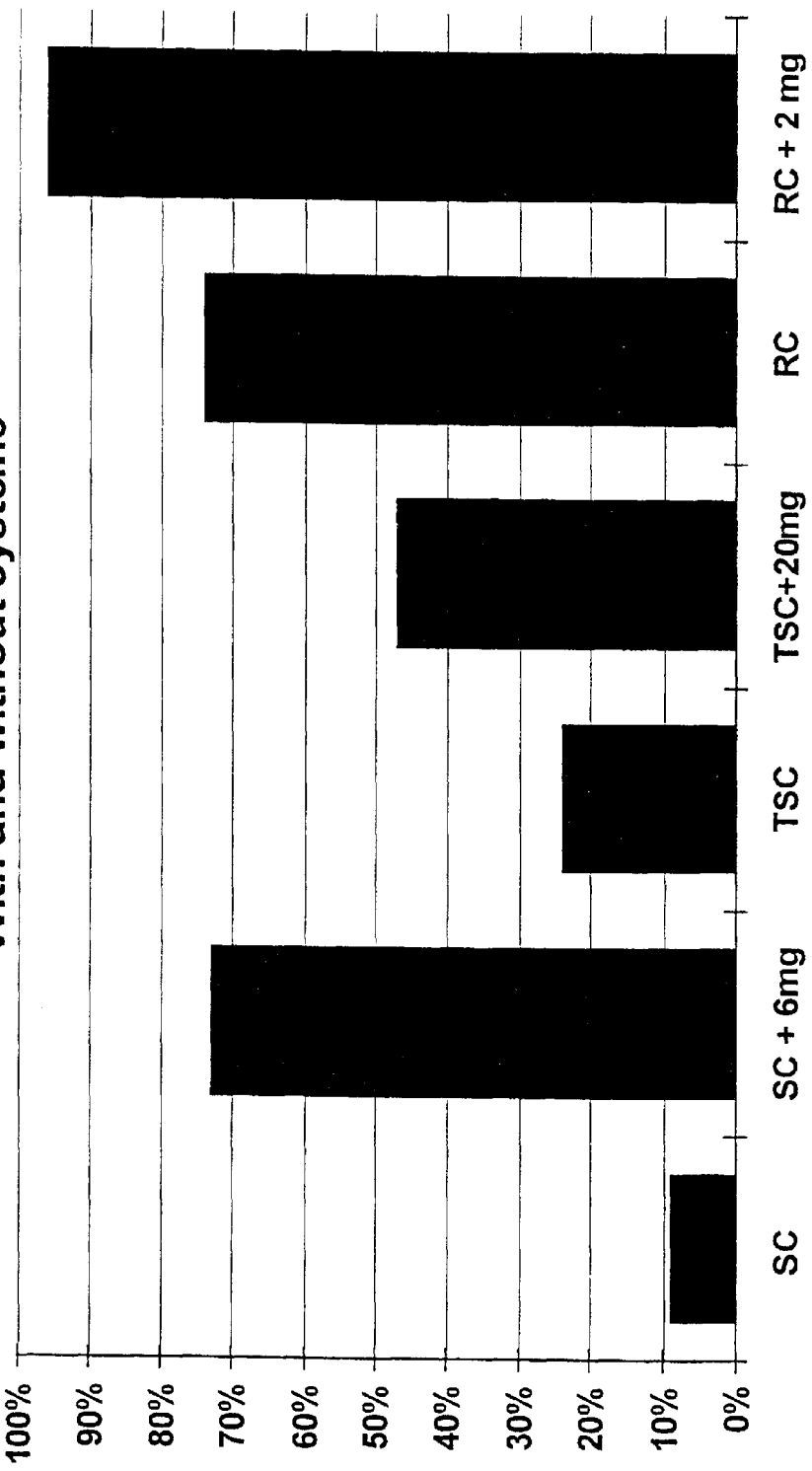
FIG. 9 is a histogram illustrating the percentage of colloid smaller than 0.22 microns for three preparations of colloid, with and without cysteine.
Figure 10:
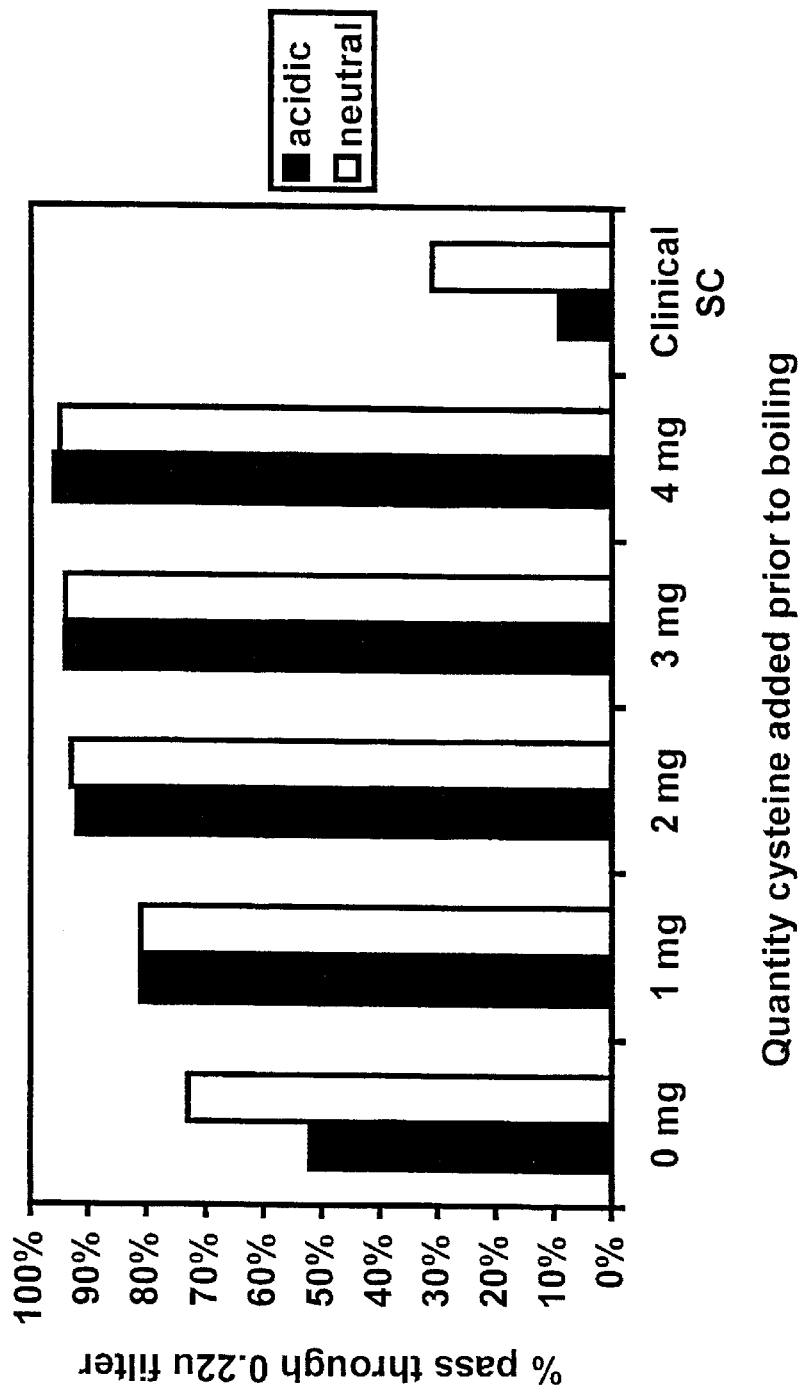
FIG. 10 is a histogram illustrating the effect of cysteine addition, before boiling, on the percentage of colloid particles less than 0.22 microns for rhenium colloid versus clinical "in-house" sulfur colloid.
Figure 16:
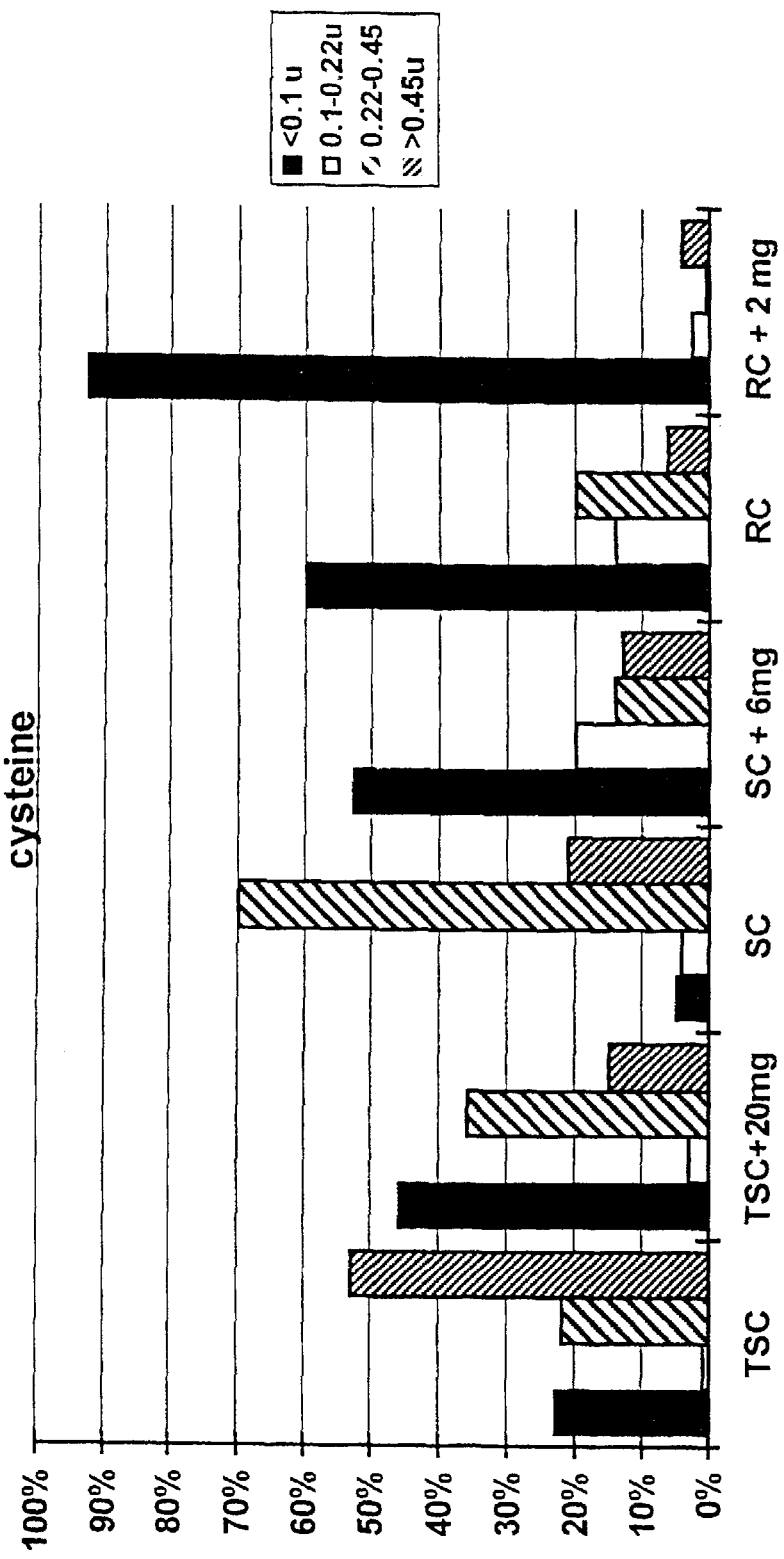
FIG. 16 is a histogram illustrating size distribution of three colloid preparations with and without cysteine.
Figure 17:
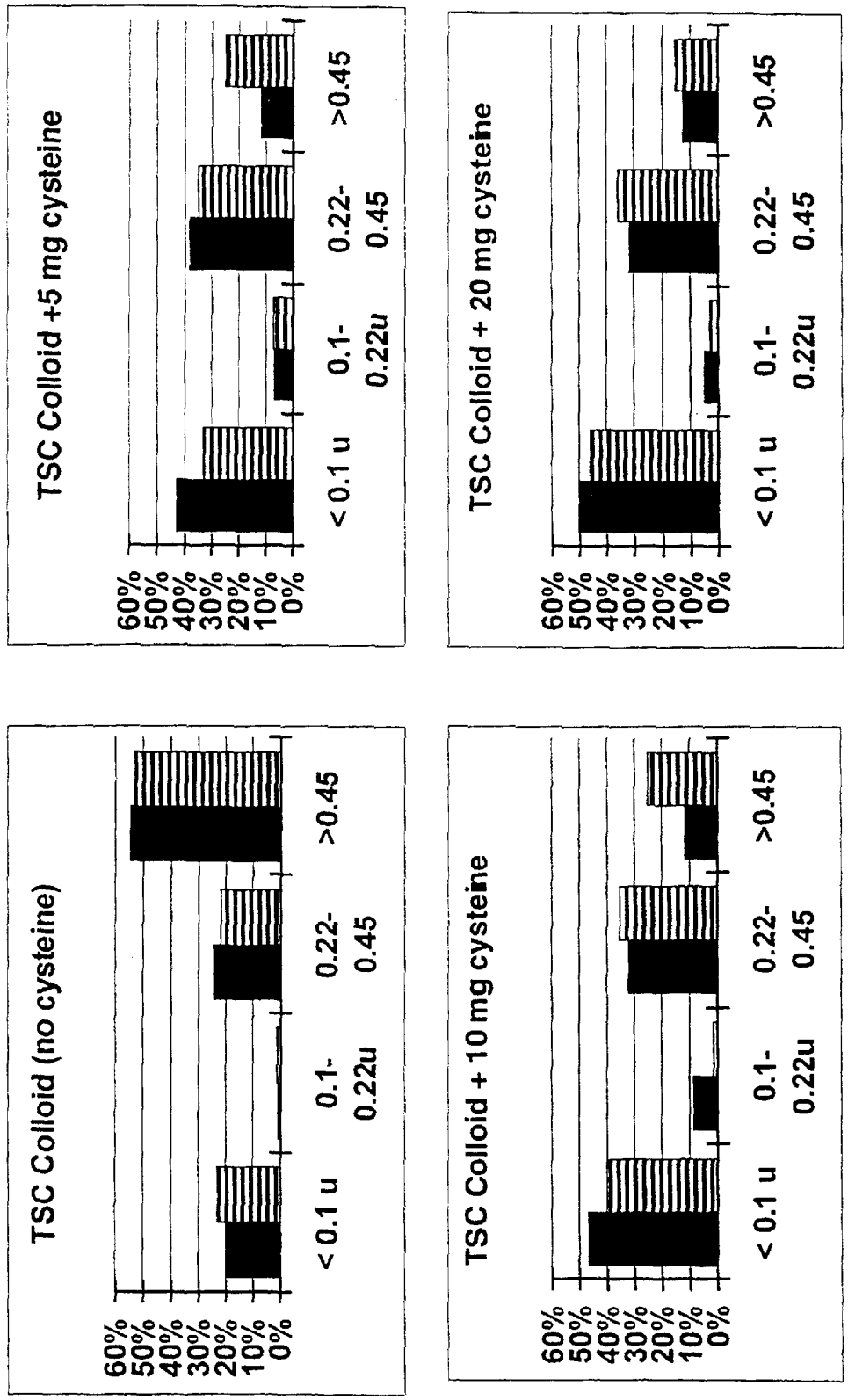
FIG. 17 is four histograms illustrating size distribution of TSC colloid with increasing amounts of cysteine.

Several experiments were performed in which the concentration of cysteine was altered as were the length of time boiling and cooling and the concentrations of $PO^{4-}$ and HCl. Relatively small quantities of cysteine added to ReC cause a significant decrease in the % retention to 4.7% at 1 hr and 5.0% at 6 hours (FIG. 3). Of interest is the fact that the extra $PO^{4-}$ buffer results in differences in retention in ReC without cysteine, but this difference is no longer detectible with 0.22 $\mu$m detection analysis when cysteine is present in the reaction mixture. We have provided a visual comparison of results with cysteine for SC and ReC (FIG. 10) and we have compared the effects of cysteine to the commercial preparation TSC (see FIGS. 9 and 16). As may be seen, overall the ReC prepared with cysteine before boiling generated the highest yield of particle size less than 0.1 micron. However, significantly, addition of cysteine before boiling provided an improved smaller particle size also in the SC as well as the commercial TSC (see FIG. 15 TSC+20 mg cys and FIG. 17 for effect of increasing amounts of cysteine on TSC).

Figure 4:
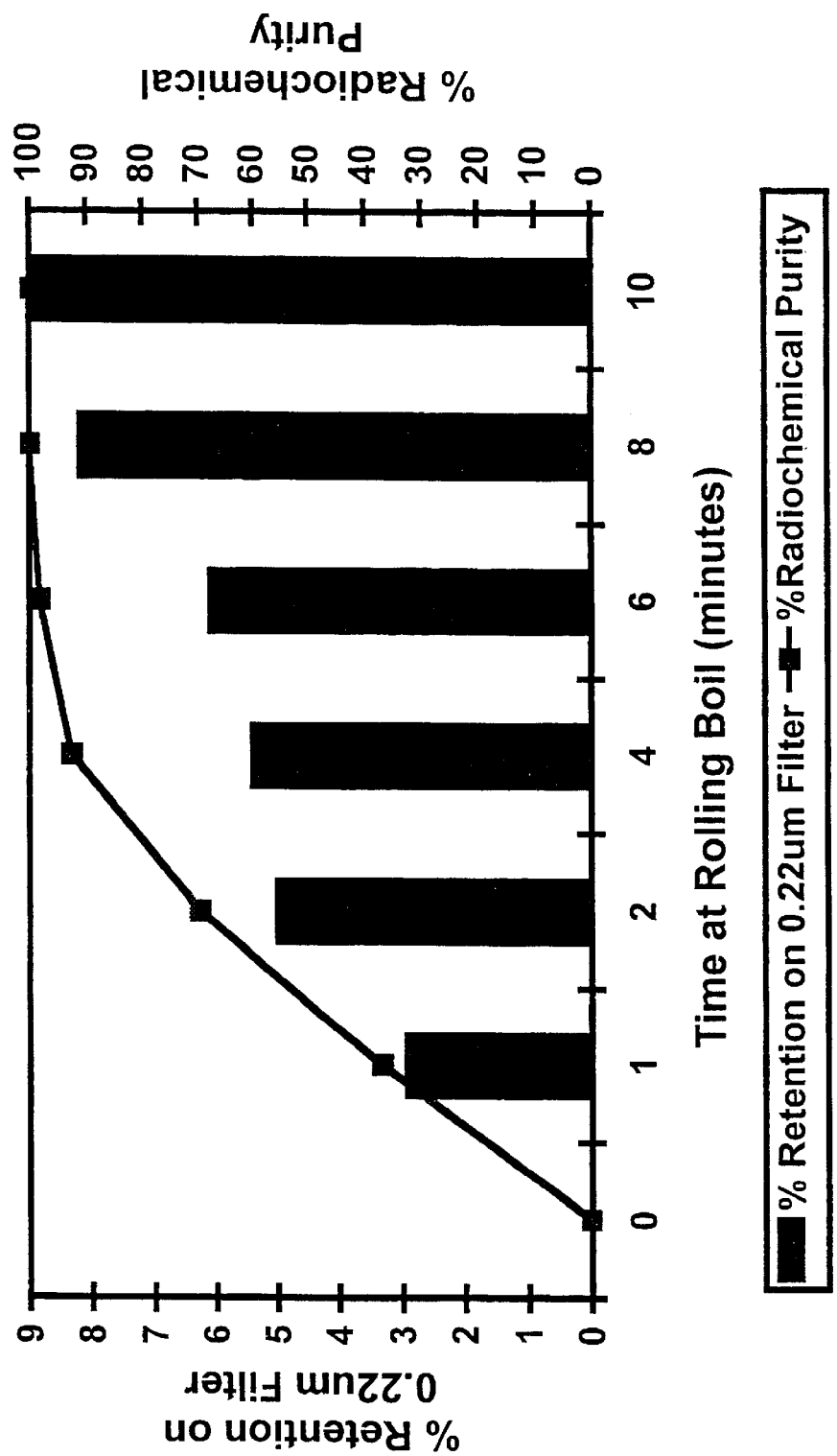
FIG. 4 illustrates the kinetics of boiling time for rhenium colloid.

FIG. 4 demonstrates the % retention and RCP as a function of length of time boiling. Note that as the boiling time increases the labeling efficiency approaches 100% (see FIG. 14) and the retention also increases. From this study it was concluded that a "safe" boiling time in order to ensure efficient labeling was about eight minutes. Further studies revealed that with cysteine the cooling period did not have a significant effect on the ReC particle sizes obtained by 0.1 $\mu$m or 0.22 $\mu$m filtration analysis. In the upper half of Table 2, for simple comparative purposes, the physical results for the in-house SC versus ReC are listed.

Example 5

Next was tested an in-house tin colloid (Ballinger et al. 1993) containing stannous chloride neutralized with phosphate buffer (FIG. 1) and obtained high RCP (100% MEK, 96.3% saline) and very low retention (1.5% and 0.9% at 1 and 6 hours respectively). The ease of preparation (simply adding $^{99m}$Tc and incubating for 15 minutes) was also appealing as it decreases the handling time and thus radiation exposure to the technician preparing it.

For comparative purposes Amerscan Hepatate™ (FIG. 1), a commercially available tin based colloid was prepared. Although its RCP was 100%, almost all the colloid was trapped by the filter (99.0% and 99.2% at 1 and 6 hours). This result demonstrates that the in-house tin colloid product (Ballinger et al. 1993) is significantly unique from that which is currently on the market (Amerscan Hepatate™).

Finally, an antimony colloid kit (FIG. 1) obtained from the Foothills Radiopharmacy in Calgary, Alberta (not readily commercially available) obtained low retention (1.3% at 1 hour) and high RCP (94% MEK and 100% saline). Antimony colloid has been used successfully for general lymphoscintigraphy, but its ability to localize in sentinel nodes has not been firmly established since it appears to migrate passed the sentinel node(s) thereby failing to locate only the sentinel node(s). Lack of commercial availability and a lengthy one hour preparation make it hightly unlikely that it will become widely used unless its imaging capabilities far surpass any of the other colloids.

Particle Size Distribution and Colloidal Shape

Figure 6:
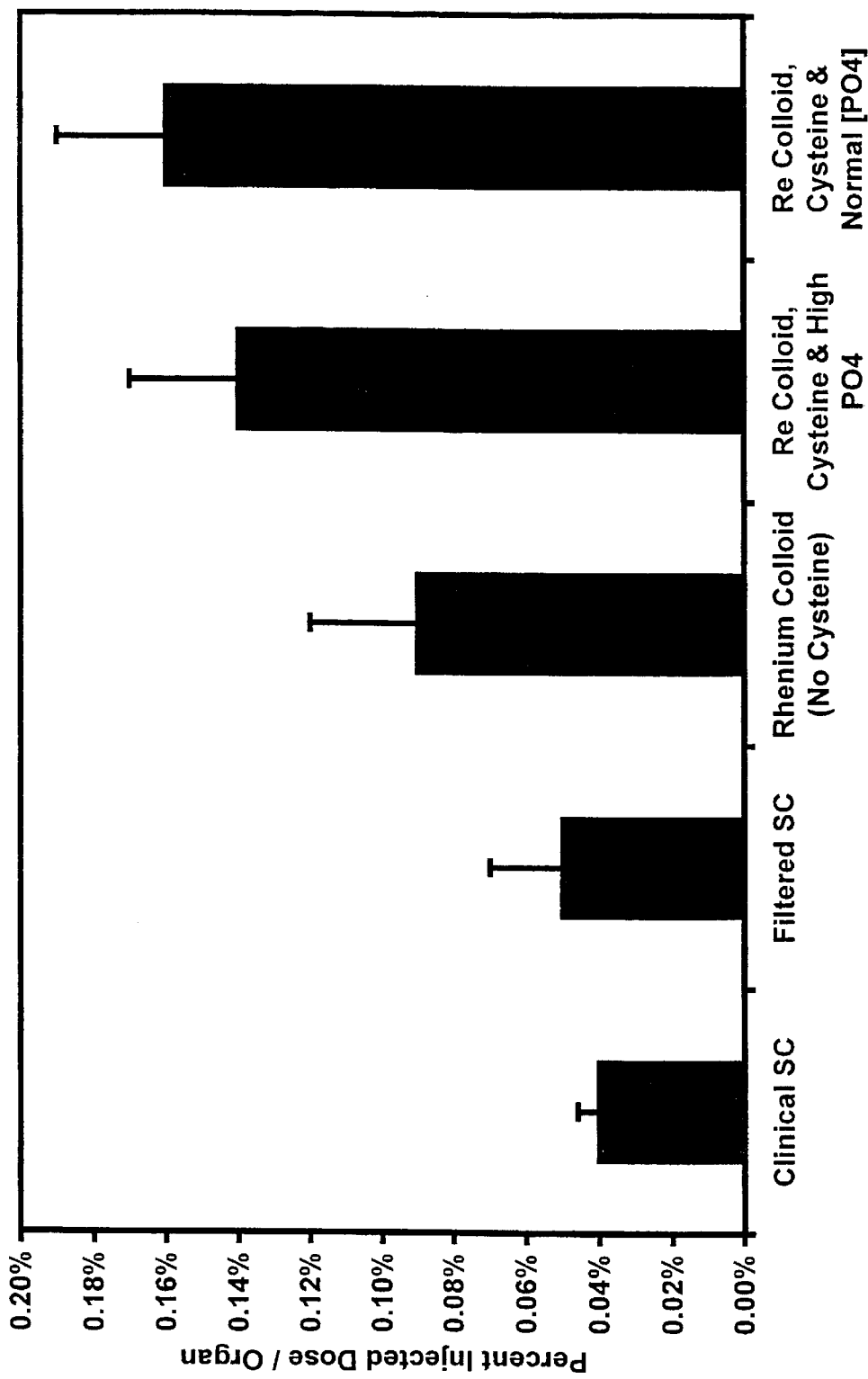
FIG. 6 is a histogram illustrating the percentage uptake of various colloids by the mouse sternum 20 minutes after intravenous injection.

The radioactive size distribution (as determined by filtration) of SC and ReC particles are displayed in FIG. 6. Note that 70% of the SC radioactive particles are within the 0.22–0.45 μm range, while only 6% are less than 0.1 μm in diameter. Compare this with ReC, which has greater than 90% of its particles less than 0.1 μm in diameter. ReC is a novel colloidal preparation and as such the exact size and shape of the particles had to be further characterized. A literature review revealed that transmission electron microscopy is the most appropriate technique (Bergqvist, L. et al. (1983); Ercan, M. et al. (1985); Warbick-Cerone, A. (1986)). The mean diameter of the acidic product was 11.6 nm and that of the neutral was 9.54 nm.

Example 6

Biokinetics

Figure 5:
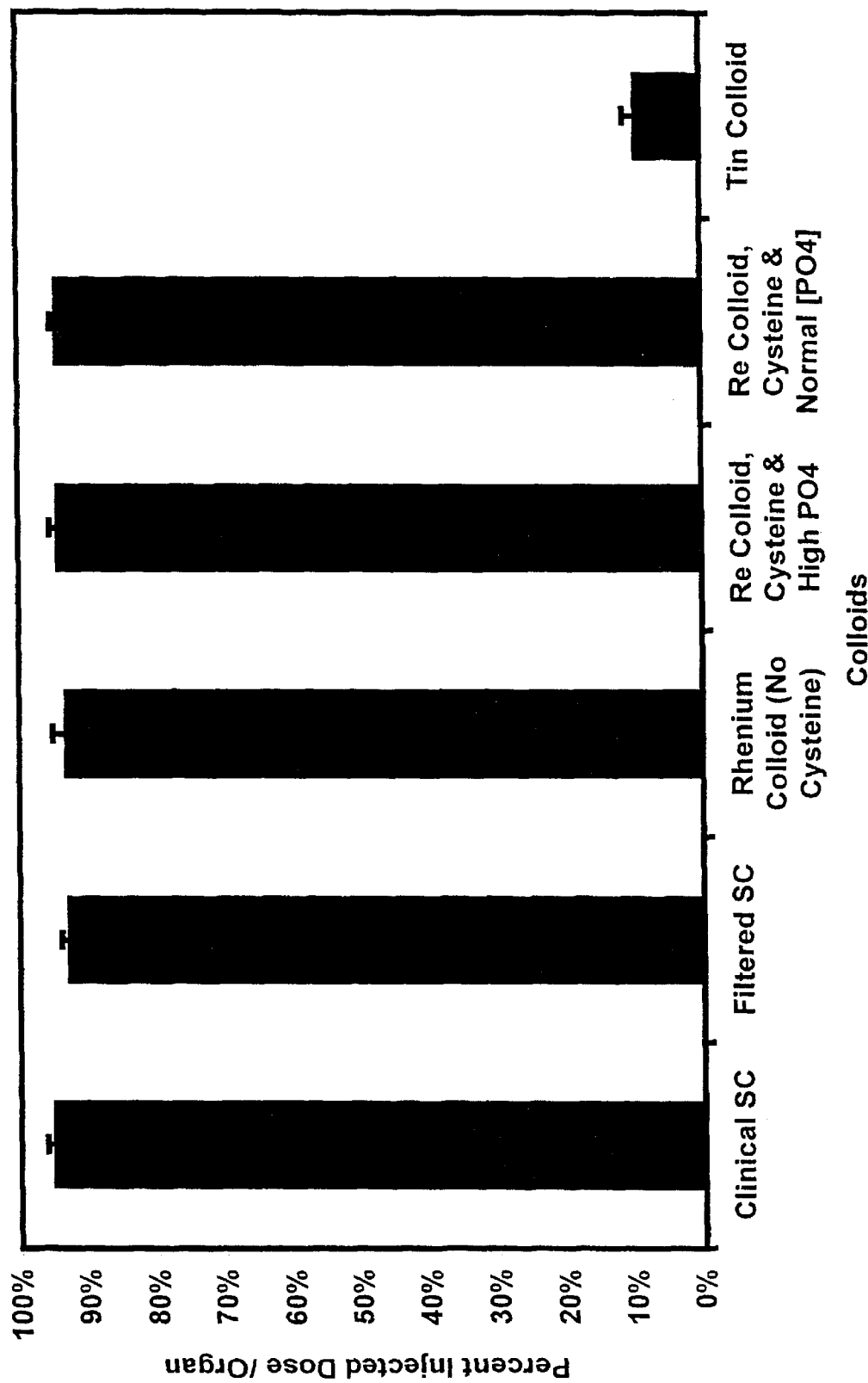
FIG. 5 is a histogram illustrating percentage of the injected dose retained in a mouse liver for various colloids 20 minutes after intravenous injection.
Figure 12:
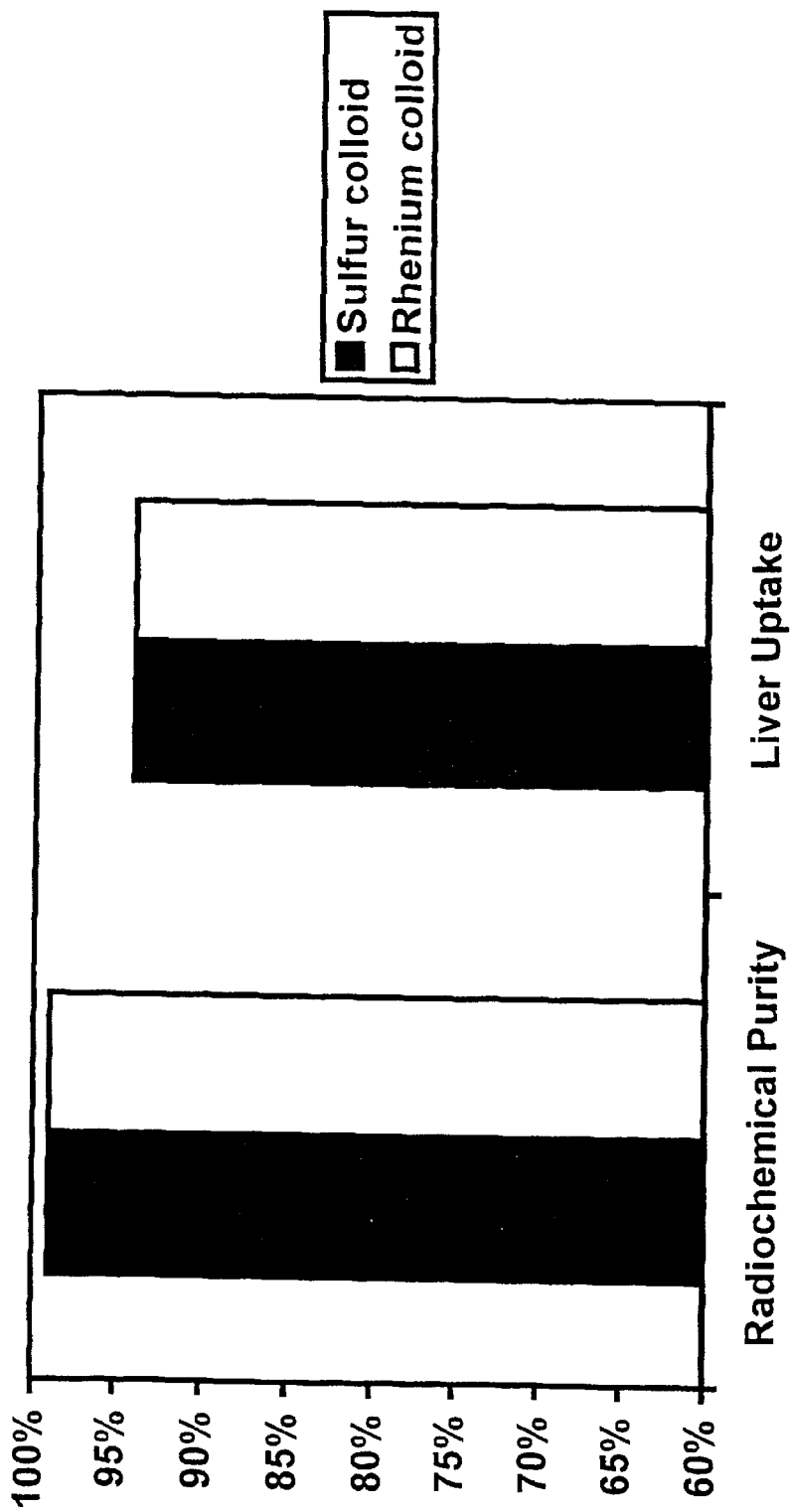
FIG. 12 is a histogram illustrating a comparison of RCP and mouse liver uptake (20 minutes after intravenous injection) between "in-house" sulfur colloid and rhenium colloid.
Figure 13:
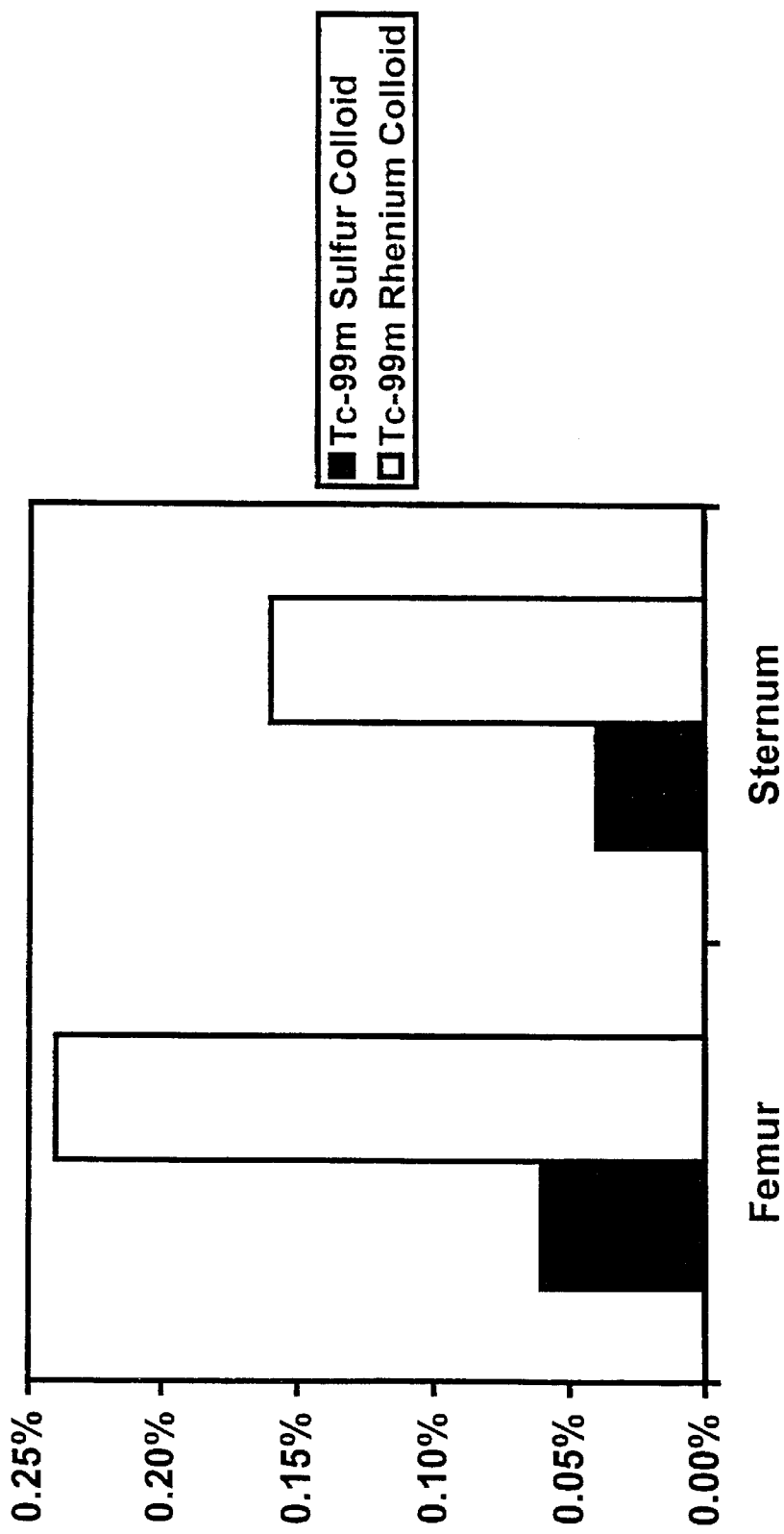
FIG. 13 is a histogram illustrating a comparison of mouse biodistribution 20 minutes after intravenous injection of "in-house" sulfur colloid versus rhenium colloid.

From the initial assessment of these colloids it was concluded that regular SC, filtered SC, ReC (with and without cysteine and normal and high phosphate buffer), and tin colloid were the most promising preparations for use in SNL. Thus, their general biodistribution characteristics were examined in mice 20 minutes after intravenouos injection. FIG. 5 illustrates the % of the injected dose retained in the mouse liver for the various colloids. With the exception of tin colloid the largest percentage of radioactivity is found in the liver. This high retention is due either to the phagocytosis of colloidal particles by the Kupffer cells or their physical entrapment in the Space of Disse (Bennett and Lago (1983); Billinghurst (In Press); Ege et al. (1979); Ercan et al. (1985)). The low uptake of Tin colloid despite particle sizes similar to Re colloid indicates that physical and surface properties also play an important role in uptake and retention in reticuloendothelial cells such as Kupffer cells of the liver. SC's use in liver imaging is based on its rapid and almost total removal from the bloodstream by the liver. Relatively low levels of radioactivity remained in the blood pool for all colloids (0.5–1.5%) except tin (26%, not shown) Ideally, rapid clearance of radioactivity from the blood is desirable as residual activity remaining in the capillaries and veins would interfere with imaging. FIG. 6 demonstrates the % uptake of the colloids by the sternum. Note that the retention of Re with and without cysteine is 34 times higher in the sternum that SC. This result and the fact that SC is used as a bone marrow imaging agent indicates that ReC will also find application in bone marrow imaging. This colloid also has applications in aerosol ventilation studies (see Example 12). For convenience, the lower half of Table 2 provides the in vivo data for SC and ReC, and FIG. 12 provides a histogram comparison of SC and ReC purity and liver uptake. In FIG. 13, the biodistribution of Tc sulfur versus ReC is shown in respect of the femur and sternum. Full data are presented in Table 6.

Example 7

Figure 7:
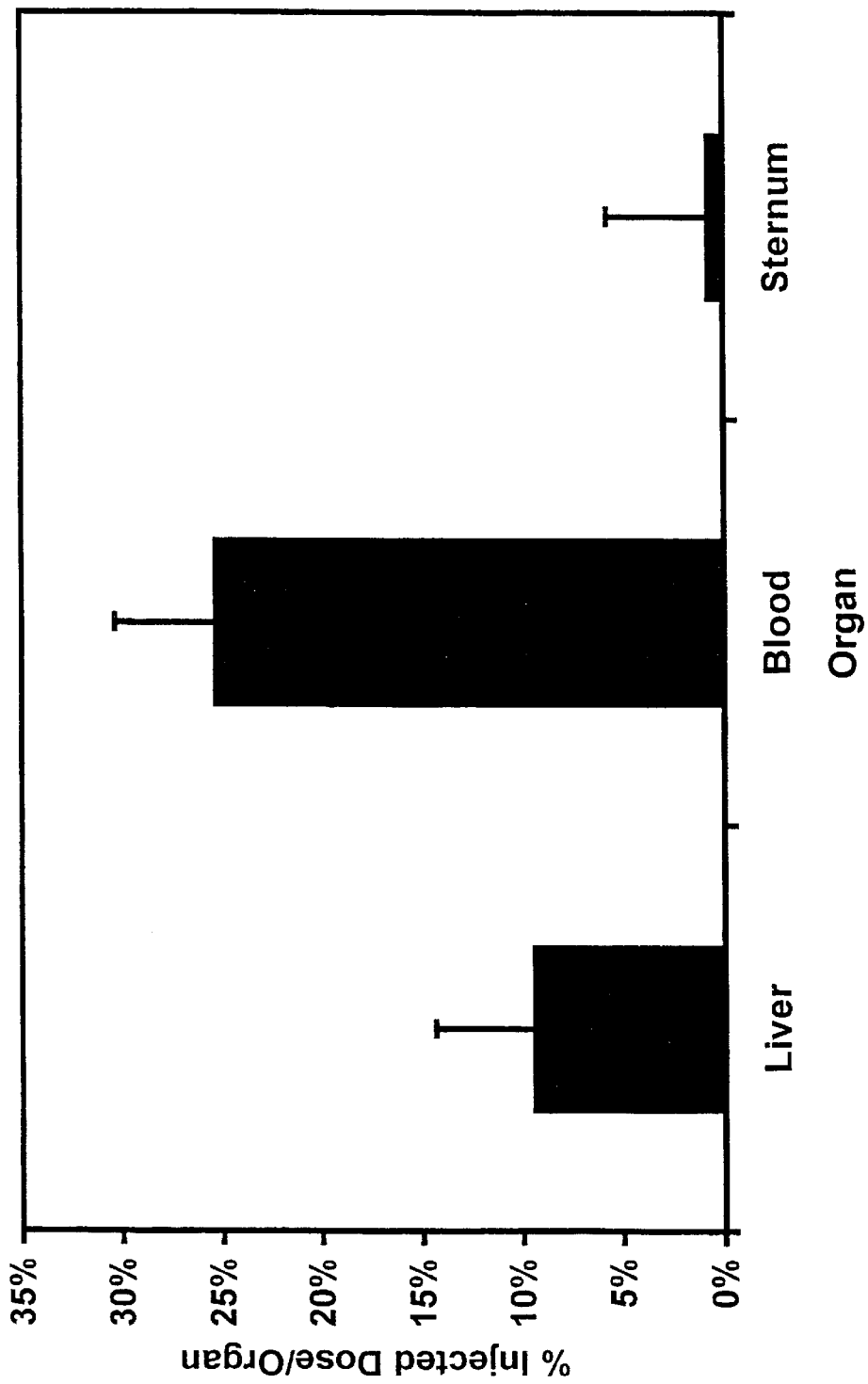
FIG. 7 is a histogram illustrating the biokinetics of tin colloid in mice 20 minutes after intravenous injection.

The biodistribution data for tin colloid (Ballinger et al. 1993) is displayed in FIG. 7. Despite its small size tin colloid achieved very slow clearance from the blood pool and relatively little uptake by the liver. A number of factors may account for the unusual in vivo behavior of tin colloid. It is thought that the chemical nature of the colloid may play and important role, with preferential phagocytosis of different colloids. Perhaps the gelatin coating of both Re and Sulfur Colloids result in better coating with plasma opsonins that aid in recognition and phagocytosis by reticuloendothelial cells of the liver, spleen and bone marrow.

Example 8

Lymphoscintigraphy Studies

Figure 18:
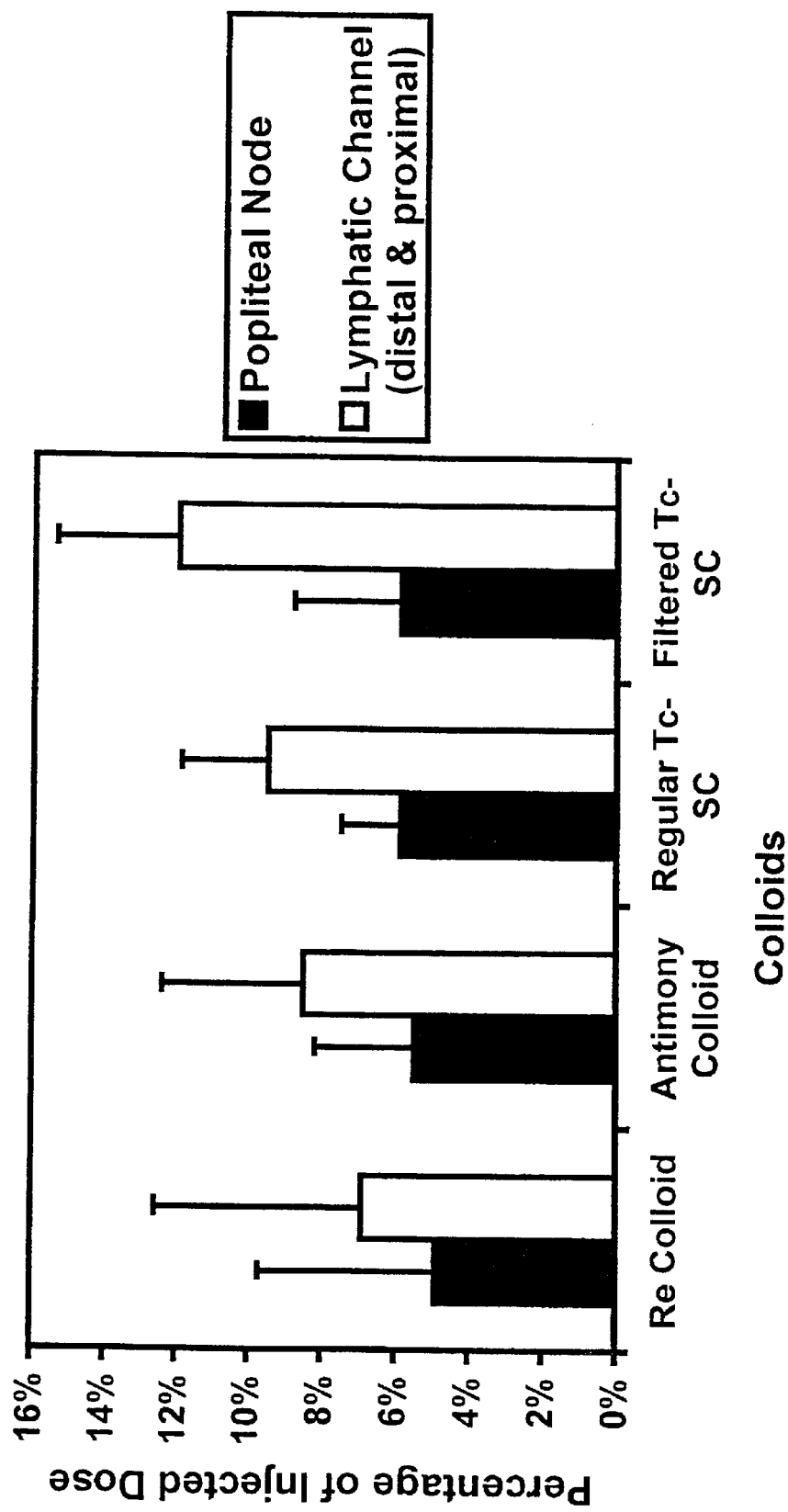
FIG. 18 is a histogram illustrating the percentage of injected dose after one hour of migration of radioactivity from intradermal injection site in a rabbit.

These studies were conducted in rabbits. FIG. 18 shows the percentage of radioactivity (RA) of the injected dose that has migrated to the popliteal node and to the lymphatic channels of the lower limb. The clearance of RA from the injection site in rabbits varied between 13.1% for ReC to 25.3% for filtered TcSC. The retention of ReC localized in the popliteal node is not significantly different from the other colloids tested. The higher percentage of RA in the lymphatic channels of Eshima's filtered sulfur colloid and lack of preferential retention in the sentinel (popliteal) node may be disadvantageous. Ideally one wants some RA in the lymphatic channels, however not enough that it will obscure the imaging of the sentinel node.

Additionally ReC had the lowest percentage of RA localized to the kidneys and urinary bladder [0.17±0.05% compared with Tc99mSC (0.46±0.10%), filtered TCSC (1.38±0.32%) and antimony (0.58±0.21%)], and the remainder of the body including the liver [(1.12±0.23% compared with Tc99mSC (1.71±0.52%), filtered TcSC (4.9±0.5%) and antimony (2.36±0.43%)] at two hours. This indicates that ReC remains in the lymphatic system for a longer duration of time than the other colloids before entering the blood pool.

FIG. 19 demonstrates the percentage of radioactivity at the injection site (top graph (19A)), distal lymphatic channel, popliteal node and proximal channel (bottom graph (19B)) for ReC for two hours following ID injection. The popliteal node is visualized within the first five minutes and the percentage of RA remaining in this sentinel node remains relatively stable for the two hour time period. In fact, 24 hour images revealed that the popliteal (as well as the inguinal nodes) are still easily visualizable. This rapid visualization of the sentinel node and the extended retention of RA have practical significance—allowing the surgical team a large window of time in which to perform the biopsy.

Example 9

Rabbit Lymphoscintigraphy—Entrapment Ratio

For a sentinel node study, it is important that radiolabelled colloid migrates effectively to the first draining lymph node(s). Ideally the radiocolloid does not migrate substantially into further lymphatic channels and further lymph nodes since it will increase background and lead physicians to believe there is more than just the "appropriate" sentinel node. In order to investigate this, a calculation was performed called the entrapment ratio where:

$$\text{Entrapment ratio} = \frac{\text{counts in first primary lymph node}}{\text{Counts in regions past the primary node}}$$

A higher entrapment ratio is indicative of better trapping within the first node and less "leakage" from that lymph node to regions past it. Accordingly, a higher entrapment ratio would lead to less dissection of "non-sentinel nodes" and thereby result in less morbidity to the patient. In this example a comparison of Tc-99m Rhenium Colloid to Filtered (Eshima) and unfiltered Sulfur Colloid(TSC) and Tc-99m antimony colloid was conducted.

Methods 3 anaesthetized male rabbits (crossover studies) received two 0.1 ml (18 MBq) intradermal foot injections of Tc-99m colloid and were massaged. Sequential images were performed to 2 hours. Regions of interest (ROI) were drawn over injection sites, lymph nodes, lymphatic channels and body organs.

Results

All colloids displayed excellent rapid uptake in popliteal nodes with averages of 5–6% injected dose. Most of the migration occurred within the first 10 minutes post injection.

Figure 20:
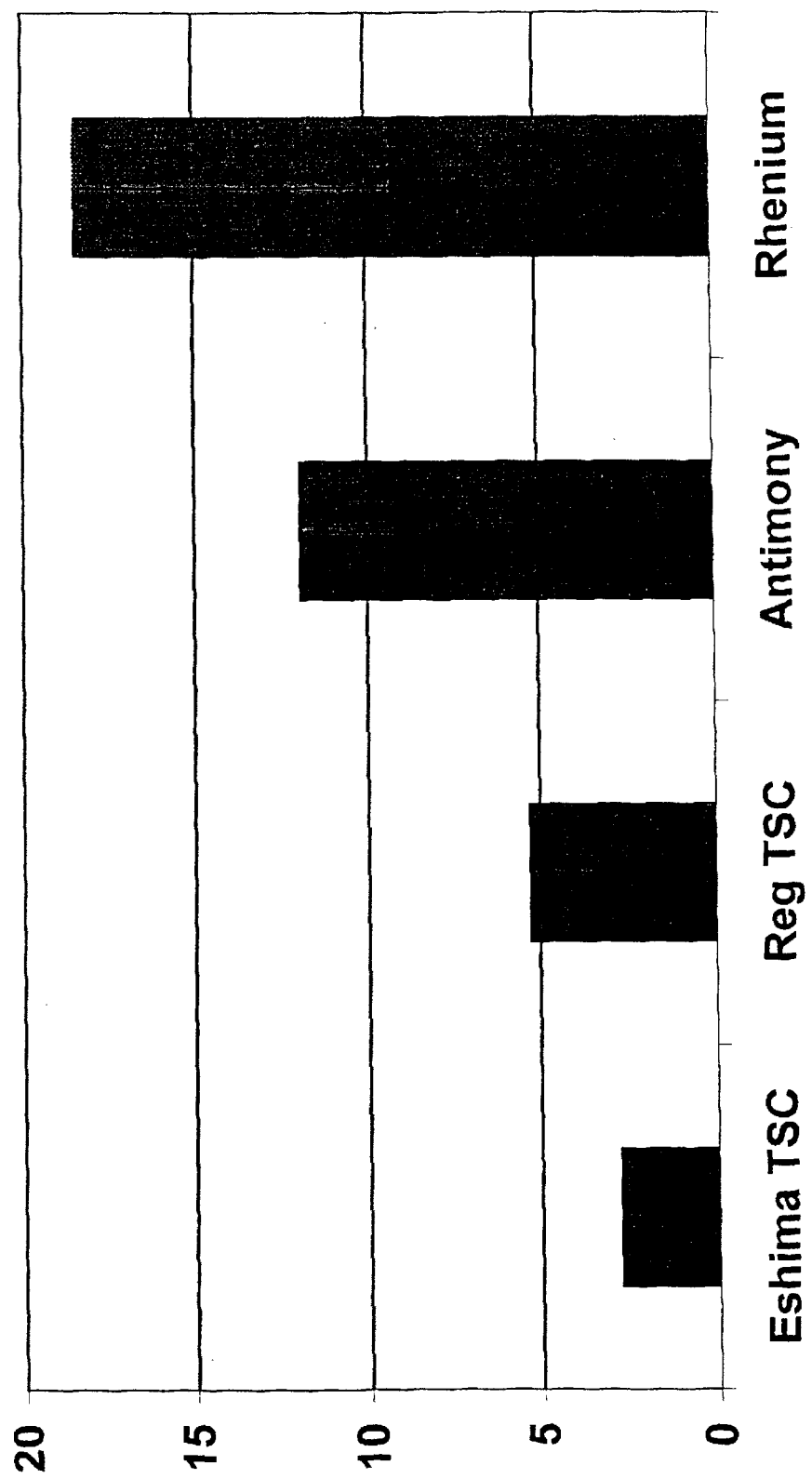
FIG. 20 is a histogram illustrating entrapment ratios of primary popliteal node to efferent lymphatic channels for radio colloids in a rabbit lymphoscintigraphy model at 2 hours.
Figure 21:
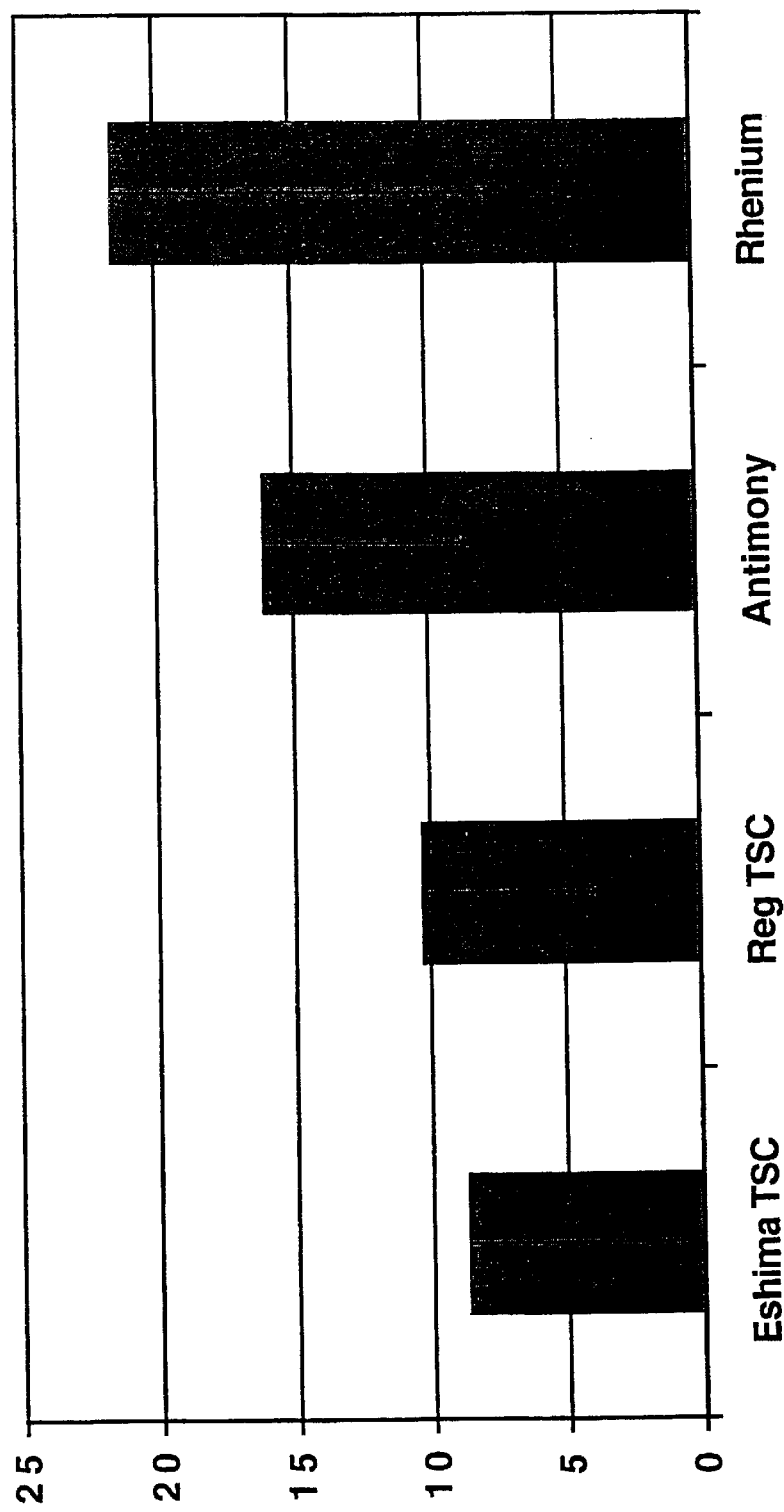
FIG. 21 is a histogram illustrating the ratio of primary node to secondary node entrapment of radio colloids at 2 hours in rabbits.
Figure 22:
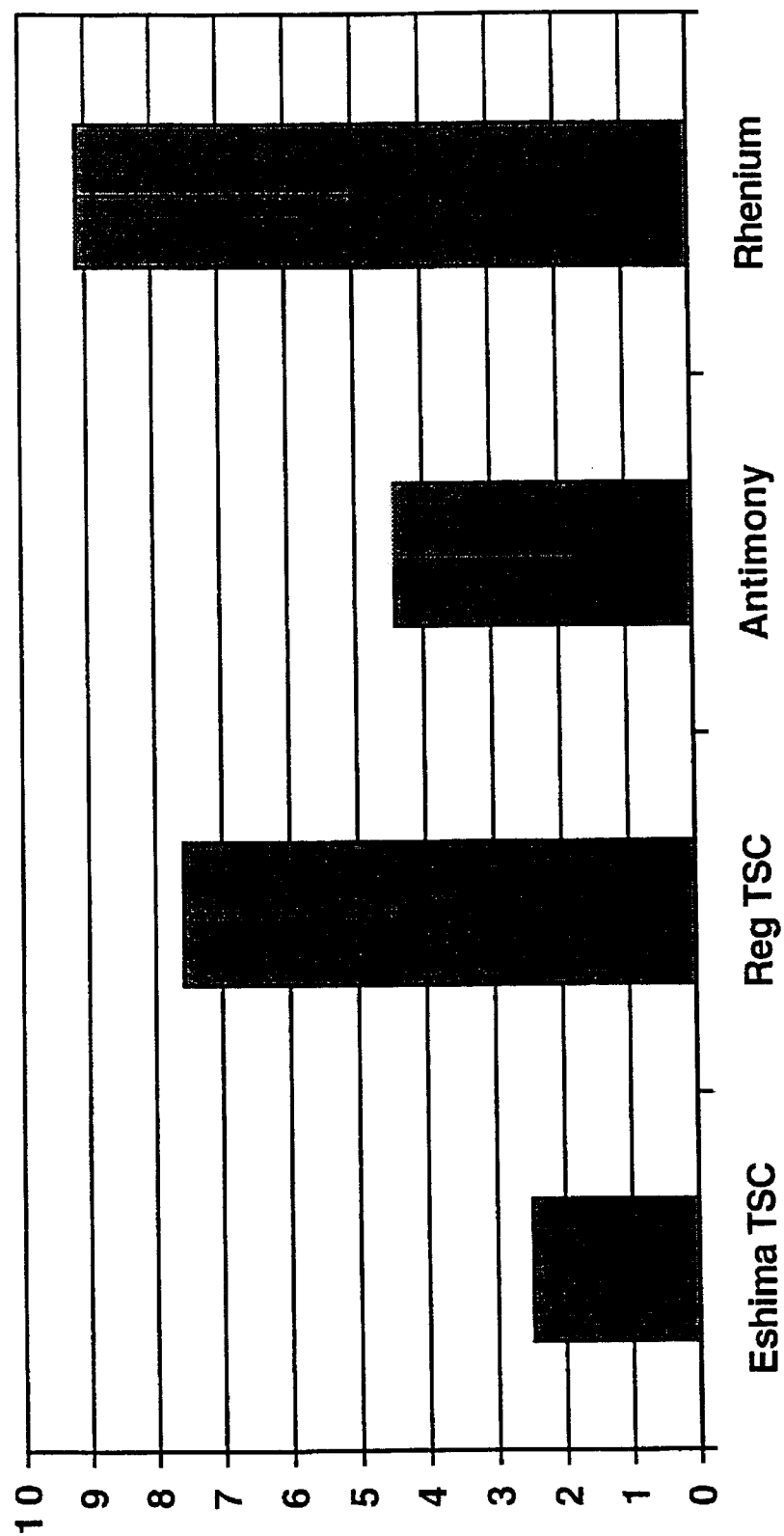
FIG. 22 is a histogram illustrating the ratio of both popliteal nodes to total trunk activity 2 hours post injection in rabbits.

Referring to FIG. 20, the entrapment ratios of popliteal node to efferent lymphatic channel results after 2 hours are illustrated. The results comparing the ratios of primary to secondary nodes are seen in FIG. 21. The ratio of both popliteal nodes to total trunk activity 2 hours after injection are illustrated in FIG. 22. As can be seen, similar trends for colloidal entrapment occurred when comparing popliteal nodes to secondary (inguinal) nodes or body organs. Consequently, it may be concluded that the Tc-99m rhenium colloid of the invention provides superior results.

Example 10

Application of a New Tc-99m Rhenium Colloid for Sentinel Lymph Node Detection in Breast Cancer This example was performed to assess the effectiveness of rhenium colloid of the invention for sentinel lymph node (SLN) localization in breast cancer patients.

Methods

Patients were prospectively injected with Tc-99m rhenium colloid, followed by lymphoscintigraphy and intraoperative gamma probe localization. Vital blue dye was injected intraoperatively. Endpoints: included (1) successful SLN localization by lymphoscintigraphy, (2) successful SLN localization at surgery and (3) blue dye-radiotracer concordance.

Results

Isotope SLN mapping was successful in 98% (46/47). The one mapping failure occurred in a patient with a nonpalpable lesion in which the radiocolloid was injected under ultrasound guidance. The mean number of sentinel nodes was 1.7 (range 1–6). Axillary (vs internal mammary) drainage was identified in 93% of patients. In the cases where both blue dye and radiocolloid were found in the axilla, there was 92% blue dye-isotope concordance (uptake of dye and isotope by the same SLN).

The new Tc-99m rhenium colloid of the present invention is effective in sentinel lymph node mapping for breast cancer. SLN localization was successful in 98% of patients and this is comparable to previous studies utilizing sulfur colloid. The smaller size eliminates the need for filtration and thereby decreases technologist radiation exposure and product losses. A more neutral pH may induce less pain upon injection.

Example 11

Sentinel Node Biopsy in Melanoma Using Tc-99m Rhenium Colloid

In this example, the effectiveness of Tc-99m rhenium colloid of the present invention for sentinel node biopsy in melanoma patients was assessed.

Methods

Consecutive patients with stage 1b or 2 melanoma diagnosed between July 1998 and July 1999 underwent preoperative lymphoscintigraphy. Ten to 15 MBq of Tc-99m rhenium colloid of the invention or, for comparison, filtered sulphur colloid, was injected intradermally about the biopsy scar. Imaging was obtained to localize all draining nodal basins. Intraoperatively, vital blue dye was injected intradermally about the biopsy scar. The gamma probe and blue stained lymphatics aided the dissection. Follow up ranged from 1 to 13 months.

Result 30 patients were enrolled (mean age 55 years, tumor thickness 2.16 mm). Tc-99m sulphur colloid was used in the first 14 patients, and Tc-99m rhenium colloid in the latter 16. A mean of 2.17 nodes were identified preoperatively—2.21 using sulphur colloid, and 2.25 using rhenium colloid (p=0.94). See FIG. 23 which illustrates a typical sentinel node identified in the axilla (middle and top panel). Unpredictable drainage patterns compared with classical lymphatic anatomy occurred in 33% of patients. Localization failed in one patient injected with sulphur colloid, for an overall success rate of 97%. Three patients had a positive sentinel node for occult metastases and underwent completion lymphadenectomy. All patients are alive without disease at 1 to 13 months. Complications from sentinel node biopsy occurred in 6 patients (2 seromas, 2 lymphedema, 1 hematoma, 1 delayed healing).

Example 12

Lung Aerosol Ventilation

Ventilation perfusion scintigraphy can be used to provide images of a subject's lungs. It is usually performed using radioactive gases, but can also be carried out using radio aerosols. Aerosols currently used include Tc99m DTPA but suffer from problems of absorption requiring rapid imaging before absorption. The radiocolloid of the present invention has distinct advantages over such approaches because the smaller colloid provides better penetration into alveoli with less central deposition in the bronchial tree and is not as rapidly absorbed. Accordingly images can be obtained over a longer period after administration without a charge in biodistribution. The methods used to achieve lung inhalation using a radiocolloid of the invention are substantially the same as those described for inhalation of Tc-99m sulfur colloid radioaerosol (see J. Nucl. Med. 24:816–21 (1983); and Vezina et al. Clin. Nucl. Med. 10:759–766 (1985)).

Preliminary results using the colloid are provided in FIG. 24.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Colloids Listed For Assessment |
| --- |
| *Sulfur Colloid * |
| *Sulfur Colloid with Cysteine |
| *Rhenium Colloid |
| *Rhenium Colloid with Cysteine |
| *Tin Colloid |
| *Amerscan Hepatate ™ * |

TABLE 1-continued

| Colloids Listed For Assessment |
| --- |
| *Pentastarch ™ * |
| *Antimony Colloid * |

(* Technetium Kit (Amershan Health))

TABLE 2

| Percentage of Radioactivity | Tc-99m sulfur colloid | Tc-99m "rhenium" colloid |
| --- | --- | --- |
| size < 0.1 u | 5% | 93% |
| size 0.1–0.22 u | 4% | 2.5% |
| size 0.22 u–0.45 u | 70% | 0.5% |
| size > 0.45 u | 21% | 4% |
| radiochemical purity | >98% | >98% |
| liver uptake | 94% | 94% |
| femur uptake | 0.06% | 0.24% |
| sternum uptake | 0.04% | 0.16% |

TABLE 3

| DATE | PRODUCT | pH | 1 hr MEK origin/S.F. | 6 hr MEK origin/S.F. | 1 hr SALINE origin/S.F. |
| --- | --- | --- | --- | --- | --- |
| Wed, Jun. 17, 1998 | Re colloid - sol'n A without thiosulfate - boil 4 min., add C, cool | | 0%/100% | | 0%/100% |
| Wed, Jun. 17, 1998 | Clinical S.C. | | | | |
| Thurs, Jun. 18, 1998 | Reg S.C. | | | | |
| Mon, Jun. 22, 1998 | 2/3 Re 1/3 SC - boil 4 min., add C, cool | | 92.4%/7.6% | 88%/12% (NB mini) | 92.3%/7.6% |
| Mon, Jun. 22, 1998 | 1/3 Re 2/3 SG - boil 4 min., add C, cool | | 98.1%/1.9% | 98%/2% (NB mini) | 98.9%/1.1% |
| Tues, Jun. 23, 1998 | 2/3 Re 1/3 SC - boil 10 min | | | | |
| | (a) immediately add PO4, cool | | n/a | n/a | 100%/0% |
| | (b) wait 2 mins, add PO4, cool | | n/a | n/a | 100%/0% |
| Wed, Jun. 24, 1998 | 2/3 Re 1/3 SC - boil 5 min | | | | |
| | (a) no delay | | 92.0%/8.0% | 90.8%/9.2% | 92.7%/7.3% |
| | (b) 2 min delay | | 91.5%/8.5% | 90.8%/9.2% | 92.2%/7.8% |
| | ⓒ 5 min delay | | 91.3%/8.7% | 91.2%/8.8% | 93.0%/7.0% |
| Thurs, Jun. 25, 1998 | 2/3 Re 1/3 SC - boil 7 min, cool 5 | | | | |
| (reg acid) | (a) 0.5 ml sol'n B, 1.0 ml sol'n C | | 98.0%/2.0% | 100%/0% | 100%/0% |
| (reduced acid) | (b) 0.25 ml sol'n B, 0.39 ml sol'n C | | 49.1%/50.9% | n/a | 51.2%/48.8% |
| | ⓒ add Sn to reduced acid product (b) | | 89%/11% | n/a | 52%/48% |
| Mon, Jun. 29, 1998 | 2/3 Re 1/3 SC -boil 6 min, cool 5, add C | | | | |
| | (a) 0.5 ml sol'n B (HCl) | | 93%/7% | 91.1%/8.9% | 95.7%/4.3% |
| | (b) 0.5 ml SnCl2 (instead of sol'n B) | | 96.5%/3.5% | 96.1%/3.9% | 96.4%/3.6% |
| Mon, Jul. 6, 1998 | Affect of reboiling at slightly basic pH | | | | |
| | (a) Reg SC | 6 | 98.9%/1.1% | 99.2%/0.8% | n/a |
| | (b) 1.5 ml of 1 hr old reg SC, add 1 ml sol'n C and boiled for 4 mins | 8 | 95.7%/1.3% | 98.9%/1.1% (b) 24 hr = 99.4%/0.6% | n/a |
| Tues, Jul. 7, 1998 | Pentastarch Trial | | Acetone 0%/100% | | |
| Tues, Jul. 7, 1998 | Sn Colloid - 3 cc Sn, 0.5 cc TcO4, incubate 15 min. | | 100%/0% | | 96.3%/3.7% |
| Wed, Jul. 8, 1998 | Sn Colloid - 3 cc Sn, 1.5 cc TcO4, incubate 15 min. | | | | |
| | (a) plasma & Sn colloid | | 100%/0% | 100%/0% | n/a |
| | (b) plasma & S.C. | | 100%/0% | 100%/0% | n/a |
| | ⓒ Sn Colloid (NB 24 hr chtgy and filtering on p 59) | | 100%/0% | 100%/0% | 93.8%/6.2% (NB - let dry first) |

TABLE 3-continued

| DATE | PRODUCT | | | |
|---|---|---|---|---|
| Mon, Jul. 13, 1998 | Reg SC - 0.5 ml HCl, 3 ml TcO4, boil 6 min, add 2.5 ml sol'n C, boil 4 more min | 100%/0% | 100%/0% | 100%/0% |
| | 2/3 Re 1/3 SC - 0.5 ml HCl, 3 ml TcO4, boil 6 min, add 2.5 ml sol'n C, boil 4 min | 98.2%/1.8% | 99.6%/0.4% | 98.9%/1.1% |
| Tues, Jul. 14, 1998 | Reg SC - 0.5 cc vial B, boil 4 min, 1 ml C, then cool | 6  100%/0% | 100%/0% | 100%/0% |
| | Amerscan Hepatate II (add 1 GBq qs to 4 cc, shake, incubate 20 min) | 5  100%/0% | 100%/0% | 100%/0% |

| DATE | PRODUCT | 6 hr SALINE origin S.F. | 1 hr 0.1 um | 6 hr 0.1 um | 1 hr 0.22 um |
|---|---|---|---|---|---|
| Wed, Jun. 17, 1998 | Re colloid - sol'n A without thiosulfate - boil 4 min., add C, cool | | | | |
| Wed, Jun. 17, 1998 | Clinical S.C. | | | | |
| Thurs, Jun. 18, 1998 | Reg S.C. | | | | 85.90% |
| Mon, Jun. 22, 1998 | 2/3 Re 1/3 SC - boil 4 min., add C, cool | n/a | | | 36.70% |
| Mon, Jun. 22, 1998 | 1/3 Re 2/3 SG - boil 4 min., add C, cool | n/a | | | 64.10% |
| Tues, Jun. 23, 1998 | 2/3 Re 1/3 SC - boil 10 min | | | | |
| | (a) immediately add PO4, cool | n/a | | | 71% |
| | (b) wait 2 mins, add PO4, cool | n/a | | | 47.20% |
| Wed, Jun. 24, 1998 | 2/3 Re 1/3 SC - boil 5 min | | | | |
| | (a) no delay | n/a | | | 34.30% |
| | (b) 2 min delay | n/a | | | 35.10% |
| | (c) 5 min delay | n/a | | | 30.90% |
| Thurs, Jun. 25, 1998 (reg acid) | 2/3 Re 1/3 SC - boil 7 min, cool 5 (a) 0.5 ml sol'n B, 1.0 ml sol'n C | 100%/0% | | | 83.20% |
| (reduced acid) | (b) 0.25 ml sol'n B, 0.39 ml sol'n C | n/a | | | n/a |
| | (c) add Sn to reduced acid product (b) | n/a | | | n/a |
| Mon, Jun. 29, 1998 | 2/3 Re 1/3 SC -boil 6 min, cool 5, add C | | | | |
| | (a) 0.5 ml sol'n B (HCl) | 94%/6% | | | 41.80% |
| | (b) 0.5 ml SnCl2 (instead of sol'n B) | 96.5%/3.5% | | | 42.70% |
| Mon, Jul. 6, 1998 | Affect of reboiling at slightly basic pH | | | | |
| | (a) Reg SC | n/a | n/a | 88% | 65% |
| | (b) 1.5 ml of 1 hr old reg SC, add 1 ml sol'n C and boiled for 4 mins | n/a | n/a | 83.40% | 30% |
| Tues, Jul. 7, 1998 | Pentastarch Trial | | | | |
| Tues, Jul. 7, 1998 | Sn Colloid - 3 cc Sn, 0.5 cc TcO4, incubate 15 min. | | | | 0.50% |
| Wed, Jul. 8, 1998 | Sn Colloid - 3 cc Sn, 1.5 cc TcO4, incubate 15 min. | | | | |
| | (a) plasma & Sn colloid | n/a | | | |
| | (b) plasma & S.C. | n/a | | | |
| | (c) Sn Colloid (NB 24 hr chtgy and filtering on p 59) | 100%/0% | 1.70% | 1.40% | 1.50% |
| Mon, Jul. 13, 1998 | Reg SC - 0.5 ml HCl, 3 ml TcO4, boil 6 min, add 2.5 ml sol'n C, boil 4 more min | 100%/0% | 91.60% | 91.60% | 44.40% |
| | 2/3 Re 1/3 SC - 0.5 ml HCl, 3 ml TcO4, boil 6 min, add 2.5 ml sol'n C, boil 4 min | 100%/0% | 52.20% | 49% | 26.60% |
| Tues, Jul. 14, 1998 | Reg SC - 0.5 cc vial B, boil 4 min, 1 ml C, then cool | n/a | 89.90% | 90 | 79% |
| | Amerscan Hepatate II (add 1 GBq qs to 4 cc, shake, incubate 20 min) | n/a | 99.50% | 99.7 | 99% |

| DATE | PRODUCT | 6 hr 0.22 um | 1 hr 0.22 um | 6 hr 0.22 um | 1 hr 0.45 um |
|---|---|---|---|---|---|
| Wed, Jun. 17, 1998 | Re colloid - sol'n A without thiosulfate - boil 4 min., add C, cool | | | | |
| Wed, Jun. 17, 1998 | Clinical S.C. | 73% | | | 25.70% |
| Thurs, Jun. 18, 1998 | Reg S.C. | 83.70% | | | 4.20% |
| Mon, Jun. 22, 1998 | 2/3 Re 1/3 SC - boil 4 min., add C, cool | 27.50% | | | |
| Mon, Jun. 22, 1998 | 1/3 Re 2/3 SG - boil 4 min., add C, cool | 62.40% | | | 8.20% |
| Tues, Jun. 23, 1998 | 2/3 Re 1/3 SC - boil 10 min | | | | |
| | (a) immediately add PO4, cool | 81.30% | | | 56% |
| | (b) wait 2 mins, add PO4, cool | 47.10% | | | 38.40% |

TABLE 3-continued

| Date | Description | | | | |
|---|---|---|---|---|---|
| Wed, Jun. 24, 1998 | 2/3 Re 1/3 SC - boil 5 min | | | | |
| | (a) no delay | 35.40% | | | 22.60% |
| | (b) 2 min delay | 20.80% | | | 18.70% |
| | ⓒ 5 min delay | 26.20% | | | 5.70% |
| Thurs, Jun. 25, 1998 | 2/3 Re 1/3 SC - boil 7 min, cool 5 | | | | |
| (reg acid) | (a) 0.5 ml sol'n B, 1.0 ml sol'n C | 60.90% | | | 60.20% |
| (reduced acid) | (b) 0.25 ml sol'n B, 0.39 ml sol'n C | n/a | | | n/a |
| | ⓒ add Sn to reduced acid product(b) | n/a | | | n/a |
| Mon, Jun. 29, 1998 | 2/3 Re 1/3 SC -boil 6 min, cool 5, add C | | | | |
| | (a) 0.5 ml sol'n B (HCl) | 36.30% | | | 23.60% |
| | (b) 0.5 ml SnCl2 (instead of sol'n B) | 40.50% | | | 7.50% |
| Mon, Jul. 6, 1998 | Affect of reboiling at slightly basic pH | 58.90% | n/a | 64.30% | 2.80% |
| | (a) Reg SC | 14% | n/a | 58% | 3.70% |
| | (b) 1.5 ml of 1 hr old reg SC, add 1 ml sol'n C and boiled for 4 mins | (b) 61.8% at 24 hr | | (b) 38% at 24 hr | |
| Tues, Jul. 7, 1998 | Pentastarch Trial | | | | |
| Tues, Jul. 7, 1998 | Sn Colloid - 3 cc Sn, 0.5 cc TcO4, incubate 15 min. | | | | |
| Wed, Jul. 8, 1998 | Sn Colloid - 3 cc Sn, 1.5 cc TcO4, incubate 15 min. (a) plasma & Sn colloid (b) plasma & S.C. | | | | |
| | ⓒ Sn Colloid | 0.90% | 2.30% | 1.50% | 0.80% |
| | (NB 24 hr chtgy and filtering on p 59) | | | | |
| Mon, Jul. 13, 1998 | Reg SC - 0.5 ml HCl, 3 ml TcO4, boil 6 min, add 2.5 ml sol'n C, boil 4 more min | 27.10% | 58.40% | 56% | 5.30% |
| | 2/3 Re 1/3 SC - 0.5 ml HCl, 3 ml TcO4, boil 6 min, add 2.5 ml sol'n C, boil 4 min | 22.80% | 30.90% | 26.60% | 7.40% |
| Tues, Jul. 14, 1998 | Reg SC - 0.5 cc vial B, boil 4 min, 1 ml C, then cool | 62.7 | 85.10% | 72 | 16% |
| | Amerscan Hepatate II (add 1 GBq qs to 4 cc, shake, incubate 20 min) | 99.2 | 99.50% | 99.6% | 91% |

| DATE | PRODUCT | 6 hr 0.45 um | 1 hr 0.45 um | 6 hr 0.45 um |
|---|---|---|---|---|
| Wed, Jun. 17, 1998 | Re colloid - sol'n A without thiosulfate - boil 4 min., add C, cool | 8% | | |
| Wed, Jun. 17, 1998 | Clinical S.C. | | | |
| Thurs, Jun. 18, 1998 | Reg S.C. | 4.60% | | |
| Mon, Jun. 22, 1998 | 2/3 Re 1/3 SC - boil 4 min., add C, cool | 4.30% | | |
| Mon, Jun. 22, 1998 | 1/3 Re 2/3 SG - boil 4 min., add C, cool | 5.80% | | |
| Tues, Jun. 23, 1998 | 2/3 Re 1/3 SC - boil 10 min | | | |
| | (a) immediately add PO4, cool | 66% | | |
| | (b) wait 2 mins, add PO4, cool | 33.60% | | |
| Wed, Jun. 24, 1998 | 2/3 Re 1/3 SC - boil 5 min | | | |
| | (a) no delay | 12.60% | | |
| | (b) 2 min delay | 8.90% | | |
| | ⓒ 5 min delay | 6.90% | | |
| Thurs, Jun. 25, 1998 | 2/3 Re 1/3 SC - boil 7 min, cool 5 | | | |
| (reg acid) | (a) 0.5 ml sol'n B, 1.0 ml sol'n C | 13.60% | | |
| (reduced acid) | (b) 0.25 ml sol'n B, 0.39 ml sol'n C | n/a | | |
| | ⓒ add Sn to reduced acid product(b) | n/a | | |
| Mon, Jun. 29, 1998 | 2/3 Re 1/3 SC -boil 6 min, cool 5, add C | | | |
| | (a) 0.5 ml sol'n B (HCl) | 5.30% | | |
| | (b) 0.5 ml SnCl2 (instead of sol'n B) | 3.10% | | |
| Mon, Jul. 6, 1998 | Affect of reboiling at slightly basic pH | | | |
| | (a) Reg SC | 3.30% | n/a | 4.20% |
| | (b) 1.5 ml of 1 hr old reg SC, add 1 ml sol'n C and boiled for 4 mins | 1.90% | n/a | 7.60% |
| Tues, Jul. 7, 1998 | Pentastarch Trial | | | |
| Tues, Jul. 7, 1998 | Sn Colloid - 3 cc Sn, 0.5 cc TcO4, incubate 15 min. | | | |
| Wed, Jul. 8, 1998 | Sn Colloid - 3 cc Sn, 1.5 cc TcO4, incubate 15 min. (a) plasma & Sn colloid (b) plasma & S.C. | | | |
| | ⓒ Sn Colloid | 0.70% | 1.60% | 1.80% |
| | (NB 24 hr chtgy and filtering on p 59) | | | |
| Mon, Jul. 13, 1998 | Reg SC - 0.5 ml HCl, 3 ml TcO4, boil 6 min, add 2.5 ml sol'n C, boil 4 more min | 5.90% | 4.50% | 6% |
| | 2/3 Re 1/3 SC - 0.5 ml HCl, 3 ml TcO4, boil 6 min, add 2.5 ml sol'n C, boil 4 min | 8.80% | 6.70% | 8.10% |

TABLE 3-continued

| | | | | |
|---|---|---|---|---|
| Tues, Jul. 14, 1998 | Reg SC - 0.5 cc vial B, boil 4 min, 1 ml C, then cool | 8.5 | 9% | 6.6 |
| | Amerscan Hepatate II (add 1 GBq qs to 4 cc, shake, incubate 20 min) | 99.4 | 97 | 99.1 |

TABLE 4

| DATE | PRODUCT | pH | 1 hr MEK origin/S.F. | 6 hr MEK origin/S.F. | 1 hr SALINE origin/S.F. | 6 hr SALINE origin/S.F. |
|---|---|---|---|---|---|---|
| Wed, Jul. 15, 1998 | Reg SC with additional KReO4 - reg SC kit + 1 ml KReO4 + 2 ml TcO4 + 0.5 ml 0.5 NHCl | | | | | |
| | (a) 2.5 ml boiled 6 min + 1.25 ml sol'n C reboil 4 mins | | 100%/0% | 100%/0% | n/a | n/a |
| | (b) 2.5 ml boiled 6 min, cool 5 minutes, and add 0.5 ml sol'n C | | 100%/0% | 100%/0% | n/a | n/a |
| Thurs, Jul. 16, 1998 | Cysteine - 2/3 Re 1/3 SC (1/2 kit) + 0.25 HCl to both | | | | | |
| | (a) add 0.25 cc cysteine + 0.5 TcO4 qs to 1.25 ml, boil 6 min, add 1.25 ml sol'n C and reboil 4 min | 6.5 | 100/0 | 100/0 | 98.5/1.5 | 100/0 |
| | (b) Control - 0.5 ml TcO4 qs to 1.5 ml, boil 6 min, add 1.25 ml sol'n C and reboil 4 min | 7 | 95.2/4.8 | 95.7/4.3 | 97.6/2.4 | 97.9/2.1 |
| Mon, Jul. 20, 1998 (used re-elution) page 72 | 2/3 Re 1/3 SC - chg. vols. of cysteine b/f boil and sol'n C at 5 mins (used meter) | | | | | |
| | (a) .25 ml cysteine b/f boil, 0.5 soln C | 5.65 | 97.7/2.3 | n/a | 98.5/1.5 | 100/0 |
| | (b) .50 ml cysteine b/f boil, 0.5 soln C | 6.028 | 98.4/1.6 | n/a | 98.3/1.7 | 99.2/0.8 |
| | (c) .25 ml cysteine b/f boil, 1.25 soln C | 6.94 | 97.1/2.9 | n/a | 98.5/1.5 | 100/0 |
| | (d) .50 ml cysteine b/f boil, 1.25 soln C | 6.84 | 97.4/2.6 | n/a | 98.1/1.9 | 98.4/1.6 |
| | (e) as per preparation of B but used eluate A (48 hr + ingrowth) | 5.688 | 96.8/3.2 | n/a | 98.4/1.6 | n/a |
| Tues, Jul. 21, 1998 page 77 | 2/3 Re 1/3 SC - larger volumes of cysteine b/f boil and sol'n C at 5 mins | | | | | |
| | (a) .75 ml cyst. b/f boil, 0.5 soln C | 5.5 | 98.4/1.6 | 98.5/1.5 | 98.6/1.4 | n/a |
| | (b) 1.0 ml cyst. b/f boil, 0.5 soln C | 5.5 | 99.0/1.0 | 98.6/1.4 | 100/0 | n/a |
| | (c) .75 ml cyst. b/f boil, 1.25 soln C | 7.5 | 96.9/3.1 | 96.5/3.5 | 96.7/3.3 | n/a |
| | (d) 1.0 ml cyst. b/f boil, 1.25 soln C | 7 | 98.6/1.4 | 100/0 | 98.5/1.5 | n/a |
| Wed, Jul. 22, 1998 page 82 (re-eluate of A) | (a) repeat of a from T 7/21 | 6 | 98/2 | 98.4/1.6 | 98.7/1.3 | 100/0 |
| | (c) repeat of c from T 7/21 | 7 | 98.2/1.8 | 100/0 | 99.2/0.8 | 97.9/2.1 |
| | repeat of Sn Colloid | 7 | 100/0 | 100/0 | 93.7/6.3 | 95.1/3.9 |
| Mon, Jul. 27, 1998 page 92 | Reg SC with cysteine - 4 min boil - 5 min delay for addition of soln C | | | | | |
| | (a) .25 ml cyst/HCl b/f boil, .5 ml sol'n C | 6 | 99.1/0.9 | 100/0 | 99.4/0.6 | n/a |
| | (b) .25 ml cyst/HCl b/f boil, 1.25 ml sol'n C | 6.5 | 98.6/1.4 | 100/0 | 100/0 | n/a |
| | (c) .25 ml sol'n B (HCl) b/f boil, .5 ml sol'n C | 5 | 100/0 | 100/0 | 100/0 | n/a |
| | (d) .25 ml sol'n B (HCl) b/f boil, 1.25 ml sol'n C | 7 | 100/0 | 100/0 | 99.1/0.9 | n/a |
| Tues, Jul. 28, 1998 page 95 | 2/3 Re 1/3 SC with & without cysteine, with and without extra sol'n C | | | | | |
| | (a) .25 ml cyst/HCl, 0.25 ml TcO4 qs to 1.5 ml, 6 min boil, 5 min delay, 0.5 ml sol'n C | 5.5 | 98.3/1.7 | 98.6/1.4 | 98.6/1.4 | n/a |
| | (b) as per (a) except 1.25 ml sol'n C | 7 | 98.7/1.3 | 97.9/2.1 | 99.0/1.0 | 1SOPORE |
| | (c) .25 ml HCl, 0.25 ml TcO4 qs to 1.5 ml, 6 min boil, 5 min delay, 0.5 ml sol'n C | 5.5 | 99.0/1.0 | 98.6/1.4 | 98.8/1.2 | n/a |
| | (d) as per (c) except 1.25 ml sol'n C | 7 | 98.2/1.8 | 97.5/2.5 | 98.3/1.7 | n/a |
| Wed, Jul. 29, 1998 page 99 (repeat on Mon 7/28 but increase boiling time) | Reg SC with 0 and 1 mg cysteine | | | | | |
| | (a) vial A + .25 ml cysteine/HCl + .25 ml TcO4 qs to 1.5, boil 6 min, 5 min delay, .5 ml C | 5.5 | 100/0 | 100/0 | 100/0 | n/a |
| | (b) as per (a) but add 1.25 ml sol'n C | 7 | 100/0 | 100/0 | 100/0 | n/a |
| | (c) vial A + .25 ml vial B (HCl) + .25 ml TcO4 qs to 1.5, boil 6 min, 5 min delay, .5 ml C | 7 | 100/0 | 100/0 | 100/0 | n/a |
| | (d) as per (c) but add 1.25 ml sol'n C | 5.5 | 100/0 | 100/0 | 100/0 | n/a |

TABLE 4-continued

| DATE | PRODUCT | 1 hr 0.1 um | 6 hr 0.1 um | 1 hr 0.22 um | 6 hr 0.22 um | 1 hr 0.22 um | 6 hr 0.22 um | 1 hr 0.45 um |
|---|---|---|---|---|---|---|---|---|
| Wed, Jul. 15, 1998 | Reg SC with additional KReO4 - reg SC kit + 1 ml KReO4 + 2 ml TcO4 + 0.5 ml 0.5 NHCl | | | | | | | |
| | (a) 2.5 ml boiled 6 min + 1.25 ml sol'n C reboil 4 mins | 90.2 | 89.2 | 83.8 | 84.7 | 84.9 | 90.5 | 7.1 |
| | (b) 2.5 ml boiled 6 min, cool 5 minutes, and add 0.5 ml sol'n C | 90.2 | 90.6 | 89.2 | 89.3 | 90.2 | 91.5 | 20.6 |
| Thurs, Jul. 16, 1998 | Cysteine - 2/3 Re 1/3 SC (1/2 kit) + 0.25 HCl to both | | | | | | | |
| | (a) add 0.25 cc cysteine + 0.5 TcO4 qs to 1.25 ml, boil 6 min, add 1.25 ml sol'n C and reboil 4 min | 22.8 | 27.5 | 14.7 | 14.2 | 23.1 | 11.6 | 4.8 |
| | (b) Control - 0.5 ml TcO4 qs to 1.5 ml, boil 6 min, add 1.25 ml sol'n C and reboil 4 min | 65.1 | 59.4 | 25.7 | 25.9 | 36.9 | 28.5 | 8.3 |
| Mon, Jul. 20, 1998 (used re-elution) page 72 | 2/3 Re 1/3 SC - chg. vols. of cysteine b/f boil and sol'n C at 5 mins | | | | | | | |
| | (a) .25 ml cysteine b/f boil, 0.5 soln C | 45.1 | 27 | 18.6 | 20 | 25 | n/a | 9.2 |
| | (b) .50 ml cysteine b/f boil, 0.5 soln C | 18.3 | 20.5 | 7.3 | 8.3 | 12.6 | n/a | 4.1 |
| | Ⓒ .25 ml cysteine b/f boil, 1.25 soln C | 29.7 | 26.7 | 19.2 | 20.3 | 40 | n/a | 6.7 |
| | (d) .50 ml cysteine b/f boil, 1.25 soln C | 11.7 | 31.9 | 8.5 | 8.8 | 7.1 | n/a | 4.7 |
| | (e) as per preparation of B but used eluate A (48 hr + ingrowth) | 10.2 | n/a | 8.2 | n/a | n/a | n/a | 5.3 |
| Tues, Jul. 21, 1998 page 77 | 2/3 Re 1/3 SC - larger volumes of cysteine b/f boil and sol'n C at 5 mins | | | | | | | |
| | (a) .75 ml cyst. b/f boil, 0.5 soln C | 11.5 | 11.9 | 5.9 | 6.5 | n/a | n/a | 4 |
| | (b) 1.0 ml cyst. b/f boil, 0.5 soln C | 14.3 | 13.6 | 3.8 | 6.6 | n/a | n/a | 3.2 |
| | Ⓒ .75 ml cyst. b/f boil, 1.25 soln C | 50.6 | 30.5 | 6 | 6.3 | n/a | n/a | 3.2 |
| | (d) 1.0 ml cyst. b/f boil, 1.25 soln C | 12.3 | 18.4 | 5.2 | 5.1 | n/a | n/a | 3.8 |
| Wed, Jul. 22, 1998 page 82 (re-eluate of A) | (a) repeat of a from T 7/21 | 16.3 | 10 | 8 | 5.7 | n/a | n/a | 2.7 |
| | Ⓒ repeat of c from T 7/21 | 15.6 | 11 | 6.7 | 7 | n/a | n/a | 4.4 |
| | repeat of Sn Colloid | 2 | 2.7 | 1.8 | 1.8 | n/a | n/a | 0.7 |
| Mon, Jul. 27, 1998 page 92 | Reg SC with cysteine - 4 min boil - 5 min delay for addition of soln C | | | | | | | |
| | (a) .25 ml cyst/HCl b/f boil, .5 ml sol'n C | 92.1 | 92 | 87.4 | 87.1 | n/a | n/a | 36.2 |
| | (b) .25 ml cyst/HCl b/f boil, 1.25 ml sol'n C | 87.6 | 91.7 | 85.6 | 85.6 | n/a | n/a | 30.7 |
| | Ⓒ .25 ml sol'n B (HCl) b/f boil, .5 ml sol'n C | 94.6 | 92 | 90.8 | 88.7 | n/a | n/a | 21.1 |
| | (d) .25 ml sol'n B (HCl) b/f boil, 1.25 ml sol'n C | 95.1 | 94.5 | 69.4 | 53.6 | n/a | n/a | 4.3 |
| Tues, Jul. 28, 1998 page 95 | 2/3 Re 1/3 SC with & without cysteine, with and without extra sol'n C | 11.9 | 10.2 | 4.7 | 5.9 | | | 2.7 |
| | (a) .25 ml cyst/HCl, 0.25 ml TcO4 qs to 1.5 ml, 6 min boil, 5 min delay, 0.5 ml sol'n C | 55.7 | | 45.3 | | | | 23.8 |
| | (b) as per (a) except 1.25 ml sol'n C | 19.6 | 7.9 | 4.5 | 6.1 | | | 3.4 |
| | Ⓒ .25 ml HCl, 0.25 ml TcO4 qs to 1.5 ml, 6 min boil, 5 min delay, 0.5 ml sol'n C | 49.6 | 54.5 | 48.3 | 47.7 | | | 20.3 |
| | (d) as per Ⓒ except 1.25 ml sol'n C | 39.9 | 37.2 | 26.2 | 25.5 | | | 6.1 |
| Wed, Jul. 29, 1998 page 99 (repeat on Mon 7/28 but increase boiling time) | Reg SC with 0 and 1 mg cysteine | | | | | | | |
| | (a) vial A + .25 ml cysteine/HCl + .25 ml TcO4 qs to 1.5, boil 6 min, 5 min delay, .5 ml C | 88.9 | 91.5 | 86.9 | 86.7 | | | 27.5 |
| | (b) as per (a) but add 1.25 ml sol'n C | 89.4 | 89.1 | 87.9 | 87.9 | | | 15.9 |
| | Ⓒ vial A + .25 ml vial B (HCl) + .25 ml TcO4 qs to 1.5, boil 6 min, 5 min delay, .5 ml C | 94.7 | 93.9 | 93.2 | 90.5 | | | 13.7 |
| | (d) as per (c) but add 1.25 ml sol'n C | 96.3 | 95.3 | 90.8 | 92.8 | | | 13.3 |

| DATE | PRODUCT | 6 hr 0.45 um | 1 hr 0.45 um | 6 hr 0.45 um |
|---|---|---|---|---|
| Wed, Jul. 15, 1998 | Reg SC with additional KReO4 - reg SC kit + 1 ml KReO4 + 2 ml TcO4 + 0.5 ml 0.5 NHCl | | | |
| | (a) 2.5 ml boiled 6 min + 1.25 ml sol'n C reboil 4 mins | 7.7 | 12.1 | 16.6 |
| | (b) 2.5 ml boiled 6 min, cool 5 minutes, and add 0.5 ml sol'n C | 44 | 45 | 28.8 |

TABLE 4-continued

| | | | | |
|---|---|---|---|---|
| Thurs, Jul. 16, 1998 | Cysteine - 2/3 Re 1/3 SC (1/2 kit) + 0.25 HCl to both | | | |
| | (a) add 0.25 cc cysteine + 0.5 TcO4 qs to 1.25 ml, boil 6 min, add 1.25 ml sol'n C and reboil 4 min | 11.66 | 6.5 | 11.84 |
| | (b) Control - 0.5 ml TcO4 qs to 1.5 ml, boil 6 min, add 1.25 ml sol'n C and reboil 4 min | 8.7 | 8.3 | 7.1 |
| Mon, Jul. 20, 1998 (used re-elution) page 72 | 2/3 Re 1/3 SC - chg. vols. of cysteine b/f boil and sol'n C at 5 mins | | | |
| | (a) .25 ml cysteine b/f boil, 0.5 soln C | 7.6 | 5.1 | n/a |
| | (b) .50 ml cysteine b/f boil, 0.5 soln C | 5.6 | 2.7 | n/a |
| | ⓒ .25 ml cysteine b/f boil, 1.25 soln C | 9.6 | 8.3 | n/a |
| | (d) .50 ml cysteine b/f boil, 1.25 soln C | 6.9 | 6.2 | n/a |
| | (e) as per preparation of B but used eluate A (48 hr + ingrowth) | n/a | n/a | n/a |
| Tues, Jul. 21, 1998 page 77 | 2/3 Re 1/3 SC - larger volumes of cysteine b/f boil and sol'n C at 5 mins | | | |
| | (a) .75 ml cyst. b/f boil, 0.5 soln C | 3.5 | n/a | n/a |
| | (b) 1.0 ml cyst. b/f boil, 0.5 soln C | 3.7 | n/a | n/a |
| | ⓒ .75 ml cyst. b/f boil, 1.25 soln C | 3.1 | n/a | n/a |
| | (d) 1.0 ml cyst. b/f boil, 1.25 soln C | 4.2 | n/a | n/a |
| Wed, Jul. 22, 1998 page 82 (re-eluate of A) | (a) repeat of a from T 7/21 | 3.7 | n/a | n/a |
| | ⓒ repeat of c from T 7/21 | 4.3 | n/a | n/a |
| | repeat of Sn Colloid | 0.9 | n/a | n/a |
| Mon, Jul. 27, 1998 page 92 | Reg SC with cysteine - 4 min boil - 5 min delay for addition of soln C | | | |
| | (a) .25 ml cyst/HCl b/f boil, .5 ml sol'n C | 48 | n/a | n/a |
| | (b) .25 ml cyst/HCl b/f boil, 1.25 ml sol'n C | 61.5 | n/a | n/a |
| | ⓒ .25 ml sol'n B (HCl) b/f boil, .5 ml sol'n C | 43.5 | n/a | n/a |
| | (d) .25 ml sol'n B (HCl) b/f boil, 1.25 ml sol'n C | 5.1 | n/a | n/a |
| Tues, Jul. 28, 1998 page 95 | 2/3 Re 1/3 SC with & without cysteine, with and without extra sol'n C | | | |
| | (a) .25 ml cyst/HCl, 0.25 ml TcO4 qs to 1.5 ml, 6 min boil, 5 min delay, 0.5 ml sol'n C | 4.4 | | |
| | (b) as per (a) except 1.25 ml sol'n C | 4.7 | | |
| | ⓒ .25 ml HCl, 0.25 ml TcO4 qs to 1.5 ml, 6 min boil, 5 min delay, 0.5 ml sol'n C | 5.5 | | |
| | (d) as per ⓒ except 1.25 ml sol'n C | 5.9 | | |
| Wed, Jul. 29, 1998 page 99 (repeat on Mon 7/28 but increase boiling time) | Reg SC with 0 and 1 mg cysteine | | | |
| | (a) vial A + .25 ml cysteine/HCl + .25 ml TcO4 qs to 1.5, boil 6 min, 5 min delay, .5 ml C | 29.3 | | |
| | (b) as per (a) but add 1.25 ml sol'n C | 24.2 | | |
| | ⓒ vial A + .25 ml vial B (HCl) + .25 ml TcO4 qs to 1.5, boil 6 min, 5 min delay, .5 ml C | 4.9 | | |
| | (d) as per (c) but add 1.25 ml sol'n C | 12.2 | | |

TABLE 5

| DATE | PRODUCT | pH | 1 hr MEK origin/S.F. | 6 hr MEK origin/S.F. | 1 hr SALINE origin/S.F. |
|---|---|---|---|---|---|
| Tues, Aug. 4, 1998 page 103 | 2/3 Re 1/3 SC - kinetics: boiling times | | | | |
| | (a) full vial of A + 0.5 ml cyst/HCl + .1 ml TcO4 qs to 3.0 ml, 1 min. boil, 5 min. delay, 2.5 ml sol'n C (corrected in brackets) | 7 | 16.3/83.7 | | 37.06/63.0 |
| | (b) 2 min boil, 5 min delay | 7 | 64.9/35.1 | | 69.6/30.4 |
| | ⓒ 4 min boil, 5 min delay | 7 | 90.5/9.5 | | 92.6/30.4 |
| | (d) 6 min boil, 5 min delay | 7 | 96.8/3.2 | | 98.2/7.4 |
| | (e) 8 min boil, 5 min delay | 7 | 98.1/1.9 | | 100/0 |
| | (f) 10 min boil, 5 min delay | 7 | 98.6/1.4 | | 100/0 |

TABLE 5-continued

| Date | Description | | | | |
|---|---|---|---|---|---|
| Wed, Aug. 5, 1998 page 107 (biodistribution products) | (a) 1.5 ml 2/3 Re 1/3 SC + .5 ml cyst. + 8 ml TcO4 qs to 3 ml, 8 min boil, 5 min cool, + 2.5 ml PO4 buffer | 7 | 98.9/1.1 | | 100/0 |
| | (b) as per a but .5 ml HCl | 7 | 98.6/1.4 | | 98.6/1.4 |
| Fri, Aug. 7, 1998 page 111 | Antimony Colloid - .1 ml soln B to vial A, 1.5 ml TcO4 (eluate B), rolling boil for 45 minutes, cool 3 mins. in cool bath and add .25 ml sol'n C | 6 | 93.3/6.7 94.4/5.6 (did MEK 2ce) | | 100/0 |
| Mon, Aug. 10, 1998 page 112 | Reg SC with higher [Cysteine] - used 1/2 kits | | | | |
| | (a) 0.25 ml cysteine, .2 TcO4 qs to 1.5, boil 6 min., cool for 5 min. and add to 0.5 ml soln C | | 100/0 | 100/0 | 100/0 |
| | (b) as per (a) but 0.25 ml HCl | | 100/0 | 100/0 | 100/0 |
| | ⓒ as per (a) but 1.25 ml soln C | | 100/0 | 100/0 | 100/0 |
| | (d) as per (a) but 0.25 ml HCl and 1.25 ml soln C | | 100/0 | 100/0 | 100/0 |
| Wed, Aug. 12, 1998 page 115 | Re Colloid with Cysteine - high and low PO4 (from biodistribution study) | | | | |
| | (a) full kit - add 0.5 ml Cysteine, 0.5 ml TcO4 qs to 3 ml, boil 8 min, cool 5 min, 1 ml PO4 | 6 | 98.6/1.4 | | 100/0 |
| | (b) as per (a) but add 2.5 ml PO4 | 7 | 98.8/1.2 | | 100/0 |
| Mon, Aug. 17, 1998 page 121 | Re Colloid with Cysteine or HCl, 8 min boil 5 min delay | | | | |
| | (a) add 0.5 ml cysteine, 0.4 ml TcO4 qs to 3 ml, 8 min boil, 5 min delay, +1 cc soln C | 5.5 | 99.4/0.6 | 99.2/0.8 | 99.0/1.0 |
| | (b) as per (a) but 2.5 cc soln C | 7 | 98.3/1.7 | 99.0/1.0 | 98.9/1.1 |
| | ⓒ add 0.5 ml Hcl, 0.4 ml TcO4 qs to 3 ml, 8 min boil, 5 min delay, +1 cc soln C | 6 | 98.2/1.8 | 98.0/2.0 | 98.0/2.0 |
| | (d) as per ⓒ but 2.5 cc soln C | 7 | 99.4/0.6 | 99.4/0.6 | 99.3/0.7 |
| Tues, Aug. 18, 1998 page 124 | Re Colloid, Cysteine, with and without delay prior to addition of PO4 | | | | |
| | (a) add 0.5 ml cysteine, 0.2 ml TcO4 qs to 3 ml, 8 min boil, 5 min delay, add 2.5 cc soln C | 7 | 99.0/1.0 | 98.8/1.2 | 98.8/1.2 |

| DATE | PRODUCT | 6 hr SALINE origin/S.F. | 1 hr 0.1 um | 6 hr 0.1 um | 1 hr 0.22 um |
|---|---|---|---|---|---|
| Tues, Aug. 4, 1998 page 103 | 2/3 Re 1/3 SC - kinetics: boiling times | | | | |
| | (a) full vial of A + 0.5 ml cyst/HCl + .1 ml TcO4 qs to 3.0 ml, 1 min. boil, 5 min. delay, 2.5 ml sol'n C (corrected in brackets) | | 25.6 | | 2.93 [18] |
| | (b) 2 min boil, 5 min delay | | 20.9 [32] | | 5.0 [7.7] |
| | ⓒ 4 min boil, 5 min delay | | 31.1 [34.4] | | 5.4 [6.0] |
| | (d) 6 min boil, 5 min delay | | 15.6 [16.1] | | 6.1 [6.3] |
| | (e) 8 min boil, 5 min delay | | 36.0 [36.7] | | 8.2 [8.4] |
| | (f) 10 min boil, 5 min delay | | 37.5 [38.0] | | 8.9 [9.0] |
| Wed, Aug. 5, 1998 page 107 (biodistribution products) | (a) 1.5 ml 2/3 Re 1/3 SC + .5 ml cyst. + 8 ml TcO4 qs to e ml, 8 min boil, 5 min cool, + 2.5 ml PO4 buffer | | 82.9 | | 79.9 |
| | (b) as per a but .5 ml HCl | | 18.3 | | 6.3 |
| Fri, Aug. 7, 1998 page 111 | Antimony Colloid - .1 ml soln B to vial A, 1.5 ml TcO4 (eluate B), rolling boil for 45 minutes, cool 3 mins in cool bath and add .25 ml sol'n C | | 3.7 | | 1.3 |
| Mon, Aug. 10, 1998 page 112 | Reg SC with higher [Cysteine] - used 1/2 kits | | | | |
| | (a) 0.25 ml cysteine, .2 TcO4 qs to 1.5, boil 6 min., cool for 5 min. and add to 0.5 ml soln C | 100/0 | 45 | 60.1 | 35.3 |
| | (b) as per (a) but 0.25 nl HCl | 100/0 | 96.3 | 97.9 | 97.1 |
| | ⓒ as per (a) but 1.25 ml soln C | 98.9/1.1 | 47.1 | 43 | 27.1 |
| | (d) as per (a) but 0.25 ml HCl and 1.25 ml soln C | 100/0 | 97.8 | 97.9 | 94.6 |
| Wed, Aug. 12, 1998 page 115 | Re Colloid with Cysteine - high and low PO4 (from biodistribution study) | | | | |
| | (a) full kit - add 0.5 ml Cysteine, 0.5 ml TcO4 qs to 3 ml, boil 8 min, cool 5 min, 1 ml PO4 | | 6.9 | | 4.4 |
| | (b) as per (a) but add 2.5 ml PO4 | | 12.6 | | 5.6 |

TABLE 5-continued

| | | | | | | |
|---|---|---|---|---|---|---|
| Mon, Aug. 17, 1998<br>page 121 | Re Colloid with Cysteine or HCl,<br>8 min boil 5 min delay | | | | | |
| | (a) add 0.5 ml cysteine, 0.4 ml TcO4 qs to<br>3 ml, 8 min boil, 5 min delay,<br>+1 cc soln C | | | | | 3.2 |
| | (b) as per (a) but 2.5 cc soln C | | | | | 4 |
| | ⓒ add 0.5 ml Hcl, 0.4 ml TcO4 qs to<br>3 ml, 8 min boil, 5 min delay,<br>+1 cc soln C | | | | | 59.5 |
| | (d) as per ⓒ but 2.5 cc soln C | | | | | 46.6 |
| Tues, Aug. 18, 1998<br>page 124 | Re Colloid, Cysteine, with and without<br>delay prior to addition of PO4 | | | | | |
| | (a) add 0.5 ml cysteine, 0.2 ml TcO4 qs to<br>3 ml, 8 min boil, 5 min delay,<br>add 2.5 cc soln C | | | | | 4.3<br>5.8 |

| DATE | PRODUCT | 6 hr<br>0.22 um | 1 hr<br>0.22 um | 6 hr<br>0.22 um | 1 hr<br>0.45 um | 6 hr<br>0.45 um |
|---|---|---|---|---|---|---|
| Tues, Aug. 4, 1998<br>page 103 | 2/3 Re 1/3 SC - kinetics: boiling times | | | | | |
| | (a) full vial of A + 0.5 ml cyst/HCl +<br>.1 ml TcO4 qs to 3.0 ml, 1 min. boil,<br>5 min. delay, 2.5 ml sol'n C<br>(corrected in brackets) | | | | 1.6 [9.8] | |
| | (b) 2 min boil, 5 min delay | | | | 3.3 [5.1] | |
| | ⓒ 4 min boil, 5 min delay | | | | 3.8 [5.1] | |
| | (d) 6 min boil, 5 min delay | | | | 4.0 [4.2] | |
| | (e) 8 min boil, 5 min delay | | | | 5.4 [5.5] | |
| | (f) 10 min boil, 5 min delay | | | | 7.4 [7.5] | |
| Wed, Aug. 5, 1998<br>page 107<br>(biodistribution<br>products) | (a) 1.5 ml 2/3 Re 1/3 SC + .5 ml cyst. +<br>8 ml TcO4 qs to e ml, 8 min boil, 5 min<br>cool, + 2.5 ml PO4 buffer | | | 22 | | |
| | (b) as per a but .5 ml HCl | | | 4.8 | | |
| Fri, Aug. 7, 1998<br>page 111 | Antimony Colloid - .1 ml soln B to vial A,<br>1.5 ml TcO4 (eluate B), rolling boil for<br>45 minutes, cool 3 mins in cool bath<br>and add .25 ml sol'n C | | | 1.5 | | |
| Mon, Aug. 10, 1998<br>page 112 | Reg SC with higher [Cysteine] - used 1/2<br>kits | | | | | |
| | (a) 0.25 ml cysteine, .2 TcO4 qs to 1.5,<br>boil 6 min., cool for 5 min. and add to<br>0.5 ml soln C | 34.2 | | 32.6 | | 32.8 |
| | (b) as per (a) but 0.25 nl HCl | 94.7 | | 56.7 | | 18.3 |
| | ⓒ as per (a) but 1.25 ml soln C | 27.6 | | 13.4 | | 19.1 |
| | (d) as per (a) but 0.25 ml HCl and<br>1.25 ml soln C | 96.3 | | 18.5 | | 12.7 |
| Wed, Aug. 12, 1998<br>page 115 | Re Colloid with Cysteine - high and<br>low PO4 (from biodistribution study) | | | | | |
| | (a) full kit - add 0.5 ml Cysteine,<br>0.5 ml TcO4 qs to 3 ml, boil 8 min,<br>cool 5 min, 1 ml PO4 | | | 3.9 | | |
| | (b) as per (a) but add 2.5 ml PO4 | | | 4.6 | | |
| Mon, Aug. 17, 1998<br>page 121 | Re Colloid with Cysteine or HCl,<br>8 min boil 5 min delay | | | | | |
| | (a) add 0.5 ml cysteine, 0.4 ml TcO4 qs to<br>3 ml, 8 min boil, 5 min delay,<br>+1 cc soln C | 3.03 | | 2.9 | | 2.4 |
| | (b) as per (a) but 2.5 cc soln C | 4.8 | | 3 | | 4.1 |
| | ⓒ add 0.5 ml Hcl, 0.4 ml TcO4 qs to<br>3 ml, 8 min boil, 5 min delay,<br>+1 cc soln C | 60.6 | | 31.9 | | 10.1 |
| | (d) as per ⓒ but 2.5 cc soln C | 45.6 | | 9.1 | | 6.5 |
| Tues, Aug. 18, 1998<br>page 124 | Re Colloid, Cysteine, with and without<br>delay prior to addition of PO4 | | | | | |
| | (a) add 0.5 ml cysteine, 0.2 ml TcO4 qs to<br>3 ml, 8 min boil, 5 min delay,<br>add 2.5 cc soln C | 4.4<br>7 | | 4.7<br>4.3 | | 4.3 |

TABLE 5-continued

| DATE | PRODUCT | 1 hr 0.45 um | 6 hr 0.45 um | 6 hr 0.45 um | 1 hr 0.45 um | 6 hr 0.45 um |
|---|---|---|---|---|---|---|
| Tues, Aug. 4, 1998 page 103 | 2/3 Re 1/3 SC - kinetics: boiling times (a) full vial of A + 0.5 ml cyst/HCl + .1 ml TcO4 qs to 3.0 ml, 1 min. boil, 5 min. delay, 2.5 ml sol'n C (corrected in brackets) (b) 2 min boil, 5 min delay ⓒ 4 min boil, 5 min delay (d) 6 min boil, 5 min delay (e) 8 min boil, 5 min delay (f) 10 min boil, 5 min delay | | | | | |
| Wed, Aug. 5, 1998 page 107 (biodistribution products) | (a) 1.5 ml 2/3 Re 1/3 SC + .5 ml cyst. + 8 ml TcO4 qs to e ml, 8 min boil, 5 min cool, + 2.5 ml PO4 buffer (b) as per a but .5 ml HCl | | | | | |
| Fri, Aug. 7, 1998 page 111 | Antimony Colloid - .1 ml soln B to vial A, 1.5 ml TcO4 (eluate B), rolling boil for 45 minutes, cool 3 mins in cool bath and add .25 ml sol'n C | | | | | |
| Mon, Aug. 10, 1998 page 112 | Reg SC with higher [Cysteine] - used 1/2 kits (a) 0.25 ml cysteine, .2 TcO4 qs to 1.5, boil 6 min., cool for 5 min. and add to 0.5 ml soln C | | | 32.8 | | |
| | (b) as per (a) but 0.25 nl HCl | | | 18.3 | | |
| | ⓒ as per (a) but 1.25 ml soln C | | | 19.1 | | |
| | (d) as per (a) but 0.25 ml HCl and 1.25 ml soln C | | | 12.7 | | |
| Wed, Aug. 12, 1998 page 115 | Re Colloid with Cysteine - high and low PO4 (from biodistribution study) (a) full kit - add 0.5 ml Cysteine, 0.5 ml TcO4 qs to 3 ml, boil 8 min, cool 5 min, 1 ml PO4 (b) as per (a) but add 2.5 ml PO4 | | | | | |
| Mon, Aug. 17, 1998 page 121 | Re Colloid with Cysteine or HCl, 8 min boil 5 min delay (a) add 0.5 ml cysteine, 0.4 ml TcO4 qs to 3 ml, 8 min boil, 5 min delay, +1 cc soln C | | | 2.4 | | |
| | (b) as per (a) but 2.5 cc soln C | | | 4.1 | | |
| | ⓒ add 0.5 ml Hcl, 0.4 ml TcO4 qs to 3 ml, 8 min boil, 5 min delay, +1 cc soln C | | | 10.1 | | |
| | (d) as per ⓒ but 2.5 cc soln C | | | 6.5 | | |
| Tues, Aug. 18, 1998 page 124 | Re Colloid, Cysteine, with and without delay prior to addition of PO4 | | | 4.3 | | |
| | (a) add 0.5 ml cysteine, 0.2 ml TcO4 qs to 3 ml, 8 min boil, 5 min delay, add 2.5 cc soln C | | | 5.1 | | |

TABLE 6

| % Dose/Organ | #1 | #2 | #3 | #4 | #5 | #6 | t-Test (2 tail, heteroscedastic) |
|---|---|---|---|---|---|---|---|
| Blood | | | | | | | |
| Clinical SC | 0.42 | 0.52 | 0.47 | | | | |
| 0.2 u Filtered SC | 1.37 | 1.19 | 1.33 | 1.42 | | | 4.45612E-05 |
| Tin Colloid (in house) | 24.65 | 24.59 | 29.4 | 22.7 | | | 0.000411631 |
| Re Colloid (No Cysteine) | 0.41 | 0.44 | 0.6 | | | | 0.852461938 |
| Re Colloid, Cysteine & Hi PO4 | 1.76 | 1.31 | 0.66 | 0.99 | 0.71 | 2.38 | 0.028205626 |
| Re Colloid, Cysteine & Low PO4 | 1.27 | 0.95 | 0.48 | | | | 0.200119474 |
| Lung | | | | | | | |
| Clinical SC | 0.12 | 0.41 | 0.13 | | | | |
| 0.2 u Filtered SC | 0.3 | 0.31 | 0.26 | 0.54 | | | 0.315702092 |
| Tin Colloid (in house) | 1.71 | 2.39 | 3.06 | 2.73 | | | 0.002586557 |
| Re Colloid (No Cysteine) | 0.55 | 2.17 | 0.71 | | | | 0.212117074 |
| Re Colloid, Cysteine & Hi PO4 | 0.15 | 0.22 | 0.28 | 0.23 | 0.25 | 0.32 | 0.843375337 |
| Re Colloid, Cysteine & Low PO4 | 0.2 | 0.22 | 0.13 | | | | 0.741863321 |

TABLE 6-continued

| % Dose/Organ | #1 | #2 | #3 | #4 | #5 | #6 | t-Test (2 tail, heteroscedastic) |
|---|---|---|---|---|---|---|---|
| Liver | | | | | | | |
| Clinical SC | 94.97 | 96.11 | 93.87 | | | | |
| 0.2 u Filtered SC | 93.32 | 91.32 | 92.52 | 93.94 | | | 0.055467469 |
| Tin Colloid (in house) | 11.15 | 10.18 | 6.68 | 9.48 | | | 1.39398E-08 |
| Re Colloid (No Cysteine) | 95.26 | 91.33 | 92.68 | | | | 0.24346448 |
| Re Colloid, Cysteine & Hi PO4 | 95.1 | 94.06 | 95.03 | 94.85 | 94.5 | 91.65 | 0.394015085 |
| Re Colloid, Cysteine & Low PO4 | 93.52 | 94.16 | 95.26 | | | | 0.463364276 |
| Spleen | | | | | | | |
| Clinical SC | 2.92 | 1.61 | 4.37 | | | | |
| 0.2 u Filtered SC | 1.94 | 3.2 | 3.1 | 1.4 | | | 0.581790298 |
| Tin Colloid (in house) | 0.82 | 0.74 | 0.97 | 0.61 | | | 0.110303276 |
| Re Colloid (No Cysteine) | 1.97 | 4.27 | 2.59 | | | | 0.983393812 |
| Re Colloid, Cysteine & Hi PO4 | 1.21 | 2.52 | 1.24 | 1.16 | 1.43 | 2.58 | 0.244945765 |
| Re Colloid, Cysteine & Low PO4 | 1.31 | 2.46 | 1.85 | | | | 0.304522545 |
| Sternum | | | | | | | |
| Clinical SC | 0.04 | 0.03 | 0.04 | | | | |
| 0.2 u Filtered SC | 0.04 | 0.04 | 0.07 | 0.06 | | | 0.124810548 |
| Tin Colloid (in house) | 0.57 | 0.62 | 0.9 | 0.88 | | | 0.003734771 |
| Re Colloid (No Cysteine) | 0.09 | 0.06 | 0.12 | | | | 0.086295535 |
| Re Colloid, Cysteine & Hi PO4 | 0.16 | 0.09 | 0.12 | 0.14 | 0.13 | 0.17 | 0.000246015 |
| Re Colloid, Cysteine & Low PO4 | 0.2 | 0.14 | 0.15 | | | | 0.018217706 |
| Femur | | | | | | | |
| Clinical SC | 0.09 | 0.05 | 0.04 | | | | |
| 0.2 u Filtered SC | 0.1 | 0.1 | 0.07 | 0.08 | | | 0.20555373 |
| Tin Colloid (in house) | 1.2 | 0.59 | 1.56 | 1.35 | | | 0.012538985 |
| Re Colloid (No Cysteine) | 0.24 | 0.19 | 0.28 | | | | 0.008059273 |
| Re Colloid, Cysteine & Hi PO4 | 0.29 | 0.28 | 0.31 | 0.48 | 0.3 | 0.41 | 0.000143513 |
| Re Colloid, Cysteine & Low PO4 | 0.34 | 0.24 | 0.2 | | | | 0.029063033 |
| Kidney | | | | | | | |
| Clinical SC | | | | | | | |
| 0.2 u Filtered SC | | | | | | | |
| Tin Colloid (in house) | | | | | | | |
| Re Colloid (No Cysteine) | 0.12 | 0.34 | 0.25 | | | | |
| Re Colloid, Cysteine & Hi PO4 | 0.15 | 0.33 | 0.32 | 0.38 | 0.25 | 0.71 | |
| Re Colloid, Cysteine & Low PO4 | 0.24 | 0.19 | 0.14 | | | | |
| Body | | | | | | | |
| Clinical SC | 1.7 | 1.64 | 1.5 | | | | |
| 0.2 u Filtered SC | 3.95 | 4.56 | 3.68 | 3.95 | | | 0.000453048 |
| Tin Colloid (in house) | 59.9 | 60.89 | 57.43 | 62.25 | | | 1.09146E-05 |
| Re Colloid (No Cysteine) | 1.7 | 1.53 | 3.27 | | | | 0.423185906 |
| Re Colloid, Cysteine & Hi PO4 | 2.62 | 2.08 | 2.57 | 2.47 | 3.02 | 3.52 | 0.002239228 |
| Re Colloid, Cysteine & Low PO4 | 3.81 | 2.43 | 2.18 | | | | 0.1409944026 |
| Tail | | | | | | | |
| Clinical SC | 0.55 | 0.73 | 0.71 | | | | |
| 0.2 u Filtered SC | 2.49 | 1.44 | 0.65 | 0.71 | | | 0.221745661 |
| Tin Colloid (in house) | 6.27 | 5.64 | 6.83 | 10.65 | | | 0.009485157 |
| Re Colloid (No Cysteine) | 0.96 | 0.69 | 93.59 | | | | 0.420643887 |
| Re Colloid, Cysteine & Hi PO4 | 2.62 | 2.08 | 2.57 | 2.47 | 3.02 | 3.52 | 8.91773E-05 |
| Re Colloid, Cysteine & Low PO4 | 89.3 | 0.68 | 1.39 | | | | 0.417827514 |

FULL CITATIONS FOR REFERENCES REFERRED TO IN THE SPECIFICATION

Alazraki N, Eshima D, et al., Lymphoscintigraphy, the Sentinel Node Concept, and the Intraoperative Gamma Probe in Melanoma, Breast Cancer, and Other Potential Cancers. Seminars in Nuclear Medicine 27:55–67, 1997.

Alazraki N. Applying the Sentinel Node Concept to Staging and Surgical Management of Early Breast Cancer Using Lymphoscintigraphy and Gamma Probe Guided Sentinel Node Biopsy. Society of Nuclear Medicine Categorical Seminar 29–31, 1998.

Albertini J, Cruse W, et al. Intraoperative Radiolymphoscintigraphy Improves Sentinel Lymph Node Identification for Patients with Melanoma. Annals of Surgery 223(2):217–224, 1996.

Albertini J, Lyman G, et al. Lymphatic Mapping and Sentinel Node Biopsy in the Patient With Breast Cancer. JAMA 276(22):1818–1822, 1996.

Atkins H L, Richards P and Scheffer L. Nucl. Applic. 2, 27 (1966).

Atkins H L, Hauser W, Richards P (1970). Factors affecting distribution of technetium-sulfur colloid. J. Reticuloendothel Soc. 8:176–184.

Ballinger J, Andrey T, et al. Formulation of Technetium-99m-Aerosol Colloid with Improved Delivery Efficiency for Lung Ventilation Imaging. The Journal of Nuclear Medicine 34(2):268–271, 1993.

Bennett L and G Lago. cutaneous Lymphoscintigraphy in Malignant Melanoma. Seminars in Nuclear Medicine 13(1):61–69, 1983.

Bergqvist L, Strant S and R Person. Particle Sizing and Biokinetics of Interstitial Lymphoscintigraphic Atents. Seminars in Nuclear Medicine 13(1):9–19, 1983.

Bertil R, Persson R and Y Naversten: Technetium-99m Sulfide Colloid Preparation for Scintigraphy of the Reticuloendothelial System. Acta Radiol Ther Phys Biol 9:567–576, 1969.

Billinghurst M. Commercially Available particulate Radiopharmaceuticals (In Press).

Billinghurst M W, Jette D (1979). Colloidal particle-size determination by gel filtration. J. Nucl. Med. 20:133–137.

Bradfield J W B, Wagner Jr. H N. (1977). The relative importance of blood flow and liver phagocytic function in the distribution of technetium-99m sulfur colloid. J. Nuclo. Med. 18:620–621.

Briscoe H V, Robinson P L and Studdar E M. J. Chem. Soc. 1439 (1931).

Cady B. The Need to Reexamine Axillary Lymph Node Dissection in Invasive Breast Cancer. Cancer 73(3):505–508, 1994.

Chaudhuri T K, Evans T C, Chaudchuri T K (1973). Autoradiographic studies of distribution in the liver of 198 Au and 99m Tc sulfur colloid. Radiology, 109:633–637.

Cifka J and Vesely P. New Developments in Radiopharmaceuticals and Labelled Compounds. p. 53 (Vienna, IAEA, 1974) p. 53.

Clarke M, Tyrrell D and J Barrett. Normal Volunteer Studies with Modified Technetium-99m Tin Colloid. Nuclear Medicine Communications 6:641–648, 1985.

Cohen M B, J. Nucl. Med. 11, 767 (1970).

Cox C. Sentinel Node Localization with Lymphoscintigraphy Using Intraoperative Gamma Probe in Women with Breast Cancers: A Surgeon's Experience. Societty of Nuclear Medicine Categorical Seminar 32–36, 1998.

Dass R, Singh A and U Chauhan. Development of a Dextra Kit for Labeling with 20 Technetium-99m and its Evaluation for Lymphoscintigraphy. Nucl Med Biol 20(5):701–706, 1993.

David M A, Jones A G, Trindade H. J. Nucl. Med. 7, 817 (1966).

Davis M A, Jones A G, Trindade H (1974). A rapid and accurate method for sizing radiocolloids, J. Nucl. Med. 15:925–928.

De Cicco C, Cremonesi M, Chinol M, et al. Optimization of Axillary Lymphoscintigraphy to Detect the Sentinel Node in Brease Cancer. Tumori 83:539–541, 1997.

Dinegar R H and Smellie R H. J. Colloid Sci. 7, 370 (1952)/

Dobson E L (1957). Factors controlling phagocytosis. In: Halpern B N (ed) Physiopathology of the reticuloendothelial system. Oxford, Blackwell, pp. 80–114.

Dowson W M and Jones W F. Mikrochim. Acta 339 (1974).

Dunson G, Thrall J, Stevenson J and S Pinsky. Technetium-99m Minicolloid for Radionuclide Lymphography. Radiology 109:387–392, 1973.

Eary J. Sentinel Lymph Node Detection in Melanoma and Breast Cancer: The role of Lymphoscintigraphy. Society of Nuclear Medicine Categorical Seminar 132–134, 1998.

Ege G, Warbick-Cerone A and M Bronskill. Radionuclide Lymphoscintigraphy—An Update. Radiopharmaceuticals II: 241–258, 1979.

Ege G and A Warbick. Lymphoscintigraphy: A Comparison of Technetium-99m Antimony Sulfide Colloid and Technetium-99m Stannous Phytate. British Journal of Radiology 52:124–129, 1979.

Ege G. Lymphoscintigraphy in Oncology. Chaper 94 Nuclear Medicine Volume II. Mosby Year Book, St. Louis, Mo. 1504–1523.

Ege G. Internal Mammary Lymphoscintigraphy In Breast Carcinoma: A Study of 1072 Patients. Int. J. Radiation Oncology Biol. Phys. 2:755–761, 1977.

Ercan M, Schmeidereit M, Senekowitsch and H Kriegel. Evaluation of Technetium-99m Dextran as a Lymphoscintingraphic Agent in Rabbits. Eur J Nucl Med 11:80–84, 1985.

Eshima D, Eshima L, Gotti N, et al. Technetium-99m-Sulfur Colloid for Lymphoscintigraphy: Effects of Preparation Parameters. J Nucl Med 37:1575–1578, 1996.

For a La Mer Sulfur Sol. Bibliography, see Refs 2–15 in Kerker M. et al. J. Phys. Chem. 67, 2105 (1963).

Friedman H L and Kerker M. J. Colloid Sci. 8, 80 (1953).

Frier M, Griffiths P and A Ramsey. The Physical and Chemical Characteristics of Sulfur Colloids. Eur J Nuc Med 6:255–260, 1981.

Frier M, Griffiths P and A Ramsay. The Biological Fate of Sulfur Colloid. Eur J Nucl Med 6:371–374, 1981.

Garzon O L, Palcos M G and Radicella R. Int. J. Appl. Radiat. Isol. 16, 613 (1965).

Glas E , Essner R and D Morton. Kinetics of Three Lymphoscintigraphic Agents in Patients with Cutaneous Melanoma. J Nucl Med 39:1185–1190, 1998.

Goehring M, Stamin H and Feldmann U. Z Anorg. Allgem. Chem. 250, 56 (1942).

Goodwin D, Finston R, Colombetti L, et al. In for Imaging: Lymph Node Visualization. Radiology 94:175–178, 1970.

Guiliano A, Jones R, Brennan M and T Statman: Sentinel Lymphadenectomy in Breast Cancer. Journal of Clinical Oncology 15(6):2345–2350, 1997.

Gulec S, et al. Intraoperative Gamma Probes. Nuclear Medicine Annals 97:209–237, 1997.

Haliback H., George E S, Hendershott L R, Donati R M (1975). Differing mechanisms of Tc 99m sulfur colloid (TSC) and A 198 colloid (AuC) uptake. J. Nucl. Med. 16:532.

Hall R, O'Mara E and I Tyson. Critical Review of Parameters Affecting the Properties of $^{99m}$Tc—Sulfur Colloid Solutions. Journal of Nuclear Medicine 13(11):P35, 1972.

Handbook of Chemistry and Physics, 59 edn. D-203 (Chemical Rubber Company, 1978–1979).

Harper P V, Lathrop K and Richards P. J. Nucl. Med. 5, 382 (1964).

Hauser W, Aktins H and P Richards. Lymph Node Scanning with $^{99m}$Tc—Sulfur Colloid. Radiology 92:1369–1371, 1969.

Henze. E, Sschelbert H, Collins J, et al. Lymphoscintigraphy with Tc-99m-Labeled Dextran. Journal of Nuclear Medicine 23:923–929, 1982.

Hilditch T, Elliott A, Murray T and T Whateley. Formation of Large Particles in a $^{99m}$Tc-Tin Colloid Preparation. Nuclear Medicine Communications 7:845–850, 1986.

Hinkle G. Intraoperative Lymphoscintigraphy and Intraoperative Lymphatic Mapping. Society of Nuclear Medicine Categorical Seminar 28–30, 1998.

Hung J, Wiseman G, Wahner H, et al. Filtered Technetium-99m-Sulfur Colloid Evaluated for Lymphoscintigraphy. J. Nucl Med 36:1895–1901, 1995.

Hylin J W, Wood J L (1959). Enzymatic formation of polysulfides from mercaptopyruvate. J. Biol. Chem. 234:241–2144.

Ikeda I, Inouse O and K Kurata. A New Preparation Method for 99m Tc-Phytate. J Nucl Med 17(5): 389–393, 1976.

Illum L, Davis S, Wllson C, et al. Blood Clearance and Organ Deposition of Intravenously Administered Colloidal Particles. The Effects of Particle Size, Nature and Shape. International Journal of Pharmaceutics 12:135–146, 1982.

Ito Y, Otsuka, Nagai K, et al. Lymphoscintigraphy by SC Injection of $^{67}$Ga-citrate. Eur J Nucl Med 7:260–265, 1982.

Kaplan W, Davis M and C Rose. A Comparison of Two Technetium-99m-Labeled Radiopharamceuticals for Lymphoscintigraphy: Concise Communication. J Nucl Med 20:933–937, 1979.

Krag D, Meijer S, Weaver D, et al. Minimal-Access Surgery for Staging of Malignant Melanoma. Arch Surg 130:654–658, 1995.

Kotegov K V, Pavlov O N and Shvedov V P. Technetium. In Advances in Inorg. Chem. and Radiochem., Vol. 2 (eds Emeleus H J and Sharpe A G) PP 19–47 (New York, Academic Press, 1968).

Larson S M, Nelp W B (1966). Radiopharmacology of a simplified technetium-99m-colloid preparation of photoscanning. J. Nucl. Med. 7:817–826.

Lyons D and Nickless G. In Inorganic Sulfur Chemistry (ed. G. Nickless) p. 530 (Elsevier, New York, 1968).

Mizoguchi T and Takei Y and Okabe T. Bull. Chem. Soc. Japan 49, 70 (1976).

Mrdun A, Murray D, Herda S, et al. Early Stage Melanoma: Lymphoscintigraphy, Reproducibility of Sentinel Node Detection, and Effectiveness of the Intraoperative Gamma Probe. Radiology 199:171–175, 1996.

Müller A and Krebs B, Z. Anorg. Aligem. Chem. 342,182 (1966).

Müller A and Krebs B, Z. Anorg. Allgem. Chem. 353, 259 (1967).

Nagai K, Ito Y, Otsuka N, et al. Experimental Studies on Uptake of Technetium-99m Antimony Sulfide Colloid in RES—A Comparisonk with Various Technetium-99m Colloids. Int J Nucl Med Biol 8:85–89, 1981.

Nagai K, Ito Y, Otsuka N and A Muranaka. Deposition of Small 99mTc-Labelled Colloids in Bone Marrow and Lymph Nodes. Eur J Nucl Med 7:66–70, 1982.

Neukomm S, Lerch P, Jallut O (1957). Physicochemical factors governing the phagocytic function of the RES. In: Halpern B N (ed). Physiopathology of the reticuloendothelial system. Oxford. Blackwell, pp. 115–127.

Palmer W G. Experimental Inorganic Chemistry p. 3$^{70}$ (Cambridge University Press, London, 1954).

Pauli W and Laub A. Kolloid Z. 80, 178 (1937).

Pestana A. Sols A (1970). Reversible inactivation by elemental sulfur and mercurials of rat liver serine dehydratase and certain sulfhydryl enzymes. Biochem Biophys. Res. Commun. 39:522–529.

Pijpers R, Collet G, Meijer S and O Hoekstra. The Impact of Dynamic Lymphoscintigraphy and Gamma Probe Guidance on Sentinel Node Biopsy in Melanoma. Eur J Nucl Med 22:1238–1241, 1995.

Reintgen D and A Conrad. Detection of Occult Melanoma Cells in Sentinel Lymph Nodes and Blood. Seminars in Oncology 24(1):S4–S11, 1997.

Reintgen D, E Joseph, Lyman G, et al. The Role of Selective Lymphadenectomy in Breast Cancer. Cancer Control Journal 4(3).

Rijke A, Croft B, Johnson R, et al. Lymphoscintigraphy and Lymphodema of the Lower Extremities. J Nucl Med 31(6):990–998.

Sadek S, Owunwanne A, et al. Preparation and Evaluation of Tc-99m Hydroxy-Ethyl Starch as a Potential Radiopharmaceutical for Lymphoscintigraphy: Comparison with Tc-99m Human Serum Albumin, Tc-99m Dextran, and Tc-99m Sulfur Microcolloid. Lymphology 22:157–166, 1989.

Schillaci O, Scopinaro F, Tavolaro R, et al. Technetium-99m Sestamibi Imaging in the Detection of Auxillary Lymph Node Involvement in Patients with Breast Cancer. Anticancer Research 17:1607–1610, 1997.

Schulze H. J. Prakt. Chem. 27, 320 (1883).

Schussler H D and Herrmann G. Radiochim. Acta 13, 65 (1970).

Scott G B D, Williams H S, Marriott P M (1967). The phagocytosis of colloidal particles of different sizes. Br. J. Exp. Phathol. 48:411–416.

Sogami M and Foster J F. J. Biol. Chem. 237, 2514 (1962).

Steigman J, Solomon N and L Hwang. Technetium-Sulfur Colloid. Appl. Radiat. Isot. 37:223, 1986.

Strand S and L Bergqvist. Radiolabeled Colloids and Macromolecules in the Lymphatic System. Critical Reviews in Therapeutic Drug Carrier Systems 6(3):211–238, 1989.

Stem H S, McAfee J G and Subramanian G. J. Nucl. Med. 7, 665 (1966).

Sundram F, Edmondson R, Ang E, et al. $^{99}$Tc$^{m}$-(tin) colloid scans in the evaluation of renal transplant rejection. Nuclear Medicine Communications 7:897–906, 1986.

Uren R, Howman-Giles R, Thompson J, et al. Mammary Lymphoscintigraphy in Breast Cancer. J Nucl Med 36:1775–1780, 1995.

Veronesi U, Paganelli G, Galimberti V, et al. Sentinel-node biopsy to avoid axillary dissection in breast cancer with clinically negative lymph-nodes. Lancet 349:1864–1867, 1997.

Warbick A, Ege G, Henkelman R, Maier G and D Lyster. An Evaluation of Radiocolloid Sizing Techniques. Journal of Nuclear Medicine 18(8):827–834, 1977.

Warbick-Gerone A. Radiophannacology of Colloidal Dispersions. Current Applications in Radiopharmacology 139–147, 1986.

Zaiser E M and La Mer V K. J. Colloid Sci. 3, 571 (1948).

We claim:

1. A method of preparing a radiopharmaceutical composition comprising the steps of:

(a) providing reagents to produce a radiolabeled sulfur colloid;

(b) providing a reagent that reduces the size of the radiolabeled sulfur colloid comprising a source of thiol or its equivalent; and (c) mixing (a) and (b) and reacting under conditions to produce a radiolabeled sulfur colloid.

2. The method according to claim 1, wherein the reagents to produce a radiolabeled sulfur colloid comprise a radiolabel-producing reagent, a sulfur-producing reagent and an acid.

3. The method according to claim 2, wherein the sulfur-producing reagent is an alkali metal thiosulfate.

4. The method according to claim 3, wherein the sulfur-producing reagent is sodium thiosulfate.

5. The method according to claim 2, wherein the radiolabel-producing reagent comprises a radioisotope of technetium and/or rhenium.

6. The method according to claim 5, wherein the radiolabel-producing reagent comprises a radiolabel selected from the group consisting technetium-99m, rhenium-186 and rhenium-188.

7. The method according to claim 1, wherein the reagent that is capable of reducing the size of the radiolabeled sulfur colloid is an organic thiol.

8. The method according to claim 1, wherein the reagent that is capable of reducing the size of the radiolabeled sulfur colloid is an organic thiol.

9. The method according to claim 8, wherein the reagent that is capable of reducing the size of the radiolabeled sulfur colloid is selected from the group consisting of cysteine, glutathione and analogs thereof.

10. The method according to claim 1, wherein the reagents to form a radiolabeled sulfur colloid further comprise a nonradioactive rhenium-producing reagent.

11. The method according to claim 10, wherein the nonradioactive rhenium-producing reagent is an alkali metal perrhenate.

12. The method according to claim 11, wherein the nonradioactive rhenium-producing reagent is potassium perrhenate.

13. The method according to claim 10, wherein the nonradioactive rhenium-producing reagent and the sulfur-producing reagent are provided in amounts that result in a rhenium/sulfur atomic ratio, from the nonradioactive rhenium-producing reagent and the sulfur-producing reagent, in range of about 0.05 to about 1.2.

14. The method according to claim 13, wherein the nonradioactive rhenium-producing reagent and the sulfur-producing reagent are provided in amounts that result in a rhenium/sulfur atomic ratio, from the nonradioactive rhenium-producing reagent and the sulfur-producing reagent, of about 0.2 to about 0.3.

15. The method according to claim 12, wherein the sulfur-producing reagent is sodium thiosulfate and the molar ratio of potassium perrhenate/sodium thiosulfate is in the range about 0.4 to about 0.5.

16. The method according to claim 1, wherein the conditions to produce a radiolabeled sulfur colloid comprise heating to about 100° C.

17. The method according to claim 16, wherein the conditions to produce a radiolabeled sulfur colloid comprise heating for a time period of from about 0.5 minutes to about 1 hour.

18. The method according to claim 17, wherein the conditions to produce a radiolabeled sulfur colloid comprise heating for a time period of from about 6 minutes to about 10 minutes.

19. The method according to claim 1, further comprising the steps of:
(d) adding a buffer solution to the radiolabeled sulfur colloid of (c).

20. The method according to claim 19, wherein the buffer adjusts the pH of the composition to a range of about 5.5 to about 8.0.

21. The method according to claim 1, further comprising the steps of:
(d) cooling the radiolabeled sulfur colloid of (c); and
(e) adding a buffer solution to the radiolabeled sulfur colloid of (d).

22. The method according to claim 21, wherein the buffer adjusts the pH of the composition to a range of about 5.5 to about 8.0.

23. The method according to claim 21, wherein the cooling time is from about 1 minute to about 10 minutes.

24. The method according to claim 1, wherein the radiolabeled sulfur composition is not filtered before radiopharmaceutical use.

25. A radiopharmaceutical composition comprising the product obtained by:
(a) providing reagents to produce a radiolabeled sulfur colloid;
(b) providing a reagent that is capable of reducing the size of the radiolabeled sulfur colloid comprising a source of thiol; and
(c) mixing (a) and (b) and reacting under conditions to produce a radiolabeled sulfur colloid.

26. The composition according to claim 25, wherein the reagents to form a radiolabeled sulfur colloid comprise a radiolabel-producing reagent, a sulfur-producing reagent and an acid.

27. The composition according to claim 26, wherein the sulfur-producing reagent is an alkali metal thiosulfate.

28. The composition according to claim 26, wherein the sulfur producing reagent is sodium thiosulfate.

29. The composition according to claim 26, wherein the radiolabel-producing reagent comprises a radioisotope of technetium and/or rhenium.

30. The composition according to claim 29, wherein the radiolabel-producing reagent comprises the radiolabel selected from the group consisting technetium-99m, rhenium-186 and rhenium-188.

31. The composition according to claim 29, wherein the radiolabel producing reagent is technetium-99m pertechnetate.

32. The composition according to claim 31, wherein the reagent that is capable of reducing size of the radiolabeled sulfur colloid is an organic thiol.

33. The composition according to claim 32, wherein the reagent that is capable of reducing size of the radiolabeled sulfur colloid is selected from the group consisting of cysteine, glutathione and analogs thereof.

34. The composition according to claim 25, wherein the reagents to form a radiolabeled sulfur colloid further comprise a nonradioactive rhenium-producing reagent.

35. The composition according to claim 34, wherein the nonradioactive rhenium-producing reagent is an alkali metal perrhenate.

36. The composition according to claim 34, wherein the nonradioactive rhenium-producing reagent is potassium perrhenate.

37. The composition according to claim 34, wherein the nonradioactive rhenium-producing reagent and the sulfur-producing reagent are provided in amounts that result in a rhenium/sulfur atomic ratio, from the nonradioactive rhenium-producing reagent and the sulfur-producing reagent, in range of about 0.05 to about 1.2.

38. The composition according to claim 37, wherein the nonradioactive rhenium-producing reagent and the sulfur-producing reagent are provided in amounts that result in a rhenium/sulfur atomic ratio, from the nonradioactive rhenium-producing reagent and the sulfur-producing reagent, of about 0.2 to about 0.3.

39. The composition of claim 36, wherein the sulfur-producing reagent is sodium thiosulfate and the molar ratio of potassium perrhenate/sodium fate is in the range about 0.4 to about 0.5.

40. The composition according to claims 25, wherein the conditions to produce a radiolabeled sulfur colloid comprise heating to about 100° C.

41. The composition according to claim 40, wherein the conditions to produce a radiolabeled sulfur colloid comprise heating for a time period of from about 0.5 minutes to about 1 hour.

42. The composition according to claim 41, wherein the conditions to produce a radiolabeled sulfur colloid comprise heating for a time period of from about 6 minutes to about 10 minutes.

43. The composition according to claim 41, wherein the conditions to produce a radiolabeled sulfur colloid comprise heating for a time period of about 8 minutes.

44. The composition according to claim 29, wherein greater than about 80% of the radioactivity of isotopes of rhenium and/or technetium from the radiolabeled sulfur colloid passes through a 0.1 micron filter.

45. The composition according to claim 25, wherein a buffer solution is added to radiolabeled sulfur colloid of (c).

46. The composition according to claim 45, wherein the buffer adjusts the pH of the composition to a range of about 5.5 to about 8.0.

47. The composition according to claim 46, wherein the buffer adjusts the pH of the composition to a range of about 7.0 to about 7.5.

48. A method of preparing a radiolabeled sulfur colloid which increases the percentage of radioactivity from radioactive colloid particles labeled with radioisotopes of technetium and/or rhenium that pass through a 0.1 micron filter, wherein the method comprises adding an organic thiol to colloid-forming reagents before heating, and mixing and reacting under conditions to produce a radiolabeled sulfur colloid.

49. A method of detecting sentinel lymph node(s) in association with a primary cancer comprising administering an effective amount of a composition according to claim 25 to a subject, and identifying the area(s) of migrated radioactivity emitting the highest radioactivity counts to locate the associated sentinel lymph node(s).

50. The method according to claim 49, wherein the subject is human.

51. The method according to claim 49, wherein the cancer is one which is known to metastasize via lymph nodes.

52. A method of providing images of lung ventilation comprising inhalation of an effect amount of an aerosol of a composition according to claim 25 to a subject and detecting the radiation emitted from the subject.

53. A method of performing scintigraphy comprising administering an effective amount of a composition according to claim 25 to a subject, and identifying area(s) of migrated radioactivity emitting highest radioactivity counts.

54. The use method according to claim 53, wherein the scintigraphy is sentinel node lymphoscintigraphy.

55. The use method according to claim 54, wherein the radiolabeled sulfur containing colloid provides an entrapment ratio of greater than about 5 to about 20.

56. A method of performing radionuclidic radiation comprising administering an effective amount of a composition according to claim 25 to a subject, and identifying area(s) of migrated radioactivity emitting highest radioactivity counts.

57. The method according to claim 10, wherein the conditions to produce a radiolabeled sulfur colloid comprise heating to about 100° C.

58. The method according to claim 10, further comprising the steps of:
(d) adding a buffer solution to the radiolabeled sulfur colloid of (c).

59. The method according to claim 58, wherein the buffer adjusts the pH of the composition to a range of about 5.5 to about 8.0.

60. The method according to claim 10, further comprising the steps of:
(d) cooling the radiolabeled sulfur colloid of (c); and
(e) adding a buffer solution to the radiolabeled sulfur colloid of (d).

61. The method according to claim 60, wherein the buffer adjusts the pH of the composition to a range of about 5.5 to about 8.0.

62. The method according to claim 60, wherein the cooling time is from about 1 minute to about 10 minutes.

63. The method according to claim 10, wherein the radiolabeled sulfur composition is not filtered before radiopharmaceutical use.

64. A method of detecting sentinel lymph node(s) in association with a primary cancer comprising administering an effective amount of a composition according to claim 4 to a subject, and identifying the area(s) of migrated radioactivity emitting the highest radioactivity counts to locate the associated sentinel lymph node(s).

65. A method of providing images of lung ventilation comprising inhalation of an effect amount of an aerosol of a composition according to claim 34 to a subject and detecting the radiation emitted from the subject.

66. A method of performing scintigraphy comprising administering an effective amount of a composition according to claim 34 to a subject, and identifying area(s) of migrated radioactivity emitting highest radioactivity counts.

67. A method of performing radionuclidic radiation comprising administering an effective amount of a composition according to claim 34 to a subject, and identifying area(s) of migrated radioactivity emitting highest radioactivity counts.

68. The composition according to claim 25, wherein greater than about 80% of the radiolabeled sulfur colloid has a particle size of less than about 0.1 micron in diameter.

69. The composition according to claim 34, wherein greater than about 80% of the radiolabeled sulfur colloid has a particle size of less than about 0.1 micron in diameter.

70. The composition according to claim 34, wherein greater than about 80% of the radioactivity of isotopes of rhenium and/or technetium from the radiolabeled sulfur colloid passes through a 0.1 micron filter.

* * * * *